(12) United States Patent
Fairhurst et al.

(10) Patent No.: US 8,071,565 B2
(45) Date of Patent: Dec. 6, 2011

(54) PURINE DERIVATIVES AS A2A AGONISTS

(75) Inventors: Robin Alec Fairhurst, Horsham (GB); Roger John Taylor, Horsham (GB)

(73) Assignee: Novartis AG, Basel (CH)

( * ) Notice: Subject to any disclaimer, the term of this patent is extended or adjusted under 35 U.S.C. 154(b) by 251 days.

(21) Appl. No.: 12/308,637

(22) PCT Filed: Jul. 11, 2007

(86) PCT No.: PCT/EP2007/006156
§ 371 (c)(1),
(2), (4) Date: Dec. 18, 2008

(87) PCT Pub. No.: WO2008/006563
PCT Pub. Date: Jan. 17, 2008

(65) Prior Publication Data
US 2010/0240680 A1 Sep. 23, 2010

(30) Foreign Application Priority Data
Jul. 13, 2006 (EP) .................................. 06117168

(51) Int. Cl.
C07D 473/16 (2006.01)
A61K 31/52 (2006.01)
C07H 19/16 (2006.01)
A61P 29/00 (2006.01)
A61P 11/06 (2006.01)
C07D 473/40 (2006.01)
C07D 231/12 (2006.01)

(52) U.S. Cl. .................. 514/46; 514/263.2; 514/263.22; 536/27.61; 544/277; 548/376.1

(58) Field of Classification Search .................... 514/46; 536/27.61
See application file for complete search history.

(56) References Cited

U.S. PATENT DOCUMENTS

| 4,008,125 | A | 2/1977 | Kurozumi et al. |
| 4,738,954 | A | 4/1988 | Hamilton et al. |
| 4,873,360 | A | 10/1989 | Johnson et al. |
| 4,954,504 | A | 9/1990 | Chen et al. |
| 5,688,774 | A | 11/1997 | Jacobson et al. |
| 6,307,054 | B1 | 10/2001 | Truesdale et al. |
| 6,376,472 | B1 | 4/2002 | Myers et al. |
| 6,403,567 | B1 | 6/2002 | Zablocki et al. |
| 6,429,315 | B1 | 8/2002 | Sledeski et al. |
| 6,492,348 | B1 | 12/2002 | Bays et al. |
| 6,559,313 | B2 | 5/2003 | Myers et al. |
| 6,677,316 | B2 | 1/2004 | Bays et al. |
| 7,553,823 | B2 | 6/2009 | Zablocki et al. |
| 7,737,126 | B2 | 6/2010 | Blatcher et al. |
| 2003/0092668 | A1 | 5/2003 | Liang et al. |
| 2003/0176390 | A1 | 9/2003 | Herling et al. |
| 2004/0106572 | A1 | 6/2004 | Fishman et al. |
| 2004/0162422 | A1 | 8/2004 | Hall et al. |
| 2005/0101551 | A1 | 5/2005 | Sevillano et al. |
| 2005/0182018 | A1 | 8/2005 | Linden et al. |
| 2006/0142237 | A1 | 6/2006 | Fishman et al. |
| 2006/0189636 | A1 | 8/2006 | Critchley et al. |
| 2007/0099865 | A1 | 5/2007 | Fishman et al. |
| 2007/0191293 | A1 | 8/2007 | Langston et al. |
| 2007/0232626 | A1 | 10/2007 | Jacobson et al. |
| 2008/0027022 | A1 | 1/2008 | Linden et al. |
| 2008/0051364 | A1 | 2/2008 | Fishman et al. |
| 2008/0051404 | A1 | 2/2008 | Claiborne et al. |
| 2008/0200483 | A1 | 8/2008 | Fairhurst et al. |
| 2008/0207648 | A1 | 8/2008 | Fairhurst et al. |
| 2008/0214581 | A1 | 9/2008 | Allen et al. |
| 2008/0242683 | A1* | 10/2008 | Fairhurst et al. ......... 514/263.22 |
| 2008/0262001 | A1 | 10/2008 | Kranenburg et al. |
| 2008/0300213 | A1 | 12/2008 | Fishman |
| 2008/0312160 | A1 | 12/2008 | Guerrant et al. |

(Continued)

FOREIGN PATENT DOCUMENTS
EP 0 267 878 A1 5/1988
(Continued)

OTHER PUBLICATIONS

Baraldi et al., "Recent improvements in the field of A3 adenosine receptor ligands", Expert Opinion on Therapeutic Patents, vol. 15, No. 11 (2005), pp. 1507-1519.
Barnard et al., "Inhibition of measles virus replication by 5'-nor carbocyclic adenosine analogues", Antiviral Chemistry & Chemotherapy, vol. 12, No. 4 (2001), pp. 241-250.
Broadley et al., "Drugs Modulating Adenosine Receptors as Potential Therapeutic Agents for Cardiovascular Diseases", Expert Opinion on Therapeutic Patents, vol. 10, No. 11 (2000), pp. 1669-1692.
Cowart et al., "Synthesis of Novel Carbocyclic Adenosine Analogues as Inhibitors of Adenosine Kinase", J. Org. Chem., vol. 64, No. 7 (1999), pp. 2240-2249.

(Continued)

Primary Examiner — Mark Berch
(74) Attorney, Agent, or Firm — Paul D. Strain; Strain & Strain PLLC

(57) ABSTRACT

Compounds of formula (I): or stereoisomers or pharmaceutically acceptable salts thereof, wherein W, $R^1$, $R^2$ and $R^3$ have the meanings as indicated in the specification, are useful for treating conditions mediated by activation of the adenosine $A_{2A}$ receptor, especially inflammatory or obstructive airways diseases. Pharmaceutical compositions that contain the compounds and a process for preparing the compounds are also described.

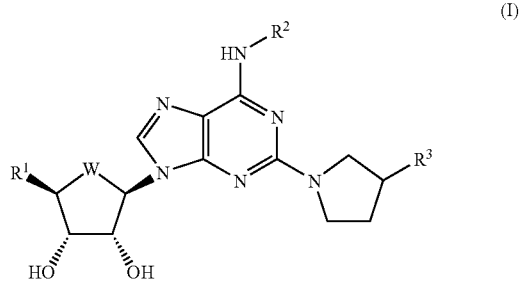

(I)

3 Claims, No Drawings

U.S. PATENT DOCUMENTS

| | | | |
|---|---|---|---|
| 2009/0012035 | A1 | 1/2009 | Jacobson et al. |
| 2009/0054476 | A1 | 2/2009 | Goblyos et al. |
| 2009/0081764 | A1 | 3/2009 | Pausch et al. |
| 2009/0093633 | A1 | 4/2009 | Fairhurst et al. |
| 2009/0099214 | A1 | 4/2009 | Fairhurst et al. |
| 2009/0105476 | A1 | 4/2009 | Fairhurst et al. |
| 2009/0123510 | A1 | 5/2009 | Cronstein et al. |
| 2009/0181920 | A1 | 7/2009 | Watkins et al. |
| 2009/0181934 | A1 | 7/2009 | Fairhurst |
| 2009/0240045 | A1 | 9/2009 | Fairhurst et al. |
| 2009/0281126 | A1 | 11/2009 | Fairhurst et al. |
| 2009/0281127 | A1 | 11/2009 | Fairhurst et al. |
| 2009/0325967 | A1 | 12/2009 | Fairhurst et al. |
| 2010/0041918 | A1 | 2/2010 | Laumen |
| 2010/0190784 | A1* | 7/2010 | Fairhurst et al. ............ 514/232.5 |
| 2010/0197914 | A1* | 8/2010 | Fairhurst ....................... 544/277 |
| 2010/0286126 | A1* | 11/2010 | Fairhurst et al. .............. 514/218 |

FOREIGN PATENT DOCUMENTS

| | | |
|---|---|---|
| JP | 63-219387 | 9/1988 |
| WO | WO 92/05177 A1 | 4/1992 |
| WO | WO 93/22328 A1 | 11/1993 |
| WO | WO 98/50047 A1 | 11/1998 |
| WO | WO 99/67263 | 12/1999 |
| WO | WO 99/67265 | 12/1999 |
| WO | WO 99/67266 A1 | 12/1999 |
| WO | WO 00/23457 | 4/2000 |
| WO | WO 00/78774 A2 | 12/2000 |
| WO | WO 00/78779 A2 | 12/2000 |
| WO | WO 01/60835 A1 | 8/2001 |
| WO | WO 02/22630 A1 | 3/2002 |
| WO | WO 02/055085 A2 | 7/2002 |
| WO | WO 02/070534 | 9/2002 |
| WO | WO 03/029264 | 4/2003 |
| WO | WO 03/086408 A1 | 10/2003 |
| WO | WO 2005/063246 A1 | 7/2005 |
| WO | WO 2005/084653 A2 | 9/2005 |
| WO | WO 2005/107463 A1 | 11/2005 |
| WO | WO 2005/116037 A1 | 12/2005 |
| WO | WO 2006/011130 A1 | 2/2006 |
| WO | WO 2006/045552 | 5/2006 |
| WO | WO 2006/074925 | 7/2006 |
| WO | WO 2006/097260 | 9/2006 |
| WO | WO 2007/121917 A2 | 11/2007 |
| WO | WO 2007/121919 A1 | 11/2007 |
| WO | WO 2007/121920 A2 | 11/2007 |
| WO | WO 2007/121921 A2 | 11/2007 |
| WO | WO 2007/121923 A1 | 11/2007 |
| WO | WO 2007/121924 A2 | 11/2007 |
| WO | WO 2007/147659 A1 | 12/2007 |
| WO | WO 2008/006563 A1 | 1/2008 |

OTHER PUBLICATIONS

Curran et al., "The Preparation of Optically Active 2, Cyclopenten-1,4-Diol Derivatives from Furfuryl Alcohol", Tetrahedron, vol. 53, No. 6 (1997), pp. 1983-2004.

Duhamel et al., "Acylation Enatioselective D'un Diol, Meso: Le Cis-Cyclopenthen-2 Diol-1,4", Tetrahedron Letters, vol. 26, No. 26 (1985), pp. 3099-3102.

Galkina et al., "Studies on an Oixdative, 1,4-Addition to s-trans-1,3-Dienes, a Key Reaction in a Strigol Total Synthesis", Eur. J. Org. Chem., (2003), pp. 4640-4653.

Ghosh et al. "Synthesis of Enantiomerically Pure 5'-Aza Noraristeromycin Analogs", J. Org. Chem., vol. 60, No. 18 (1995), pp. 5808-5813.

Hegde et al., "5'-Amino-5'-deoxy-5'-noraristeromycin", Chemical Abstracts Index entry for Journal of Organic Chemistry, vol. 63, No. 20 (1998), pp. 7092-7094.

Hegde et al., "5'-Amino-5'-deoxy-5'noraristeromycin", J. Org. Chem., vol. 63, No. 20 (1998), pp. 7092-7094.

Kikugawa et al., "Platelet Aggregation Inhibitors. 6. 12-Thioadenosine Derivatives", Journal of Medicinal Chemistry, vol. 16, No. 12 (1973), pp. 1381-1388.

Marlene A Jacobsen, "Adenosine receptor agonists", Expert Opinion Therapeutic Targets, vol. 12, No. 4 (2002), pp. 489-501.

Marumoto et al., "Synthesis and Coronary Vasodilating Activity of 2-Substituted Adenosines", Chemical and Pharmaceutical Bulletin, vol. 23, No. 4 (1975), pp. 759-774.

Oriyama et al., "Catalytic Asymmetrization of CIS-2-Cyclopentene-1,4-Diol. Highly Efficient and Practical Synthesis . . .", Heterocycles, vol. 52, No. 3 (2000), pp. 1055-1069.

Palle et al., "Structure-Affinity Relationships of the Affinity of 2-Pyrazolyl Adenosine Analogues for the Adenosine A2A Receptor", Bioorganic & Medicinal Chemistry Letters, vol. 12, No. 20 (2002), pp. 2935-2939.

Silverman J, Rheumatol, vol. 35, No. 4(2008), pp. 1-8.

Terashima et al., "Novel Use of Meso-Compound for the Preparation of Optically Active Compounds . . .", Tetrahedron Letters, vol. 11 (1977), pp. 1001-1004.

Yang et al., "Amino substituted derivatives of 5'-amino-5'-deoxy-5'-noraristeromycin", Bioorganic & Medicinal Chemistry, vol. 13, No. 3 (2005), pp. 877-882.

Fairhurst, U.S. PTO Office Action, U.S. Appl. No. 11/576,607, Jan. 11, 2010, 39 pgs.

Fairhurst, U.S. PTO Office Action, U.S. Appl. No. 11/576,607, Dec. 23, 2009, 43 pgs.

Fairhurst, U.S. PTO Office Action, U.S. Appl. No. 11/576,607, Jul. 16, 2010, 40 pgs.

Fairhurst, U.S. PTO Office Action, U.S. Appl. No. 11/722,835, Dec. 22, 2009, 37 pgs.

Fairhurst, U.S. PTO Office Action, U.S. Appl. No. 11/722,835, Jul. 16, 2010, 32 pgs.

Fairhurst, U.S. PTO Office Action, U.S. Appl. No. 12/296,714, Jan. 5, 2010, 4 pgs.

Fairhurst, U.S. PTO Office Action, U.S. Appl. No. 12/296,714, May 19, 2010, 63 pgs.

Fairhurst, U.S. PTO Office Action, U.S. Appl. No. 12/296,714, Dec. 23, 2009, 12 pgs.

Fairhurst, U.S. PTO Office Action, U.S. Appl. No. 12/296,714, Dec. 30, 2009, 10 pgs.

Fairhurst, U.S. PTO Office Action, U.S. Appl. No. 12/297,373, Dec. 22, 2009, 8 pgs.

Fairhurst, U.S. PTO Office Action, U.S. Appl. No. 12/297,373, Jul. 15, 2010, 8 pgs.

Fairhurst, U.S. PTO Office Action, U.S. Appl. No. 12/297,404, Dec. 30, 2009, 18 pgs.

Fairhurst, U.S. PTO Office Action, U.S. Appl. No. 12/297,404, Jul. 15, 2010, 38 pgs.

Fairhurst, U.S. PTO Office Action, U.S. Appl. No. 12/297,940, Jan. 22, 2010, 15 pgs.

Fairhurst, U.S. PTO Office Action, U.S. Appl. No. 12/297,007, Dec. 23, 2009, 11 pgs.

Fairhurst, U.S. PTO Office Action, U.S. Appl. No. 12/297,007, Jul. 15, 2010, 32 pgs.

International Search Report, PCT/EP2007/059666, Jan. 18, 2008, 3 pgs.

Kerns et al., "Drug-like Properties: Concepts, Structure Design and Methods: from ADME to Toxicity Optimization", Elsevier (2008), pp. 92-93.

Goosen et al., "Physicochemical Characterization and Solubility Analysis of Thalidomide and Its N-Alkyl Analogs", Pharmaceutical Research, vol. 19, No. 1 (2002), pp. 13-19.

Fourie et al., "Percutaneous delivery of carbamazepine and selected N-alkyl and N-hydroxyalkyl analogues", International Journal of Pharmaceutics, vol. 279, Issues 1-2 (2004), pp. 59-66.

Edwards et al., "Nonpeptidic Inhibitors of Human Neutrophil Elastase. 7. Design, Synthesis, and in Vitro Activity of a Series of Pyridopyrimidine Trifluoromethyl Ketones", J. Med. Chem., vol. 39 (1996), pp. 1112-1124.

Rautio et al., "Piperazinylalkyl prodrugs of naproxen improve in vitro skin permeation", European Journal of Pharmaceutical Sciences, vol. 11 (2000), pp. 157-163.

Unpublished Pending U.S. Appl. No. 12/297,291, Fairhurst et al., filed Oct. 15, 2008.

Unpublished Pending U.S. Appl. No. 12/297,491, Fairhurst et al., filed Oct. 17, 2008.

International Search Report, PCT/EP2007/006156, Oct. 12, 2007.

Fairhurst et al., U.S. PTO Office Action, U.S. Appl. No. 12/297,727, Oct. 4, 2010, 13 pgs.

Bressi et al., "Adenosine Analogues as Inhibitors of Trypanosoma brucei Phosphoglycerate Kinase: Elucidation of a Novel Binding Mode for a 2-Amino-N6-Substituted Adenosine", Journal of Medicinal Chemistry, vol. 43, No. 22 (2000), pp. 4135-4150.

Fairhurst, U.S. PTO Notice of Allowance, U.S. Appl. No. 11/576,607, filed Jun. 9, 2011, 7 pgs.

Fairhurst, U.S. PTO Notice of Allowance, U.S. Appl. No. 11/722,835, filed May 27, 2011, 7 pgs.

Fairhurst, U.S. PTO Notice of Allowance, U.S. Appl. No. 12/297,291, filed Jul. 14, 2011, 9 pgs.

Fairhurst, U.S. PTO Office Action, U.S. Appl. No. 11/576,607, filed Feb. 17, 2011, 12 pgs.

Fairhurst, U.S. PTO Office Action, U.S. Appl. No. 11/722,835, filed Jan. 3, 2011, 12 pgs.

Fairhurst, U.S. PTO Office Action, U.S. Appl. No. 12/296,714, filed Jan. 3, 2011, 16 pgs.

Fairhurst, U.S. PTO Office Action, U.S. Appl. No. 12/296,714, filed Apr. 28, 2011, 7 pgs.

Fairhurst, U.S. PTO Office Action, U.S. Appl. No. 12/297,291, filed Mar. 21, 2011, 41 pgs.

Fairhurst, U.S. PTO Office Action, U.S. Appl. No. 12/297,291, filed Dec. 1, 2010, 21 pgs.

Fairhurst, U.S. PTO Office Action, U.S. Appl. No. 12/297,491, filed Mar. 24, 2011, 20 pgs.

Fairhurst, U.S. PTO Office Action, U.S. Appl. No. 12/310,254, filed Mar. 24, 2011, 18 pgs.

Fairhurst, U.S. PTO Office Action, U.S. Appl. No. 12/679,663, filed Feb. 28, 2011, 21 pgs.

Fairhurst, U.S. PTO Supplemental Notice of Allowance, U.S. Appl. No. 11/576,607, filed Jun. 15, 2011, 3 pgs.

Ghosh et al., "Synthesis and Biological Evaluation of a Carbocyclic Azanoraristeromycin Siderophore Conjugate", Nucleosides & Nucleotides, vol. 18, No. 2 (1999), pp. 217-225.

Wanner et al., "Synthesis and properties of 2-nitrosoadenosine", J. Chem. Soc., Perkin Trans., vol. 1 (2001), pp. 1908-1915.

Fairhurst, U.S. PTO Restriction Requirement, U.S. Appl. No. 12/247,764, filed Jul. 15, 2011, 14 pgs.

International Search Report, PCT/EP2008/063869, Jul. 21, 2009, 7 pgs.

Laumen, U.S. PTO Office Action, U.S. Appl. No. 12/312,311, filed Aug. 9, 2011, 20 pgs.

Siddiqi et al., "Enantiospecific Synthesis of the Fluoro and Epimeric Derivatives of 5'-Noraristeromycin", J. Chem. Soc., Chem. Commun., 1993, pp. 708-709.

Unpublished pending U.S. Appl. No. 13/218,865, Robin Alec Fairhurst et al., filed Aug. 26, 2011.

Unpublished pending U.S. Appl. No. 13/218,887, Robin Alec Fairhurst et al., filed Aug. 26, 2011.

Fairhurst, U.S. PTO Office Action, U.S. Appl. No. 12/297,491, Oct. 12, 2011, 11 pgs.

Fairhurst, U.S. PTO Office Action, U.S. Appl. No. 12/310,254, Oct. 12, 2011, 11 pgs.

* cited by examiner

PURINE DERIVATIVES AS A2A AGONISTS

This invention relates to organic compounds, their preparation and use as pharmaceuticals.

An aspect of the present invention provides compounds of formula (I)

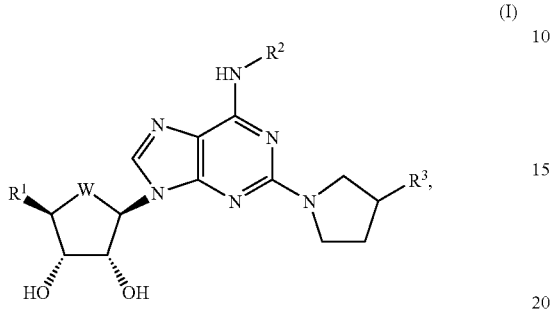

(I)

or stereoisomers or pharmaceutically acceptable salts thereof, wherein

W is $CH_2$ or O, with the proviso that when W is O, then $R^1$ is not a N-bonded substituent;

$R^1$ is a 3- to 12-membered heterocyclic group containing from 1 to 4 ring nitrogen atoms and optionally containing from 1 to 4 other heteroatoms selected from the group consisting of oxygen and sulfur, that group being optionally substituted by oxo, $C_1$-$C_8$-alkoxy, $C_6$-$C_{10}$-aryl, $R^{1a}$ or by $C_1$-$C_8$-alkyl optionally substituted by hydroxyl;

$R^{1a}$ is a 3- or 12-membered heterocyclic ring containing at least one ring heteroatom selected from the group consisting of nitrogen, oxygen and sulfur, said 3- or 12-membered heterocyclic ring being optionally substituted by halo, cyano, oxo, hydroxy, carboxy, amino, nitro, $C_1$-$C_8$-alkyl, $C_1$-$C_8$-alkylsulfonyl, aminocarbonyl, $C_1$-$C_8$-alkylcarbonyl or $C_1$-$C_8$-alkoxy optionally substituted by aminocarbonyl;

$R^2$ is $C_1$-$C_8$-alkyl substituted by OH, halogen $C_6$-$C_{10}$-aryl optionally substituted by OH, $SO_2R^5$, $SC_1$-$C_8$ alkyl, CN, halogen, O—$C_7$-$C_{14}$-aralkyl, or O—$C_1$-$C_8$-alkyl, a $C_3$-$C_{15}$-carbocyclic group optionally substituted by O—$C_7$-$C_{14}$ aralkyl, $C_3$-$C_{15}$-carbocyclic group, O—$C_1$-$C_8$-alkyl, $C_2$-$C_8$-alkenyl, $C_2$-$C_8$-alkynyl or $C_1$-$C_8$-alkyl, O—$C_1$-$C_8$-alkyl, —$SO_2C_1$-$C_8$-alkyl, a 3- to 12-membered heterocyclic group containing from 1 to 4 ring nitrogen atoms and optionally containing from 1 to 4 other heteroatoms selected from the group consisting of oxygen and sulfur, that group being optionally substituted by 3- to 12-membered heterocyclic group containing from 1 to 4 ring nitrogen atoms and optionally containing from 1 to 4 other heteroatoms selected from the group consisting of oxygen and sulfur. $C_7$-$C_{14}$-aralkyl, or $C_6$-$C_{14}$-aryl optionally substituted by O—$C_7$-$C_{14}$-aralkyl, or $R^2$ is a $C_3$-$C_{15}$-carbocyclic group optionally substituted by O—$C_7$-$C_{14}$-aralkyl, $C_3$-$C_{15}$-carbocyclic group, O—$C_1$-$C_6$-alkyl, or $C_1$-$C_8$-alkyl, or $R^2$ is a 3- to 12-membered heterocyclic group containing from 1 to 4 ring nitrogen atoms and optionally containing from 1 to 4 other heteroatoms selected from the group consisting of oxygen and sulfur, that group being optionally substituted by 3- to 12-membered heterocyclic group containing from 1 to 4 ring nitrogen atoms and optionally containing from 1 to 4 other heteroatoms selected from the group consisting of oxygen and sulfur, $C_7$-$C_{14}$-aralkyl, or $C_6$-$C_{10}$-aryl optionally substituted by O—$C_7$-$C_{14}$-aralkyl;

$R^3$ is selected from $NR^{3a}R^{3b}$, $NR^3C(O)NR^{3g}R^{3h}$, $NHC(O)R^{3q}$, and $NHC(=NR^{3m})N(R^{3n})R^{3o}$, $R^{3a}$, $R^{3f}$ and $R^{3h}$ are, independently, H, $C_1$-$C_8$-alkyl or $C_5$-$C_{10}$-aryl;

$R^{3b}$ is H, $C_1$-$C_8$-alkyl a 3- to 12-membered heterocyclic group containing at least one ring heteroatom selected from the group consisting of nitrogen, oxygen and sulfur, optionally substituted by 0-3$R^4$ or $C_6$-$C_{10}$-aryl;

$R^{3g}$ is $C_1$-$C_8$-alkyl optionally substituted by a 3- to 12-membered heterocyclic group containing at least one ring heteroatom selected from the group consisting of nitrogen, oxygen and sulfur, optionally substituted with $SO_2R^5$, CN, or 0-3$R^4$, or $R^{3g}$ is a $C_6$-$C_{10}$-aryl optionally substituted by OH, $C_1$-$C_8$-alkyl, O—$C_1$-$C_8$-alkyl, CN, —C(=NH)$NH_2SO_2R^5$, -halogen, or a 3- to 12-membered heterocyclic group containing at least one ring heteroatom selected from the group consisting of nitrogen, oxygen and sulfur, optionally substituted by 0-3$R^4$, or $R^{3g}$ is a $C_7$-$C_{14}$-aralkyl optionally substituted by OH, O—$C_1$-$C_8$-alkyl, halogen, $C_6$-$C_{10}$-aryl, $SO_2R^5$, CN, —C(=NH)$NH_2$, or O—$C_6$-$C_{10}$-aryl, or $R^{3g}$ is a 3- to 12-membered heterocyclic group containing at least one ring heteroatom selected from the group consisting of nitrogen, oxygen and sulfur, optionally substituted by 0-3$R^4$;

$R^{3m}$ is CN;

$R^{3n}$ is H or $C_1$-$C_8$-alkyl;

$R^{3o}$ is H, $C_1$-$C_8$-alkyl optionally substituted by OH or by a 3- to 12-membered heterocyclic group containing at least one ring heteroatom selected from the group consisting of nitrogen, oxygen and sulfur, optionally substituted with $SO_2R^5$, CN, or 0-3$R^4$, $C_1$-$C_8$-alkoxy, $C_7$-$C_{14}$-aralkyl optionally substituted with OH, O—$C_1$-$C_8$-alkyl, halogen $C_6$-$C_{10}$-aryl, or O—$C_6$-$C_{10}$-aryl, $C_1$-$C_8$-alkoxy, $C_6$-$C_{10}$-aryl optionally substituted by OH, $C_1$-$C_8$-alkyl, O—$C_1$-$C_8$-alkyl $SO_2R^5$ or -halogen;

$R^{3p}$ is H, $C_1$-$C_8$-alkyl or $C_7$-$C_{14}$-aralkyl;

$R^{3q}$ is a $C_6$-$C_{10}$-aryl optionally substituted by OH, $C_1$-$C_8$-alkyl, $C_1$-$C_8$-alkoxy, $SO_2R^5$ or -halogen, or $R^{3q}$ is a $C_7$-$C_{14}$-aralkyl optionally substituted by OH, $C_1$-$C_8$-alkyl, $C_1$-$C_8$-alkoxy, $SO_2R^5$ or -halogen, or $R^{3q}$ is a 3- to 12-membered heterocyclic group containing at least one ring heteroatom selected from the group consisting of nitrogen, oxygen and sulfur optionally substituted by 0-3$R^4$ or a 3- to 12-membered heterocyclic group containing at least one ring heteroatom selected from the group consisting of nitrogen, oxygen and sulfur, optionally substituted by 0-3$R^4$, $R^4$ is selected from OH, $C_1$-$C_8$-alkyl optionally substituted by OH, CN, $SO_2R^5$ or halogen, C(O)$NHR^{3a}$, O—$C_1$-$C_8$-alkyl optionally substituted by halogen, $NR^{4a}R^{4b}$, $NHC(O)R^{4c}$, a C(O)—$C_6$-$C_{10}$-aryl optionally substituted by OH, $C_1$-$C_8$-alkyl, O—$C_1$-$C_8$-alkyl, -halogen, or $SO_2R^5$;

$R^{4a}$, $R^{4b}$ and $R^{4c}$ are, independently, H, $C_1$-$C_8$-alkyl or $C_6$-$C_{10}$-aryl; and $R^5$ is $C_1$-$C_8$-alkyl optionally substituted by halogen, $C_6$-$C_{10}$-aryl optionally substituted by OH, $C_1$-$C_8$-alkyl, O—$C_1$-$C_8$-alkyl, or $NR^{3a}R^{3b}$.

DEFINITIONS

Terms used in the specification have the following meanings:

"Optionally substituted" or "substituted" means the group referred to can be substituted at one or more positions by any one or any combination of the radicals listed thereafter.

"Halo" or "Halogen", as Used Herein, May be Fluorine, Chlorine, Bromine or Iodine.

"$C_1$-$C_8$-Alkyl", as used herein, denotes straight chain or branched alkyl having 1 to 8 carbon atoms.

"$C_1$-$C_8$-Alkoxy", as used herein, denotes straight chain or branched alkoxy having 1 to 8 carbon atoms.

"$C_3$-$C_8$-Cycloalkyl", as used herein, denotes cycloalkyl having 3 to 8 ring carbon atoms, e.g., a monocyclic group, such as a cyclopropyl, cyclobutyl, cyclopentyl, cyclohexyl, cycloheptyl or cyclooctyl, any of which can be substituted by one or more, usually one or two, $C_1$-$C_4$-alkyl groups; or a bicyclic group, such as bicycloheptyl or bicyclooctyl.

"$C_1$-$C_8$-Alkylamino" and "di($C_1$-$C_8$-alkyl)amino", as used herein, denote amino substituted respectively by one or two $C_1$-$C_8$-alkyl groups as hereinbefore defined, which may be the same or different.

"$C_1$-$C_8$-Alkylcarbonyl" and "$C_1$-$C_8$-alkoxycarbonyl", as used herein, denote $C_1$-$C_8$-alkyl or $C_1$-$C_8$-alkoxy, respectively, as hereinbefore defined attached by a carbon atom to a carbonyl group.

"$C_6$-$C_{10}$-Aryl", as used herein, denotes a monovalent carbocyclic aromatic group that contains 6 to 10 carbon atoms and which may be, e.g., a monocyclic group, such as phenyl; or a bicyclic group, such as naphthyl.

"$C_7$-$C_{14}$-Aralkyl", as used herein, denotes alkyl, e.g., $C_1$-$C_4$-alkyl, as hereinbefore defined, substituted by $C_6$-$C_{10}$-aryl as hereinbefore defined.

"$C_1$-$C_8$-Alkylaminocarbonyl" and "$C_3$-$C_8$-cycloalkylaminocarbonyl", as used herein, denote $C_1$-$C_8$-alkylamino and $C_3$-$C_8$-cycloalkylamino respectively as hereinbefore defined attached by a carbon atom to a carbonyl group.

"$C_3$-$C_{15}$-Carbocyclic group", as used herein, denotes a carbocyclic group having 3 to ring carbon atoms, e.g., a monocyclic group, either aromatic or non aromatic, such as a cyclopentyl, cyclohexyl, cycloheptyl, cyclooctyl or phenyl; or a bicyclic group, such as bicyclooctyl, bicyclononyl, bicyclodecyl, indanyl or indenyl, again any of which can be substituted by one or more, usually one or two, $C_1$-$C_4$-alkyl groups.

"3- to 12-Membered heterocyclic ring containing at least one ring heteroatom selected from the group consisting of nitrogen, oxygen and sulfur", as used herein, may be, e.g., furan, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, morpholino, triazine, oxazine or thiazole.

"5- or 6-Membered heterocyclic group containing at least one ring heteroatom selected from the group consisting of nitrogen, oxygen and sulfur" as used herein may be, e.g., a saturated or unsaturated heterocyclic group, such as furanyl, pyrrolyl, pyrrolidinyl, pyrazolyl, imidazolyl, triazolyl, isothiazolyl, tetrazolyl, thiadiazolyl, isothiazolyl, oxadiazolyl, pyridinyl, piperidinyl, pyrazinyl, oxazolyl, isoxazolyl, pyrazinyl, pyridazinyl, pyrimidinyl, piperazinyl, pyrrolidinyl, morpholinyl, triazinyl, oxazinyl or thiazolyl.

Throughout this specification and in the claims that follow, unless the context requires otherwise, the word "comprise", or variations, such as "comprises" or "comprising", will be understood to imply the inclusion of a stated integer or step or group of integers or steps but not the exclusion of any other integer or step or group of integers or steps.

Throughout this specification and in the claims that follow, unless the context requires otherwise, the word "comprise", or variations, such as "comprises" or "comprising", will be understood to imply the inclusion of a stated integer or step or group of integers or steps but not the exclusion of any other integer or step or group of integers or steps. As understood by one skilled in the art only combinations of substituents that are chemically possible are embodiments of the invention.

According to formula (I), $R^1$ is suitably a 3- to 12-membered heterocyclic group containing at least one ring heteroatom selected from the group consisting of nitrogen, oxygen and sulfur. Preferably $R^1$ is a 5-membered heterocyclic group, such as pyazole, triazole, tetrazole, isoxazole and imidazole-2,4-dione. These heterocyclic groups are suitably substituted by a $C_1$-$C_8$-alkyl optionally substituted by OH.

The heterocyclic groups can be either N-bonded or C-bonded. For example, the heterocyclic groups pyrazole, triazole, tetrazole and imidazole-2,4-dione are suitably N-bonded when attached to a cyclopentane group (e.g., when W is $CH_2$). These N-bonded heterocyclic groups can also be suitably substituted by groups such as methanol, methyl, ethyl, methoxy and methoxy-methyl. Preferably, the $R^1$ groups attached to the cyclopentane group are

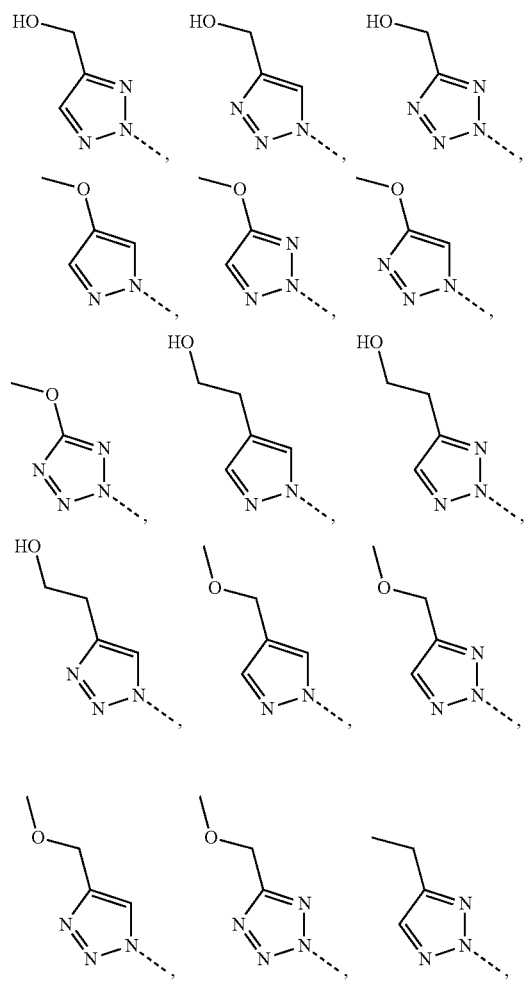

-continued

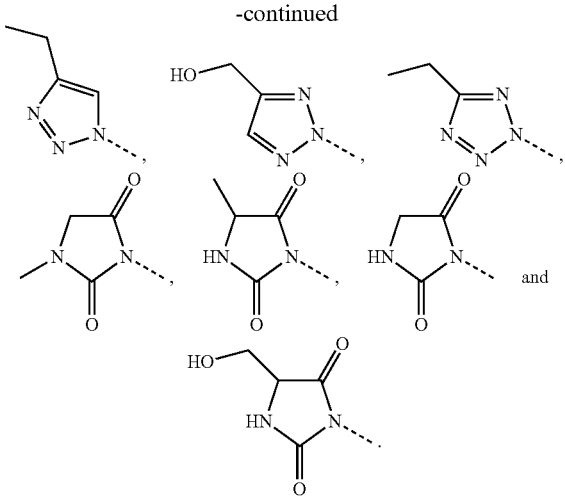

The heterocyclic groups isoxazole and tetrazole are C-bonded when attached to a furan group (e.g., when W is O). These C-bonded heterocyclic groups are suitably substituted by $C_1$-$C_8$-alkyl optionally substituted by OH such as hydroxymethyl, hydroxyethyl, an ethyl group or a methyl group. Preferably, The $R^1$ groups attached to the furan group are

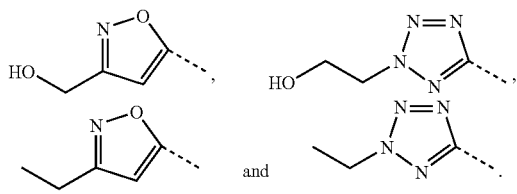

According to formula (I), $R^2$ is suitably selected from $C_1$-$C_8$-alkyl optionally substituted by OH, halogen or $C_8$-$C_{10}$-aryl optionally substituted by OH, halogen, such as Cl or O—$C_1$-$C_8$-alkyl, preferably $C_6$-$C_{10}$-aryl is phenyl. Also, preferably, the $C_1$-$C_8$-alkyl is substituted by two phenyl rings and the phenyl rings are unsubstituted or substituted by OH. Preferred $R^2$ groups are

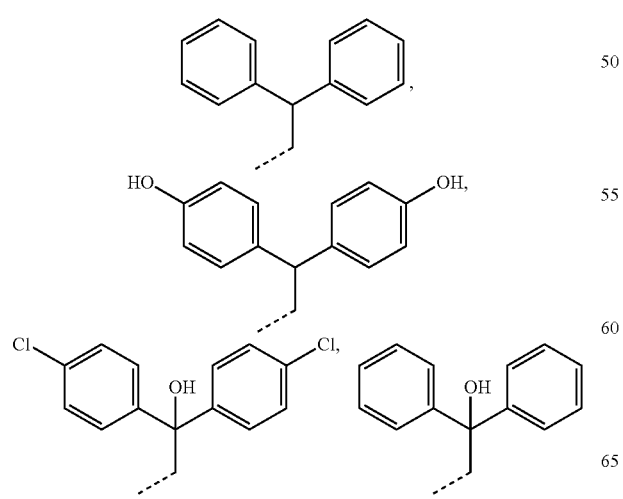

-continued

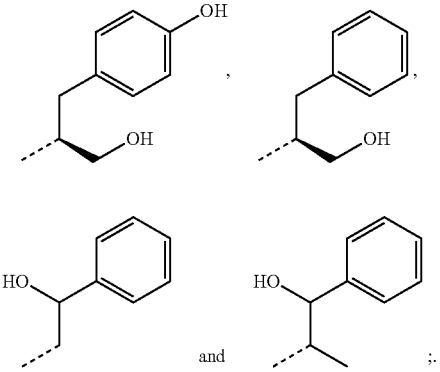

According to formula (I), $R^3$ is suitably $NR^{3f}C(O)$ $NR^{3g}R^{3h}$. $R^{3f}$ and $R^{3h}$ are suitably H.

$R^{3g}$ is suitably $C_6$-$C_{10}$-aryl optionally substituted by OH, $C_1$-$C_8$-alkyl, O—$C_1$-$C_8$-alkyl, $SO_2R^5$, -halogen, CN, —C(=NH)$NH_2$, or a 3- to 12-membered heterocyclic group containing at least one ring heteroatom selected from the group consisting of nitrogen, oxygen and sulfur, optionally substituted by 0-3$R^4$. Preferably this 3- to 12-membered heterocyclic group is a 5-membered heterocyclic group, such as tetrazole.

According to formula (I), $R^1$ is also suitably $C_7$-$C_{14}$-aralkyl optionally substituted by OH, O—$C_1$-$C_8$-alkyl, halogen, $C_6$-$C_{10}$-aryl, $SO_2R_5$, CN, —C(=NH)$NH_2$, or O—$C_6$-$C_{10}$-aryl.

According to formula (I), $R^{3g}$ is also suitably 3- to 12-membered heterocyclic group, preferably a pyridine, containing at least one ring heteroatom selected from the group consisting of nitrogen, oxygen and sulfur, optionally substituted by 0-3$R^4$.

According to formula (I), $R^3$ is also suitably $NHC(O)R^{3q}$, where $R^{3q}$ is a $C_6$-$C_{10}$-aryl optionally substituted by OH, $C_1$-$C_8$-alkyl, $C_1$-$C_8$-alkoxy, $SO_2R^5$ or -halogen.

$R^{3q}$ is also suitably a $C_7$-$C_{14}$-aralkyl optionally substituted by OH, $C_1$-$C_8$-alkyl, $C_1$-$C_8$-alkoxy, $SO_2R_5$ or -halogen.

Preferred $R^3$ groups are

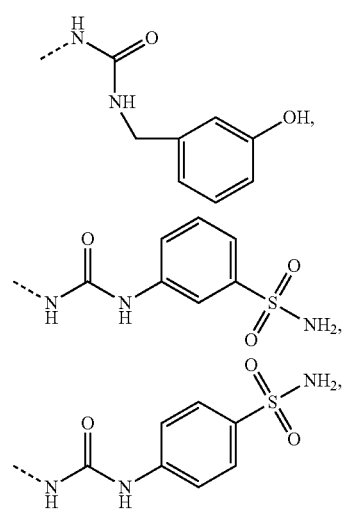

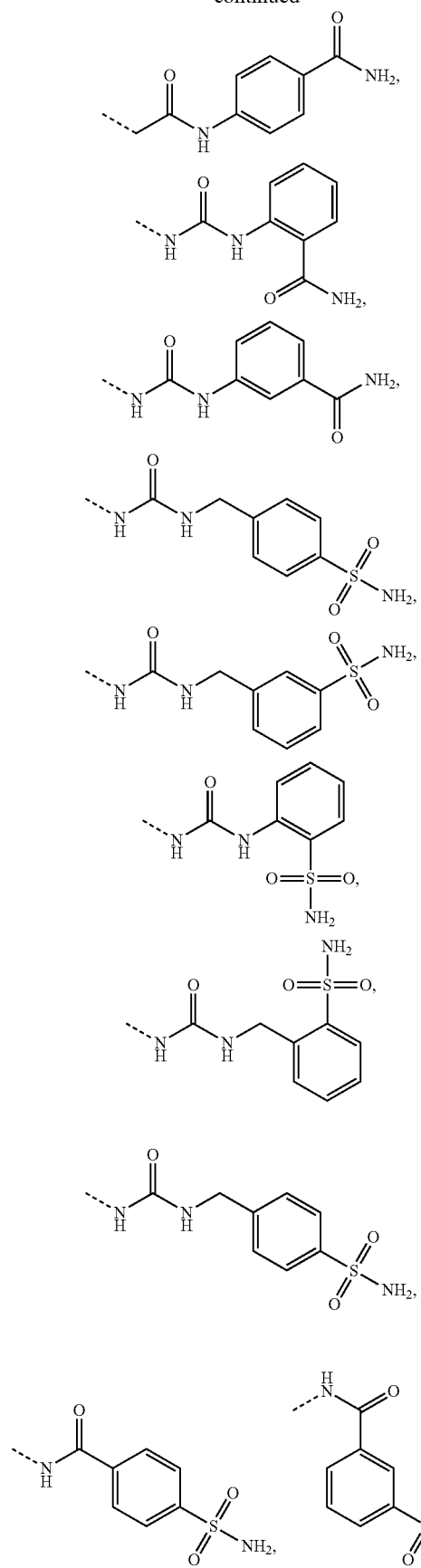
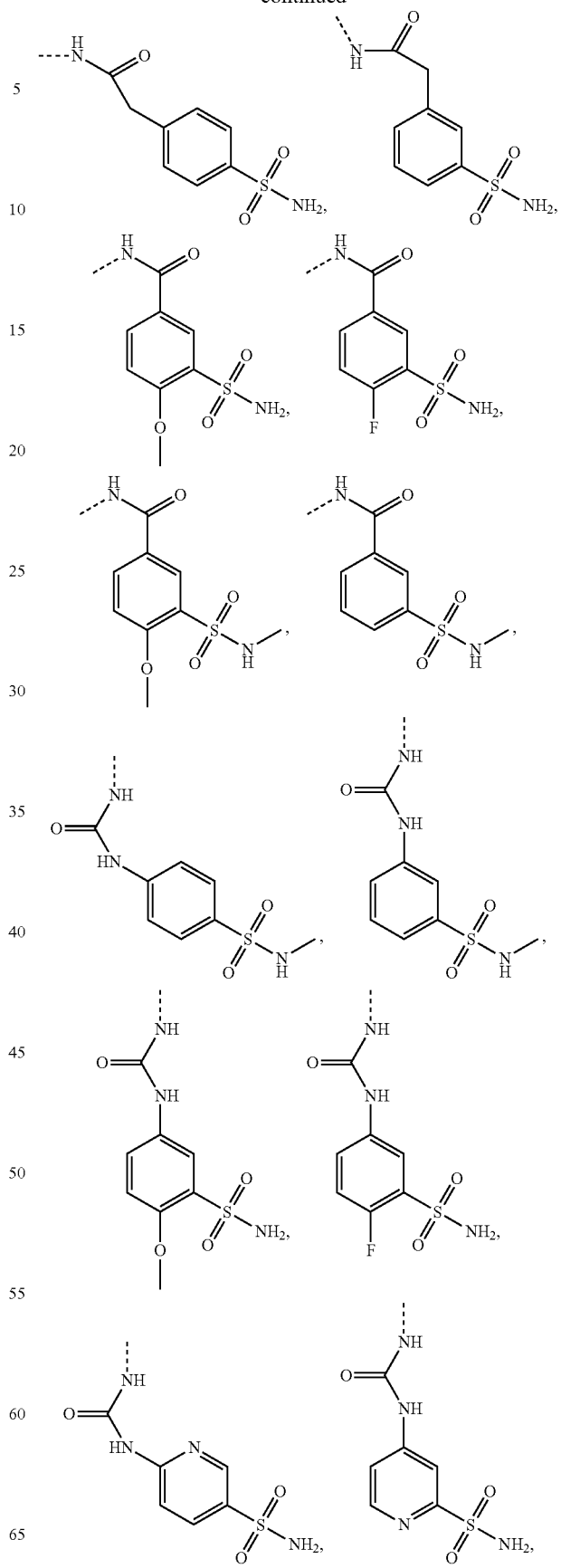

-continued
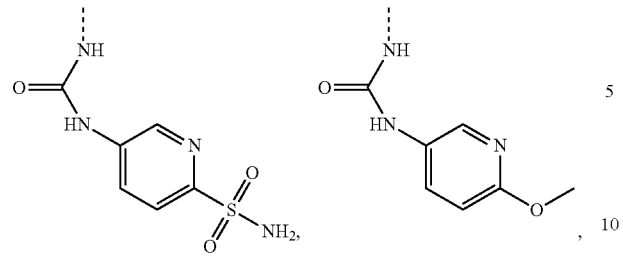
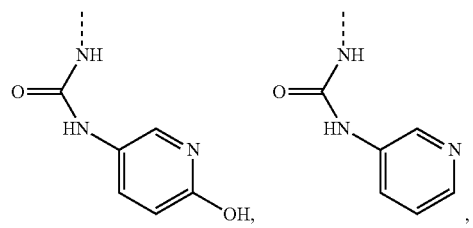
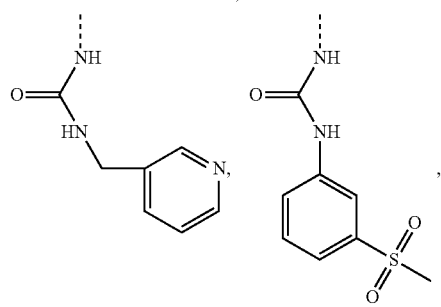
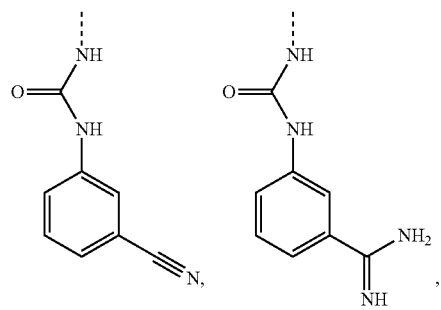
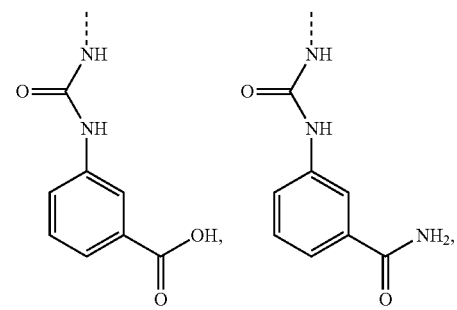
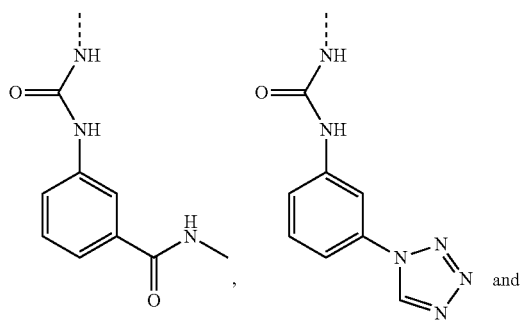
-continued
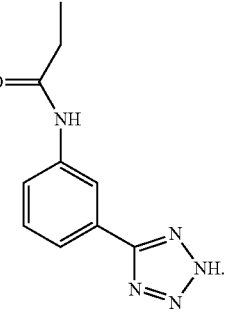
Another aspect of the invention provides compounds of formula (I) wherein the compound is of formula (Ia)
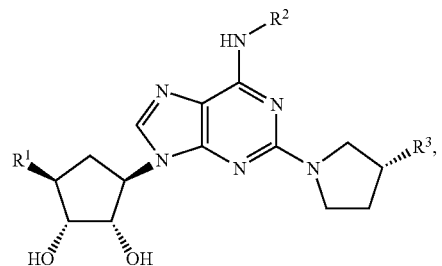
(Ia)
where
  $R^1$ is selected from
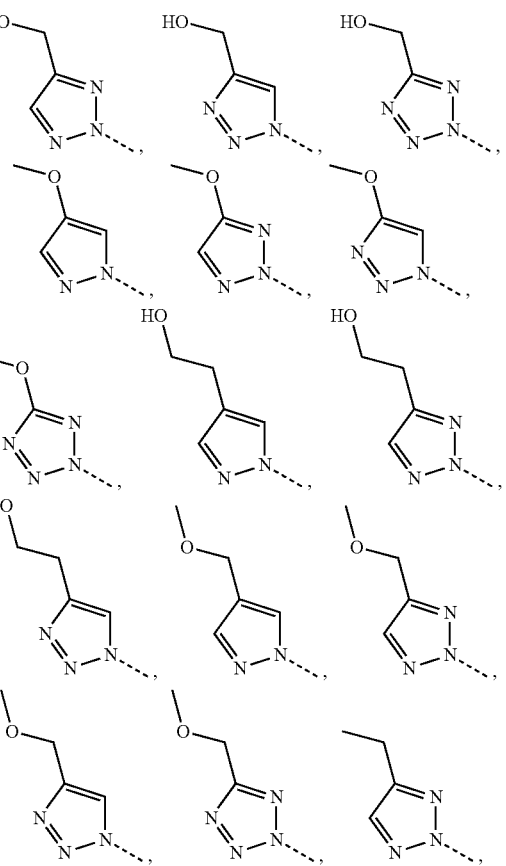

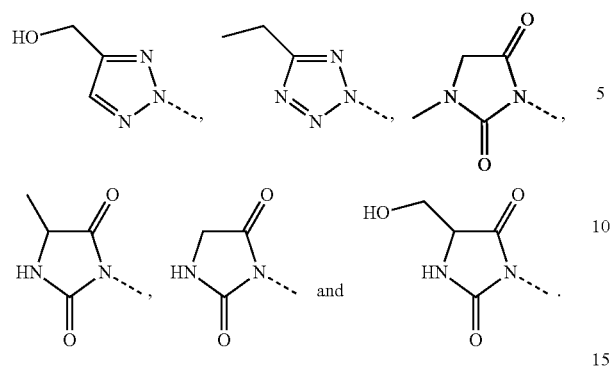
R² is selected from
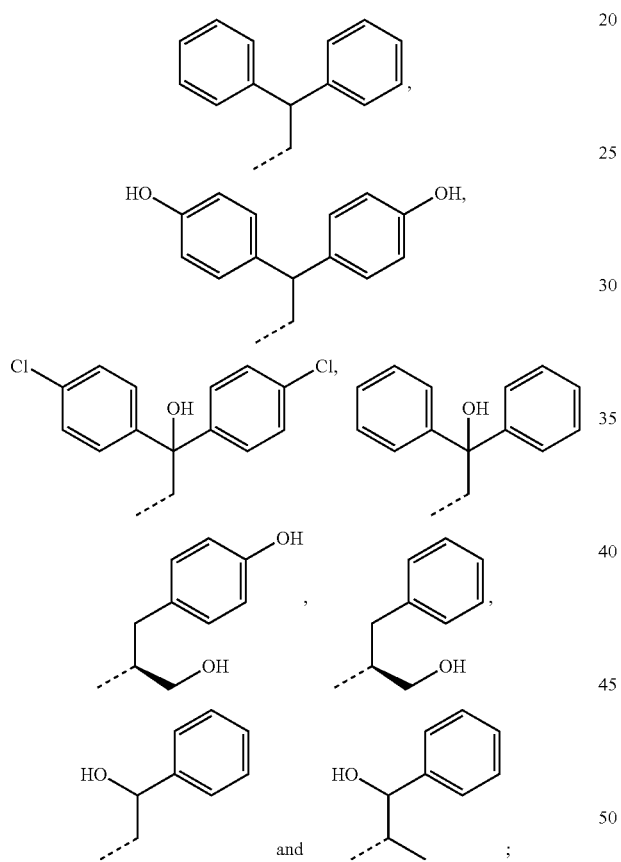
and
R³ is selected from
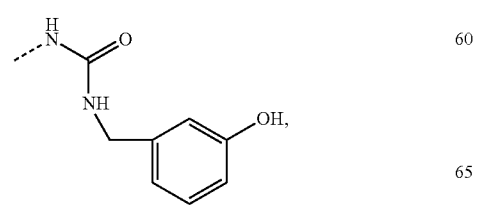
-continued
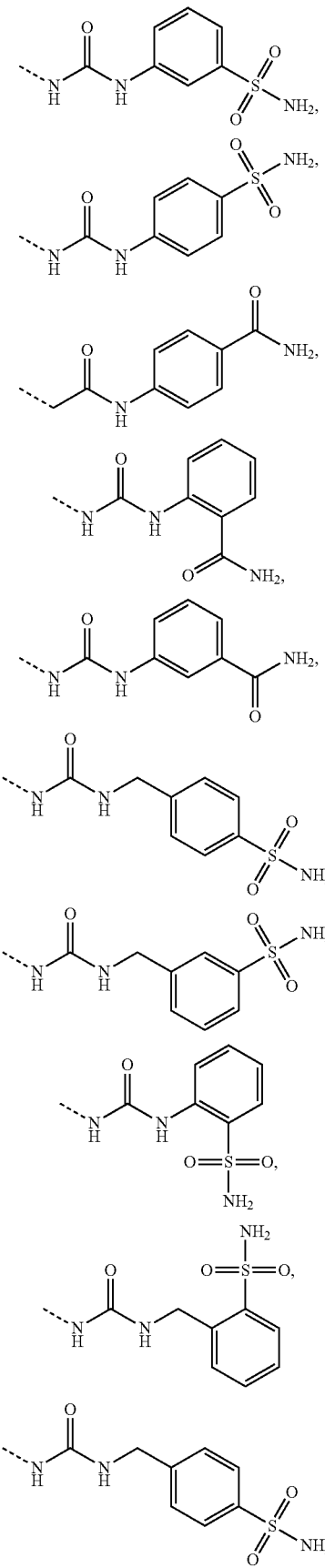

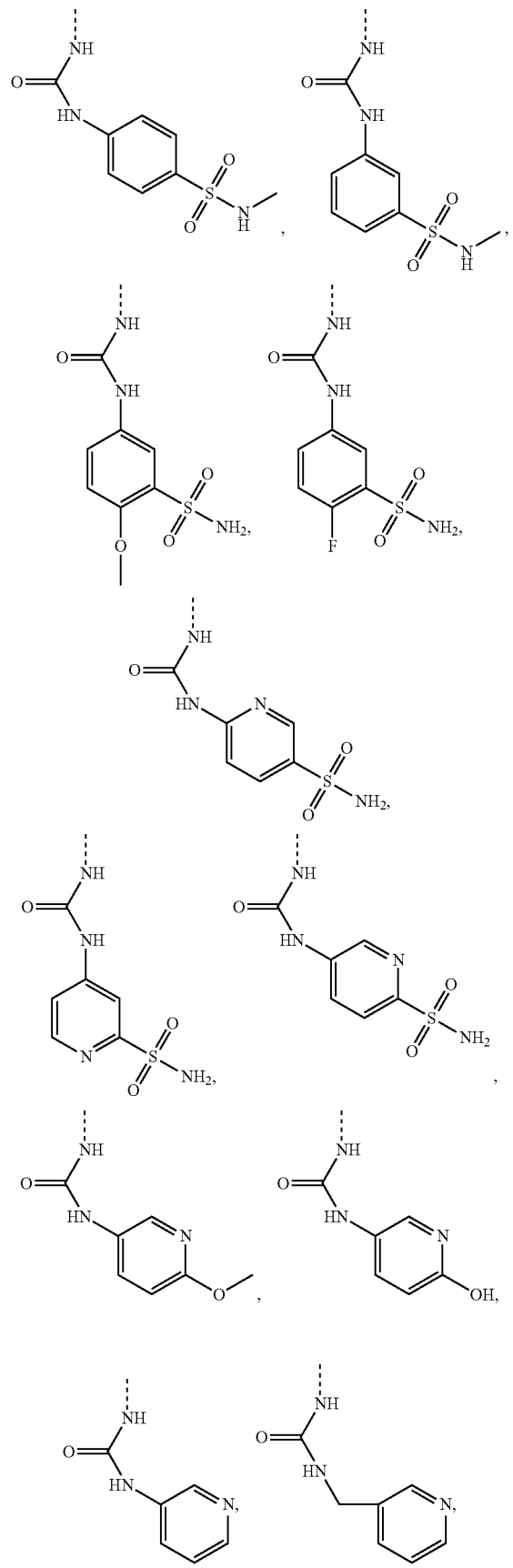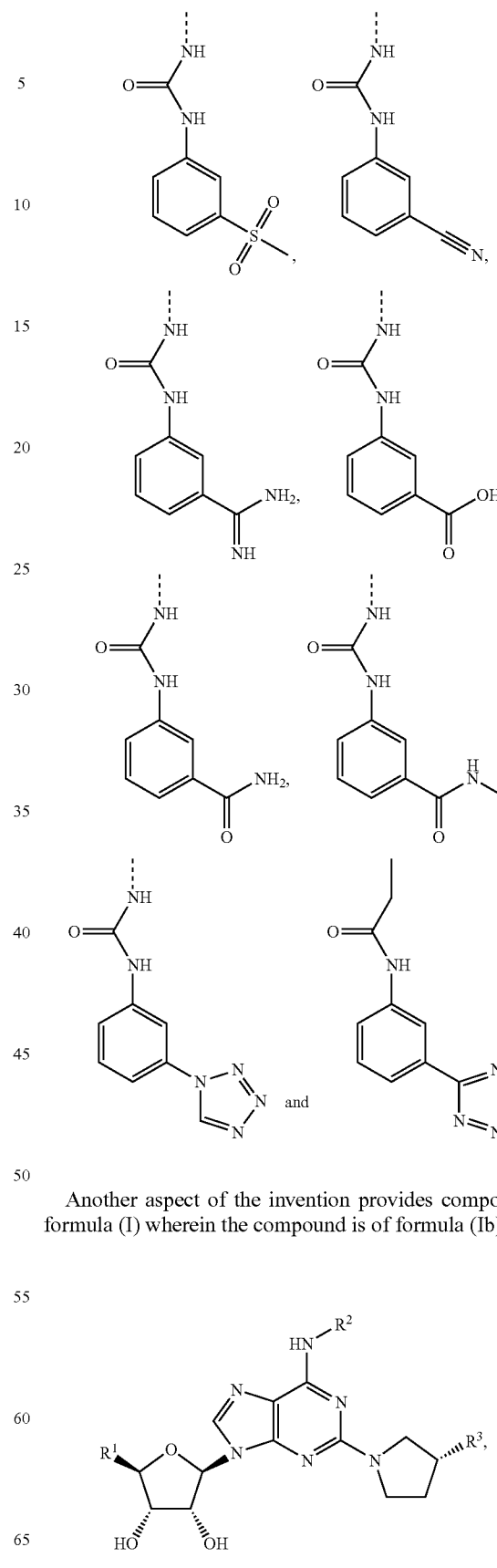
Another aspect of the invention provides compounds of formula (I) wherein the compound is of formula (Ib)

where
$R^1$ is selected from
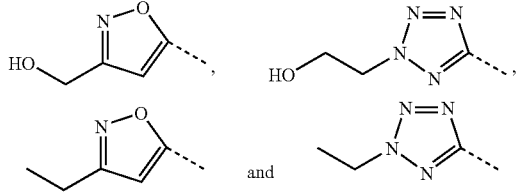
$R^2$ is selected from
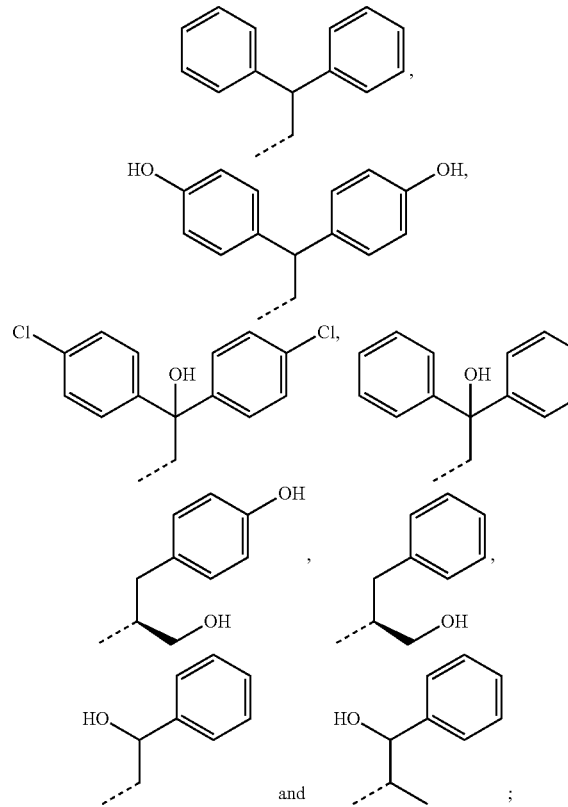
and
$R^3$ is selected from
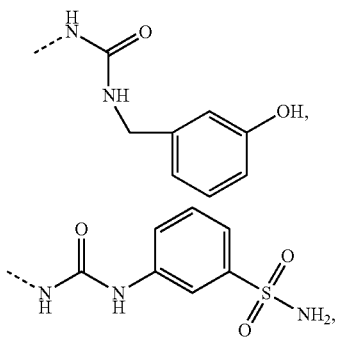
-continued
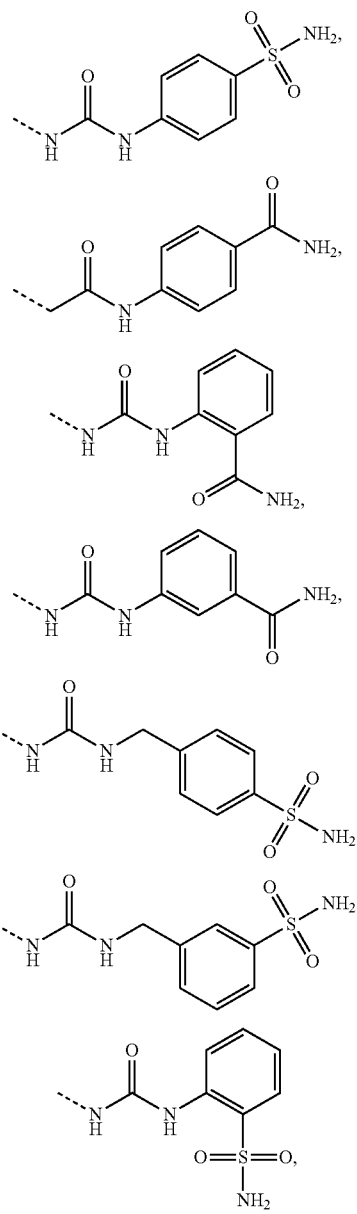
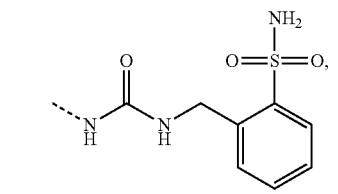

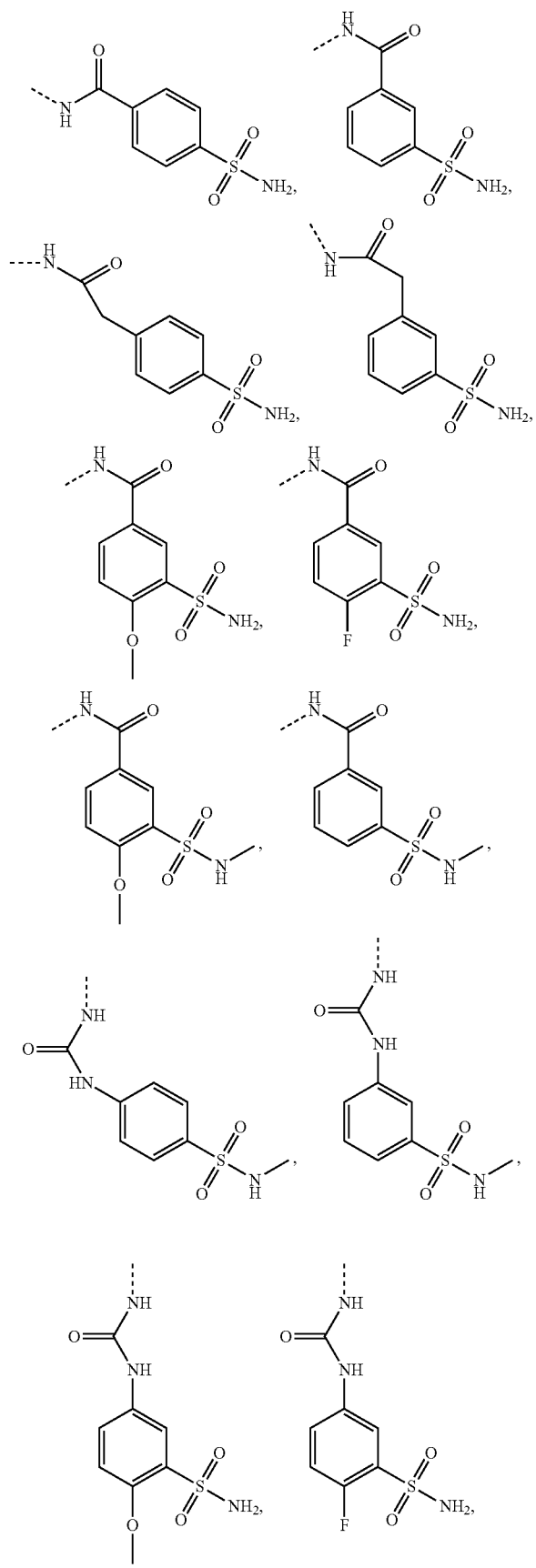
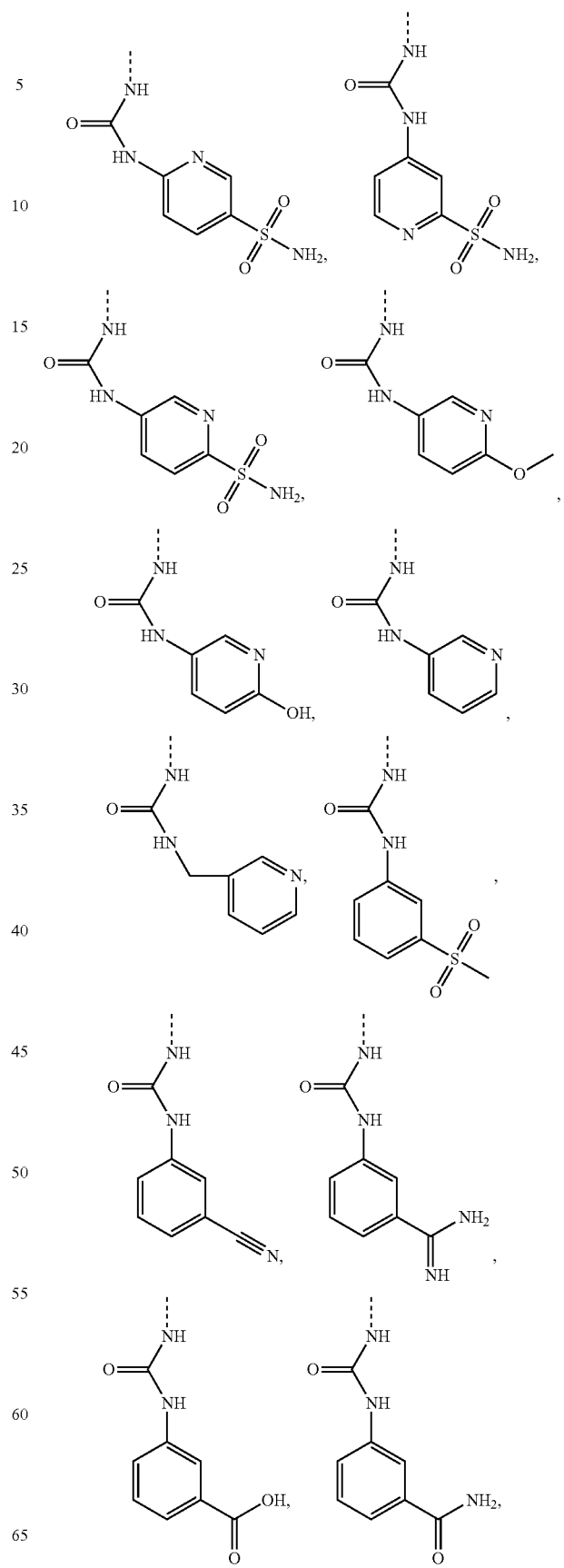

-continued

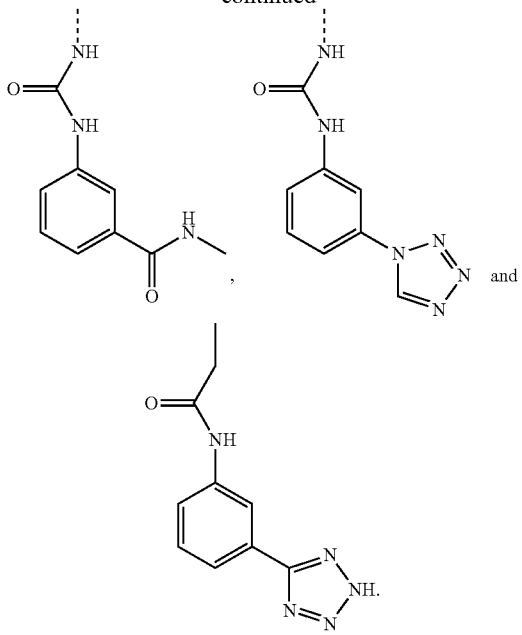

Especially preferred specific compounds of formula (I) are those described hereinafter in the Examples.

Stereoisomers are those compounds where there is an asymmetric carbon atom. The compounds exist in individual optically active isomeric forms or as mixtures thereof, e.g., as diastereomeric mixtures. The present invention embraces both individual optically active R and S isomers, as well as mixtures thereof. Individual isomers can be separated by methods well-known to those skilled in the art, e.g. chiral high performance liquid chromatography (HPLC).

Tautomers are one of two or more structural isomers that exist in equilibrium and are readily converted from one isomeric form to another.

The compounds of the invention may exist in both unsolvated and solvated forms.

The term "solvate" is used herein to describe a molecular complex comprising the compound of the invention and one or more pharmaceutically acceptable solvent molecules, e.g., ethanol. The term "hydrate" is employed when said solvent is water.

Synthesis

Another embodiment of the present invention provides a process for the preparation of compounds of formula (I) in free or pharmaceutically acceptable salt form, which comprises the steps of:
(i) reacting a compound of formula (Ic)

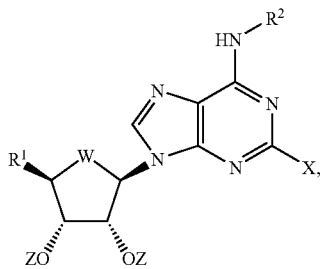
(Ic)

wherein
  $R^1$, W and $R^2$ are as defined hereinbefore;
  Z is H or a protecting group; and
  X is a leaving group,
with a compound of formula (Id)

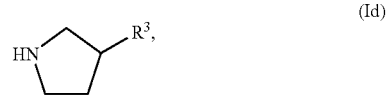
(Id)

wherein
  $R^3$ is as defined in hereinbefore; and
  removing any protecting groups and recovering the resultant compound of formula (I), in free or pharmaceutically acceptable salt form.

The compound of formula (Ic) may be prepared by reacting a compound of formula (Ie)

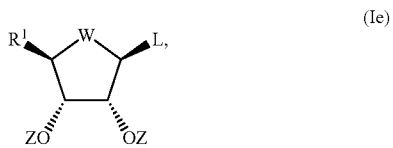
(Ie)

wherein
  $R^1$ and Z are as defined hereinbefore; and
  L represents a leaving group or a protected derivative thereof with a 2,6-dihalopurine, e.g., 2,6-dichloropurine,
to provide a compound of formula (If)

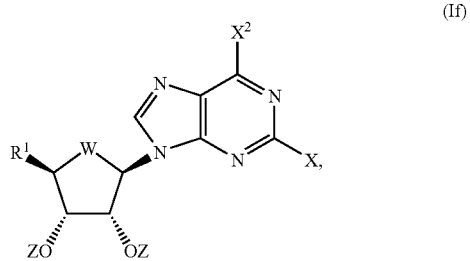
(If)

wherein
  $R^1$ and Z are defined hereinbefore; and
  X and $X^2$ are halogen.

Compound of formula (If) can be reacted with $R^2NH_2$ under conventional conditions to provide compound of formula (Ic).

The compounds of formula (I) can be prepared, e.g., using the reactions and techniques described below and in the Examples. The compounds of formula (I) can be prepared analogously to the preparations described in Applicant's patent applications PCT/EP2005/011344, GB 0500785.1, and GB 0505219.6. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula (I) into another compound of formula (I). Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry*, $5^{th}$ Edition, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995); and *Comprehensive Organic Synthesis*, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is T. W. Greene and P. G. M. Wuts, *Protective Groups In Organic Synthesis*, Wiley and Sons (1999). It is understood by those skilled in the art that only combinations of substituents that are chemically possible are embodiments of the present invention.

Compounds of formula (I) in free form may be converted into salt form, and vice versa, in a conventional manner. The compounds in free or salt form can be obtained in the form of hydrates or solvates containing a solvent used for crystallization. Compounds of formula (I) can be recovered from reaction mixtures and purified in a conventional manner. Isomers, such as stereoisomers, may be obtained in a conventional manner, e.g., by fractional crystallization or asymmetric synthesis from correspondingly asymmetrically substituted, e.g., optically active, starting materials.

Compounds of formula (I) and their pharmaceutically acceptable salts are useful as pharmaceuticals. In particular, they activate the adenosine $A_{2A}$ receptor, i.e., they act as $A_{2A}$ receptor agonists. Their properties as $A_{2A}$ agonists may be demonstrated using the method described by L. J. Murphree et al in *Mol Pharmacol*, Vol. 61, pp. 455-462 (2002).

Compounds of the Examples herein below have $K_i$ values below 1.0 µM in the above assay. For example, the compounds of Examples C1 and C2 have $K_i$ values of 0.089 µM and 0.033 µM respectively.

Having regard to their activation of the adenosine $A_{2A}$ receptor, compounds of formula (I), in free or pharmaceutically acceptable salt form, hereinafter alternately referred to as "agents of the invention", are useful in the treatment of conditions which respond to the activation of the adenosine $A_{2A}$ receptor, particularly inflammatory or allergic conditions. Treatment in accordance with the invention may be symptomatic or prophylactic.

Accordingly, agents of the invention are useful in the treatment of inflammatory or obstructive airways diseases, resulting, e.g., in reduction of tissue damage, airways inflammation, bronchial hyperreactivity, remodelling or disease progression. Inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular, other inhaled drug therapy. The invention is also applicable to the treatment of bronchitis of whatever type or genesis including, e.g., acute, arachidic, catarrhal croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis including, e.g., aluminosis, anthracosis, asbestosis, chalicosis, ptilosis, siderosis, silicosis, tabacosis and byssinosis.

Other inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., cortico-steroid) or bronchodilatory. Prophylactic benefit in asthma may, in particular, be apparent in subjects prone to "morning dipping". "Morning dipping" is a recognized asthmatic syndrome, common to a substantial percentage of asthmatics and characterized by asthma attack, e.g., between the hours of about 4 to 6 am, i.e. at a time normally substantially distant from any previously administered symptomatic asthma therapy.

Having regard to their anti-inflammatory activity, in particular, in relation to inhibition of eosinophil activation, agents of the invention are also useful in the treatment of eosinophil related disorders, e.g., eosinophilia, in particular, eosinophil-related disorders of the airways (e.g., involving morbid eosinophilic infiltration of pulmonary tissues) including hypereosinophilia as it effects the airways and/or lungs, as well as, e.g., eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, e.g., psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular, diseases or conditions having an inflammatory component, e.g., treatment of diseases and conditions of the eye, such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g., haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g., ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunct-ivitis sicca and vernal keratoconjunctivitis, interstitial lung fibrosis, psoriatic arthritis and glomerulonephritis (with and without nephrotic syndrome, e.g., including idiopathic nephrotic syndrome or minal change nephropathy).

Further, agents of the invention may also be used for the treatment of cystic fibrosis, pulmonary hypertension, pulmonary fibrosis, inflammatory bowel syndrome, wound healing, diabetic nephropathy as described in WO 05/107463, reduction of inflammation in transplanted tissue as described in US 2005/182018, inflammatory diseases caused by pathogenic organisms as described in WO 03/086408, and cardiovascular conditions as described in WO 03/029264.

Also, the agents of the invention may be used to assess the severity of coronary artery stenosis as described in WO 00/078774 and useful in conjunction with radioactive imaging agents to image coronary activity and useful in adjunctive therapy with angioplasty as described in WO 00/78779.

Agents of the invention are also useful in combination with a protease inhibitor for prevention of organ ischemia and reperfusion injury as described in WO 05/003150, and in combination with an integrin antagonist for treating platelet aggregation as described in WO 03/090733.

Agents of the invention are also useful in promoting wound healing in bronchial epithelial cells as described in *AJP-Lung*, Vol. 290, pp. 849-855.

Other diseases or conditions which may be treated with agents of the invention include diabetes, e.g., diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, conditions characterised by elevated intraocular pressure or secretion of ocular aqueous humor, such as glaucoma, ischemic tissue/organ damage from reperfusion and bedsores.

The effectiveness of an agent of the invention in inhibiting inflammatory conditions, for example in inflammatory airways diseases, may be demonstrated in an animal model, e.g., a mouse or rat model, of airways inflammation or other inflammatory conditions, e.g., as described by Szarka et al, *J Immunol Methods*, Vol. 202, pp. 49-57 (1997); Renzi et al, *Am Rev Respir Dis*, Vol. 148, pp. 932-939 (1993); Tsuyuki et al., *J Clin Invest*, Vol. 96, pp. 2924-2931 (1995) Cernadas et al., *Am J Respir Cell Mol Biol*, Vol. 20, pp. 1-8 (1999); and Fozard et al *Eur J Pharmacol*, Vol. 438, pp. 183-188 (2002).

The agents of the invention are also useful as co-therapeutic agents for use in combination with other drug substances such as anti-inflammatory, bronchodilatory, antihistamine or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneoudy with or after the other drug substance.

Accordingly the invention includes a combination of an agent of the invention as hereinbefore described with an anti-inflammatory, bronchodilatory, antihistamine or anti-tussive drug substance, said agent of the invention and said drug substance being in the same or different pharmaceutical composition.

Suitable anti-inflammatory drugs include steroids, in particular, glucocorticosteroids such as budesonide, beclamethasone dipropionate, fluticasone propionate, cidesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonsts, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTB4 antagonists, such as BIIL 284, CP-195543, DPC11870, LTB4 ethanolamide, LY 293111, LY 255283, CGS025019C, CP-195543, ONO-4057, SB 209247, SC-63228 and those described in U.S. Pat. No. 5,451,700; LTD4 antagonists include montelukast, pranlukast, zafirlukast, accolate, SR2640, Wy-48,252, ICI-198615, MK-571, LY-171883, Ro 24-5913 and L-648051; PDE4 inhibitors such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12.281 (Asta Medica), CDC-801 (Celgene), SelCID™ CC-10004 (Celgene), VM554/UM565 (Vernalis), T-440 (Tanabe), KW-4490 (Kyowa Hakko Kogyo) and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449. WO 04/018450. WO 04/018451, WO 04/018457, WO 04/018465, WO 04/019944, WO 04/019945, WO 04/045607 and WO 04/037805; adenosine $A_{2B}$ receptor antagonists, such as those described in WO 02/42298; and beta-2 adrenoceptor agonists, such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula (I) of WO 0075114, which document is incorporated herein by reference, preferably compounds of the Examples thereof, especially a compound of formula

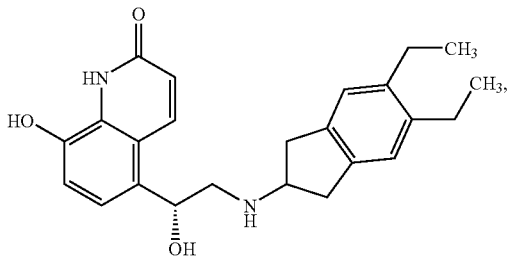

and pharmaceutically acceptable salts thereof, as well as compounds (in free or salt or solvate form) of formula (I) of WO 04/16601, and also compounds of EP 1440966, JP 05025045, WO 93/18007, WO 99/64035, US 2002/0055651, US 2005/0133417, US 2005/5159448, WO 01/42193, WO 01/83462, WO 02/66422, WO 02/70490, WO 02/76933, WO 03/24439, WO 03/42160, WO 03/42164, WO 03/72539, WO 03/91204. WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, EP1460064, WO 04/087142, WO 04/089892, EP 01477167, US 2004/0242622, US 2004/0229904, WO 04/108675, WO 04/108676, WO 05/033121, WO 05/040103, WO 05/044787, WO 05/058867, WO 05/065650, WO 05/066140 and WO 05/07908.

Suitable bronchodilatory drugs include anticholinergic or antimuscarinic agents, in particular, ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, US 2005/171147. US 2005/182091, WO 01/04118, WO 02/00652, WO 02/51841, WO 02/53564, WO 03/00840, WO 03/33495, WO 03/53966, WO 03/87094, WO 04/018422, WO 04/05285 and WO 05/077361.

Suitable dual anti-inflammatory and bronchodilatory drugs include dual beta-2 adrenoceptor agonist/muscarinic antagonists such as those disclosed in US 2004/0167167, US 2004/0242622, US 2005/182092, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

Other useful combinations of agents of the invention with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D, Takeda antagonists, such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-amin-ium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

In accordance with the foregoing, the invention also provides a method for the treatment of a condition responsive to activation of the adenosine $A_{2A}$ receptor, e.g., an inflammatory or allergic condition, particularly an inflammatory or obstructive airways disease, which comprises administering to a subject, particularly a human subject, in need thereof a compound of formula (I) in free form or in the form of a pharmaceutically acceptable salt. In another aspect the invention provides a compound of formula (I), in free form or in the form of a pharmaceutically acceptable salt, for use in the manufacture of a medicament for the treatment of a condition responsive to activation of the adenosine $A_{2A}$ receptor, particularly an inflammatory or obstructive airways disease.

The agents of the invention may be administered by any appropriate route, e.g., orally, e.g., in the form of a tablet or capsule; parenterally, e.g., intravenously; by inhalation, e.g., in the treatment of inflammatory or obstructive airways disease; intranasally, e.g., in the treatment of allergic rhinitis; topically to the skin, e.g., in the treatment of atopic dermatitis; or rectally, e.g., in the treatment of inflammatory bowel disease.

In a further aspect, the invention also provides a pharmaceutical composition comprising a compounds of formula (I) in free form or in the form of a pharmaceutically acceptable salt, optionally together with a pharmaceutically acceptable diluent or carrier therefor. The composition may contain a co-therapeutic agent, such as an anti-inflammatory, bronchodilatory, antihistamine or anti-tussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations.

When the composition comprises an aerosol formulation, it preferably contains, e.g., a hydro-fluoro-alkane (HFA) propellant such as HFA134a or HFA227 or a mixture of these, and may contain one or more co-solvents known in the art, such as ethanol (up to 20% by weight), and/or one or more surfactants, such as oleic acid or sorbitan trioleate, and/or one or more bulking agents, such as lactose. When the composition comprises a dry powder formulation, it preferably contains, e.g., the compounds of formula (I) having a particle diameter up to 10 microns, optionally together with a diluent or carrier, such as lactose, of the desired particle size distribution and a compound that helps to protect against product performance deterioration due to moisture, e.g., magnesium stearate. When the composition comprises a nebulised formulation, it preferably contains, e.g., the compound of formula (I) either dissolved, or suspended, in a vehicle containing water, a co-solvent, such as ethanol or propylene glycol and a stabilizer, which may be a surfactant.

The invention includes:

(a) a compounds of formula (I) in inhalable form, e.g., in an aerosol or other atomisable composition or in inhalable particulate, e.g., micronized, form;

(b) an inhalable medicament comprising a compounds of formula (I) in inhalable form;

(c) a pharmaceutical product comprising a compounds of formula (I) in inhalable form in association with an inhalation device; and (d) an inhalation device containing a compounds of formula (I) in inhalable form.

Dosages of compounds of formula (I) employed in practicing the present invention will of course vary depending, e.g., on the particular condition to be treated, the effect desired and the mode of administration. In general, suitable daily dosages for administration by inhalation are of the order of 0.005-10 mg, while for oral administration suitable daily doses are of the order of 0.05-100 mg.

The invention is illustrated by the following Examples.

EXAMPLES

Examples 1-48

Compounds of formula I

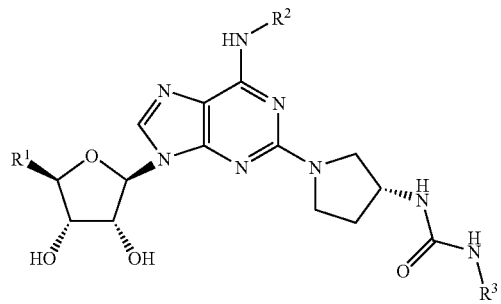

are shown in the following table. Methods for preparing such compounds are described hereinafter.

| Ex. | Structure | R¹ | R² | R³ | Name |
|---|---|---|---|---|---|
| 1 | 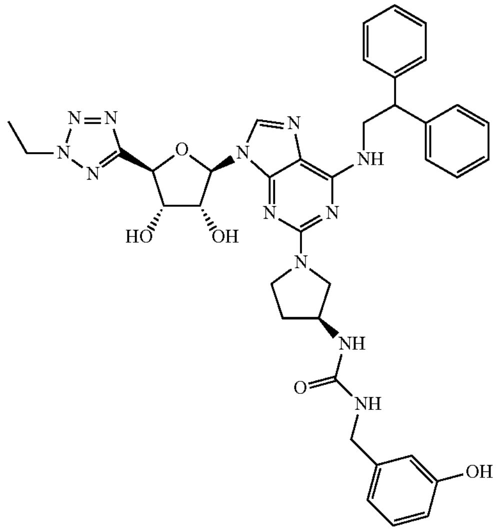 | 2-ethyl-2H-tetrazol-5-yl | 2,2-diphenylethyl | 3-hydroxybenzyl | 1-((R)-1-{6-(2,2-Diphenyl-ethylamino)-9-(2R,3R,4S,5R)-5-(2-ethyl-2H-tetrazol-5-yl)-3,4-dihydroxy-tetrahydrofuran-2-yl]-9H-purin-2-yl]-pyrrolidin-3-yl)-3-(3-hydroxy-benzyl)-urea |
| 2 | 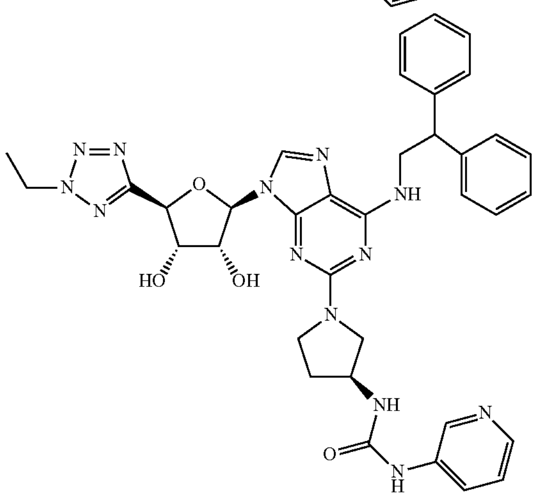 | 2-ethyl-2H-tetrazol-5-yl | 2,2-diphenylethyl | pyridin-3-yl | 1-((R)-1-{6-(2,2-Diphenyl-ethylamino)-9-[(2R,3R,4S,5R)-5-(2-ethyl-2H-tetrazol-5-yl)-3,4-dihydroxy-tetrahydrofuran-2-yl]-9H-purin-2-yl]-pyrrolidin-3-yl)-3-pyridin-3-yl-urea |

-continued

| Ex. | Structure | R¹ | R² | R³ | Name |
|---|---|---|---|---|---|
| 3 | 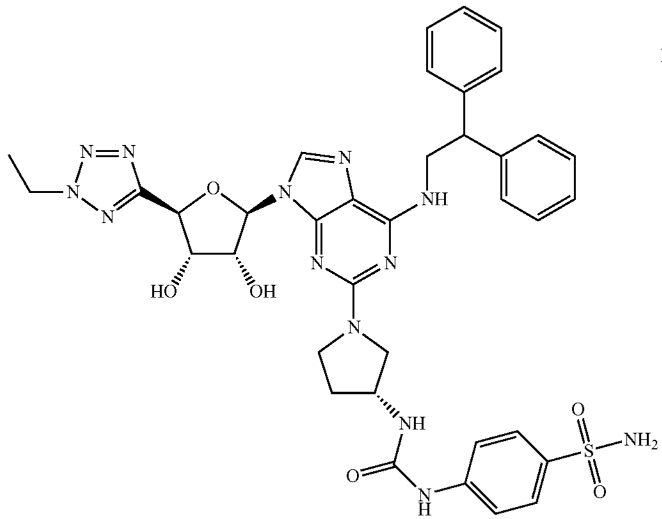 | | | | 4-[3-((R)-1-{6-(2,2-Diphenyl-ethylamino)-9-[(2R,3R,4S,5R)-5-(2-ethyl-2H-tetrazol-5-yl)-3,4-dihydroxy-tetrahydrofuran-2-yl]-9H-purin-2-yl}-pyrrolidin-3-yl)-ureido]-benzenesulfonamide |
| 4 | 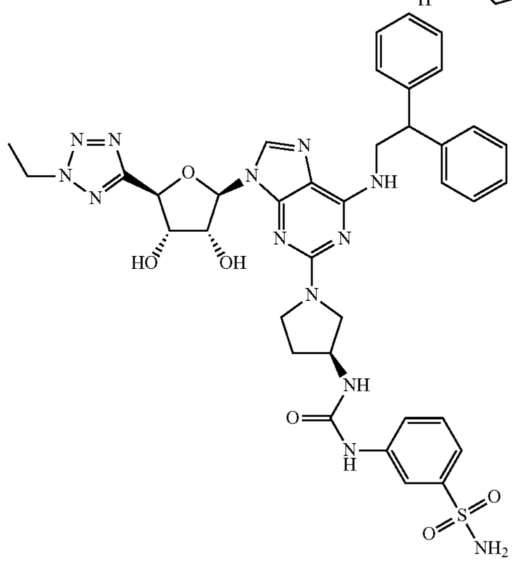 | | | | 3-[3-((R)-1-{6-(2,2-Diphenyl-ethylamino)-9-[(2R,3R,4S,5R)-5-(2-ethyl-2H-tetrazol-5-yl)-3,4-dihydroxy-tetrahydro-furan-2-yl]-9H-purin-2-yl}-pyrrolidin-3-yl)-ureido]-benzenesulfonamide |

-continued

| Ex. | Structure | R¹ | R² | R³ | Name |
|---|---|---|---|---|---|
| 5 | 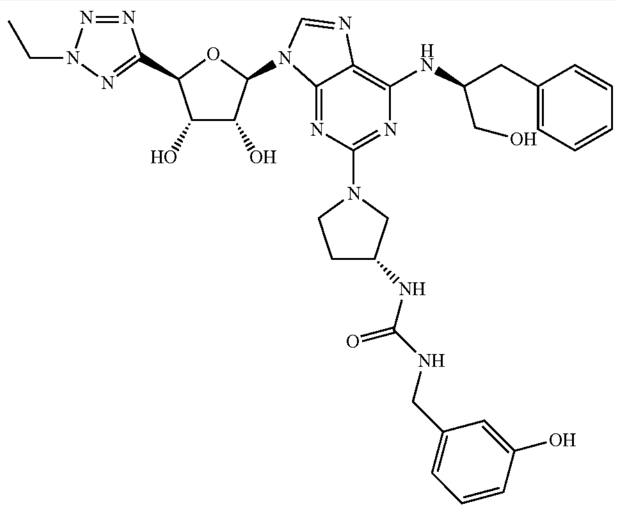 | | | | 1-{(R)-[9-(2R,3R,4S,5R)-5-(2-Ethyl-2H-tetrazol-5-yl)-3,4-dihydroxy-tetrahydro-furan-2-yl]-6-((S)-1-hydroxymethyl-2-phenyl-ethylamino)-9H-purin-2-yl]-pyrrolidin-3-yl}-3-(3-hydroxy-benzyl)-urea |
| 6 | 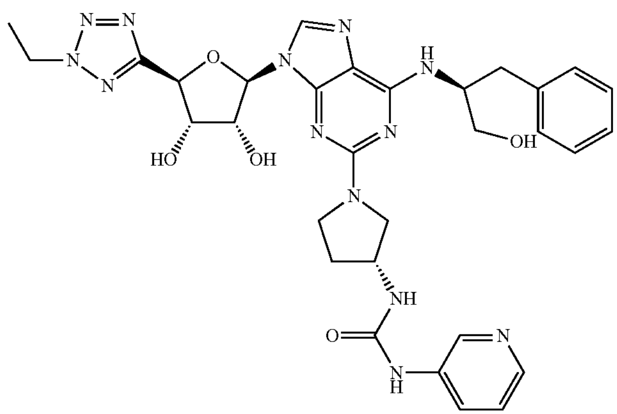 | | | | 1-{(R)-[9-(2R,3R,4S,5R)-5-(2-Ethyl-2H-tetrazol-5-yl)-3,4-dihydroxy-tetrahydro-furan-2-yl]-6-((S)-1-hydroxymethyl-2-phenyl-ethylamino)-9H-purin-2-yl]-pyrrolidin-3-yl}-3-pyridin-3-yl-urea |

| Ex. | Structure | R¹ | R² | R³ | Name |
|---|---|---|---|---|---|
| 7 | 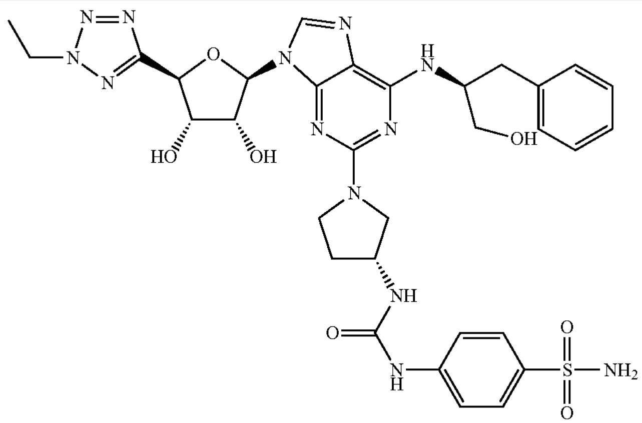 | | | | 4-(3-{(R)-1-[9-[(2R,3R,4S,5R)-5-(2-Ethyl-2H-tetrazol-5-yl)-3,4-dihydroxy-tetrahydro-furan-2-yl]-6-((S)-1-hydroxymethyl-2-phenyl-ethylamino)-9H-purin-2-yl]-pyrrolidin-3-yl}-ureido)-benzenesulfonamide |
| 8 | 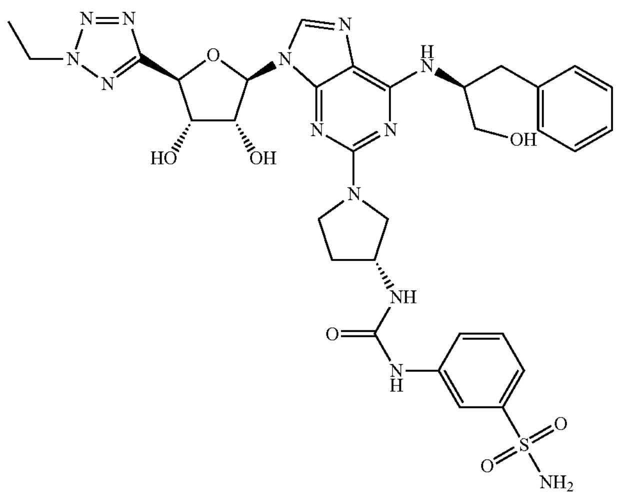 | | | | 3-(3-{(R)-1-[9-[(2R,3R,4S,5R)-5-(2-Ethyl-2H-tetrazol-5-yl)-3,4-dihydroxy-tetrahydro-furan-2-yl]-6-((S)-1-ydroxymethyl-2-phenyl-ethylamino)-9H-purin-2-yl]-pyrrolidin-3-yl}-ureido)-benzenesulfonamide |

-continued

| Ex. | Structure | R¹ | R² | R³ | Name |
|---|---|---|---|---|---|
| 9 | 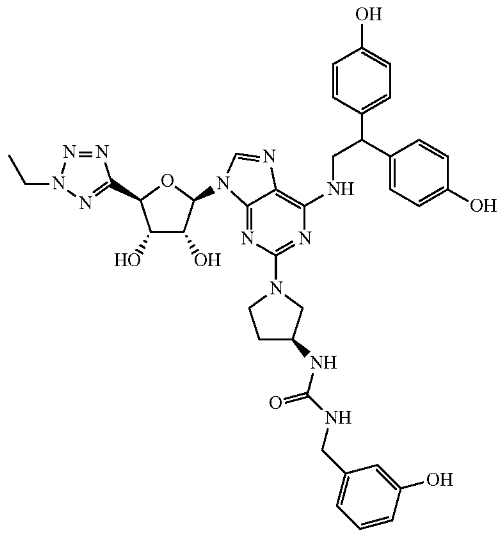 | 2-ethyl-5-methyl-2H-tetrazol-5-yl | 2,2-bis(4-hydroxyphenyl)ethyl | 3-hydroxybenzyl | 1-((R)-1-{6-[2,2-Bis-(4-hydroxy-phenyl)-ethylamino]-9-[(2R,3R,4S,5R)-5-(2-ethyl-2H-tetrazol-5-yl)-3,4-dihydroxy-tetrahydro-furan-2-yl]-9H-purin-2-yl}-pyrrolidin-3-yl)-3-(3-hydroxy-benzyl)-urea |
| 10 | 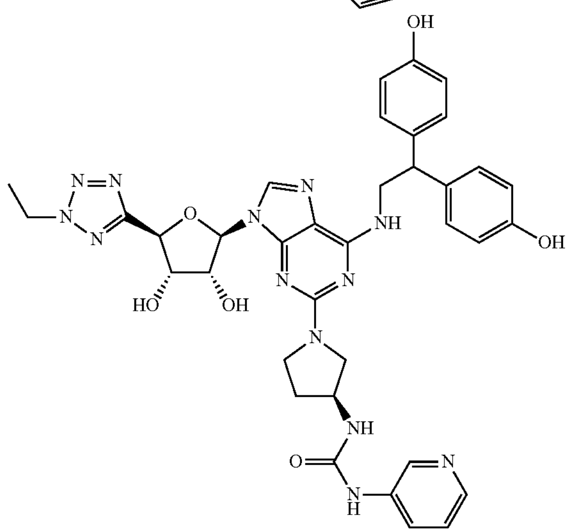 | 2-ethyl-5-methyl-2H-tetrazol-5-yl | 2,2-bis(4-hydroxyphenyl)ethyl | pyridin-3-yl | 1-((R)-1-{6-[2,2-Bis-(4-hydroxy-phenyl)-9-[(2R,3R,4S,5R)-5-(2-ethyl-2H-tetrazol-5-yl)-3,4-dihydroxy-tetrahydro-furan-2-yl]-9H-purin-2-yl]-pyrrolidin-3-yl)-3-pyridin-3-yl-urea |

-continued

| Ex. | Structure | R¹ | R² | R³ | Name |
|---|---|---|---|---|---|
| 11 | (structure shown) | 2-ethyl-5-methyl-2H-tetrazol-5-yl with H₃C-CH₂- | 1,1-bis(4-hydroxyphenyl)propyl | 4-SO₂NH₂-phenyl | 4-[3-((R)-1-{6-[2,2-Bis-(4-hydroxyphenyl)-ethylamino]-9-[(2R,3R,4S,5R)-5-(2-ethyl-2H-tetrazol-5-yl)-3,4-dihydroxy-tetrahydro-furan-2-yl]-9H-purin-2-yl]-pyrrolidin-3-yl)-ureido]-benzenesulfonamide |
| 12 | (structure shown) | 2-ethyl-5-methyl-2H-tetrazol-5-yl with H₃C-CH₂- | 1,1-bis(4-hydroxyphenyl)propyl | 3-SO₂NH₂-phenyl | 3-[3-((R)-1-{6-[2,2-Bis-(4-hydroxyphenyl)-ethylamino]-9-[(2R,3R,4S,5R)-5-(2-ethyl-2H-tetrazol-5-yl)-3,4-dihydroxy-tetrahydro-furan-2-yl]-9H-purin-2-yl]-pyrrolidin-3-yl)-ureido]-benzenesulfonamide |

| Ex. | Structure | R¹ | R² | R³ | Name |
|---|---|---|---|---|---|
| 13 | 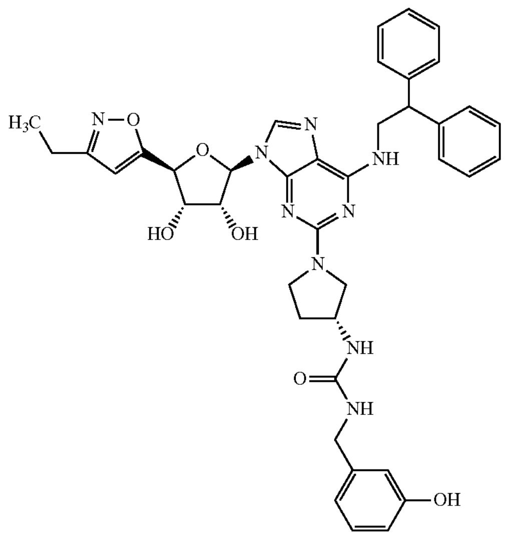 | 5-methyl-3-(methyl)isoxazole (H₃C-CH₂- attached to isoxazole) | 1,1-diphenylpropyl (CHPh₂CH₂-) | 3-hydroxybenzyl | 1-((R)-1-{6-(2,2-Diphenyl-ethylamino)-9-[(2R,3R,4S,5S)-5-(3-ethyl-isoxazol-5-yl)-3,4-dihydroxy-tetrahydro-furan-2-yl]-9H-purin-2-yl]-pyrrolidin-3-yl)-3-(3-hydroxy-benzyl)-urea |
| 14 | 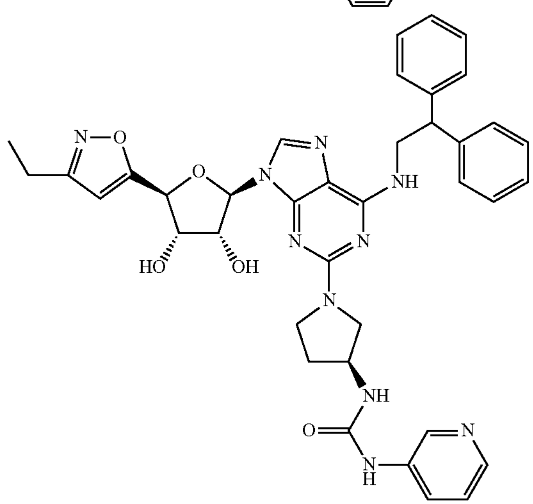 | 5-methyl-3-(methyl)isoxazole | 1,1-diphenylpropyl | pyridin-3-yl | 1-((R)-1-{6-(2,2-Diphenyl-ethylamino)-9-[(2R,3R,4S,5S)-5-(3-ethyl-isoxazol-5-yl)-3,4-dihydroxy-tetrahydro-furan-2-yl]-9H-purin-2-yl]-pyrrolidin-3-yl)-3-pyridin-3-yl-urea |

-continued

| Ex. | Structure | R¹ | R² | R³ | Name |
|---|---|---|---|---|---|
| 15 | 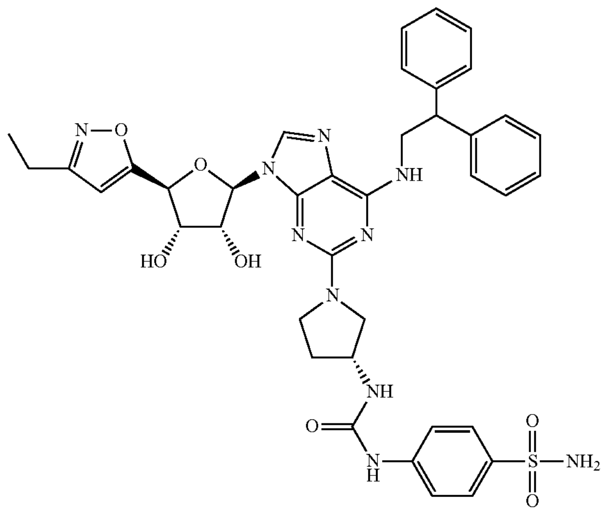 | 5-ethyl-3-methylisoxazole-CH₂- | 2,2-diphenylethyl | 4-SO₂NH₂-phenyl | 4-[3-((R)-1-{6-(2,2-Diphenyl-ethylamino)-9-[(2R,3R,4S,5S)-5-(3-ethyl-isoxazol-5-yl)-3,4-dihydroxy-tetrahydro-furan-2-yl]-9H-purin-2-yl]-pyrrolidin-3-yl}-ureido]-benzenesulfonamide |
| 16 | 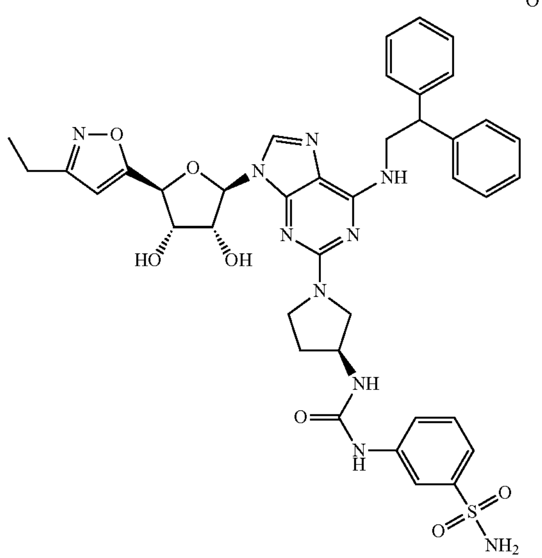 | 5-ethyl-3-methylisoxazole-CH₂- | 2,2-diphenylethyl | 3-SO₂NH₂-phenyl | 3-[3-((R)-1-{6-(2,2-Diphenyl-ethylamino)-9-[(2R,3R,4S,5S)-5-(3-ethyl-isoxazol-5-yl)-3,4-dihydroxy-tetrahydro-furan-2-yl]-9H-purin-2-yl]-pyrrolidin-3-yl}-ureido]-benzenesulfonamide |

| Ex. | Structure | R¹ | R² | R³ | Name |
|---|---|---|---|---|---|
| 17 | 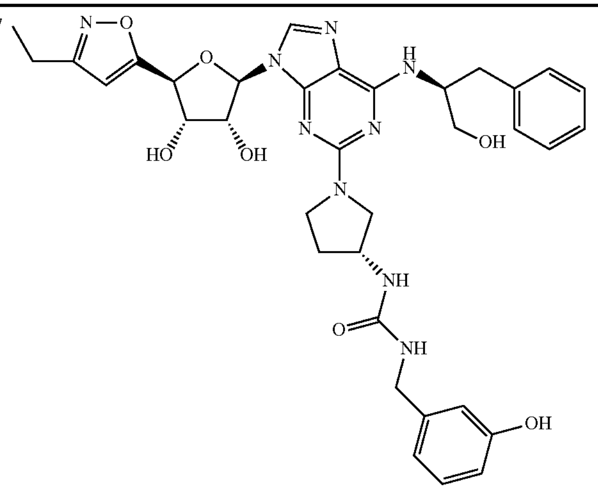 | 3-ethyl-isoxazol-5-yl with CH₃ | (S)-2-methyl-3-phenylpropan-1-ol | 3-hydroxy-5-ethylphenyl (benzyl with OH and ethyl) | 1-[(R)-1-[9-[(2R,3R,4S,5S)-5-(3-Ethyl-isoxazol-5-yl)-3,4-dihydroxy-tetrahydro-furan-2-yl]-6-((S)-1-hydroxymethyl-2-phenyl-ethylamino)-9H-purin-2-yl]-pyrrolidin-3-yl]-3-(3-hydroxy-benzyl)-urea |
| 18 | 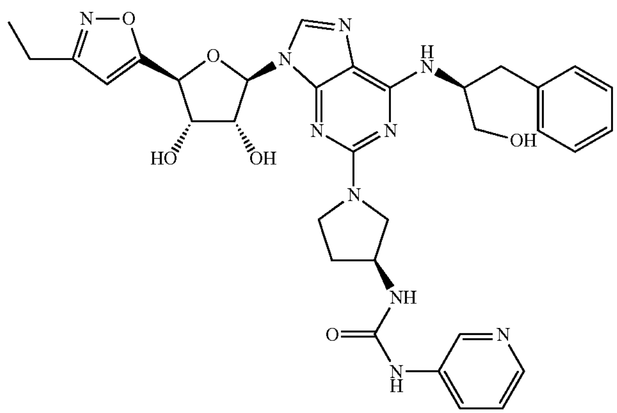 | 3-ethyl-isoxazol-5-yl with CH₃ | (S)-2-methyl-3-phenylpropan-1-ol | pyridin-3-yl | 1-[(R)-1-[9-[(2R,3R,4S,5S)-5-(3-Ethyl-isoxazol-5-yl)-3,4-dihydroxy-tetrahydro-furan-2-yl]-6-((S)-1-hydroxymethyl-2-phenyl-ethylamino)-9H-purin-2-yl]-pyrrolidin-3-yl]-3-pyridin-3-yl-urea |

| Ex. | Structure | R¹ | R² | R³ | Name |
|---|---|---|---|---|---|
| 19 | 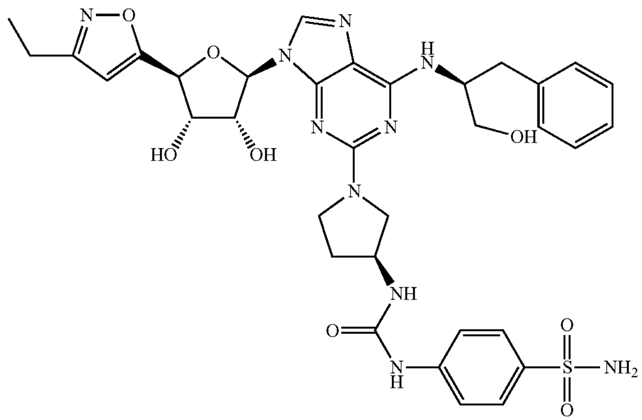 | | | | 4-(3-{(R)-1-[9-[(2R,3R,4S,5S)-5-(3-Ethyl-isoxazol-5-yl)-3,4-dihydroxy-tetrahydro-furan-2-yl]-6-((S)-1-hydroxymethyl-2-phenyl-ethylamino)-9H-purin-2-yl]-pyrrolidin-3-yl]-ureido)-benzensulfonamide |
| 20 | 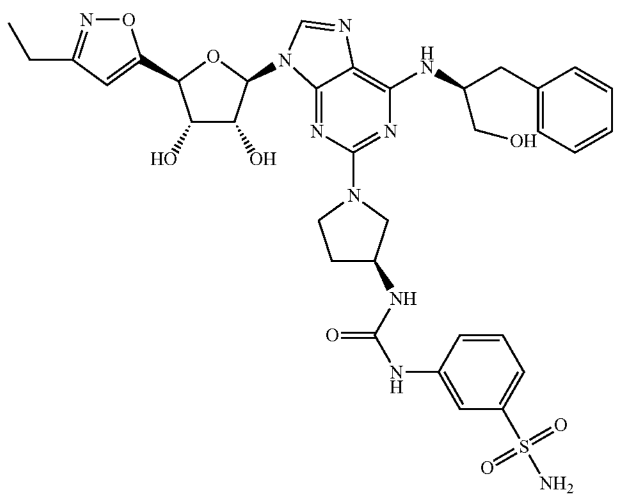 | | | | 3-(3-{(R)-1-[9-[(2R,3R,4S,5S)-5-(3-Ethyl-isoxazol-5-yl)-3,4-dihydroxy-tetrahydro-furan-2-yl]-6-((S)-1-hydroxymethyl-2-phenyl-ethylamino)-9H-purin-2-yl]-pyrrolidin-3-yl]-ureido)-benzensulfonamide |

-continued

| Ex. | Structure | R¹ | R² | R³ | Name |
|---|---|---|---|---|---|
| 21 | 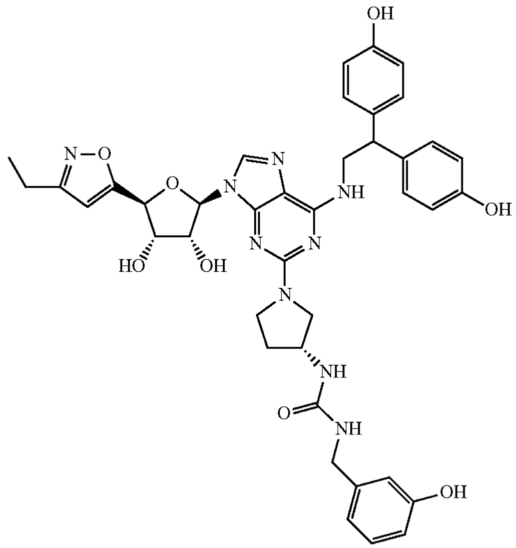 | 3-ethyl-5-methylisoxazole-CH₂- | 1,1-bis(4-hydroxyphenyl)propyl | 3-hydroxybenzyl | 1-((R)-1-{6-[2,2-Bis-(4-hydroxy-phenyl)-ethylamino]-9-[(2R,3R,4S,5S)-5-(3-ethyl-isoxazol-5-yl)-3,4-dihydroxy-tetrahydro-furan-2-yl]-9H-purin-2-yl}-pyrrolidin-3-yl)-3-(3-hydroxy-benzyl)-urea |
| 22 | 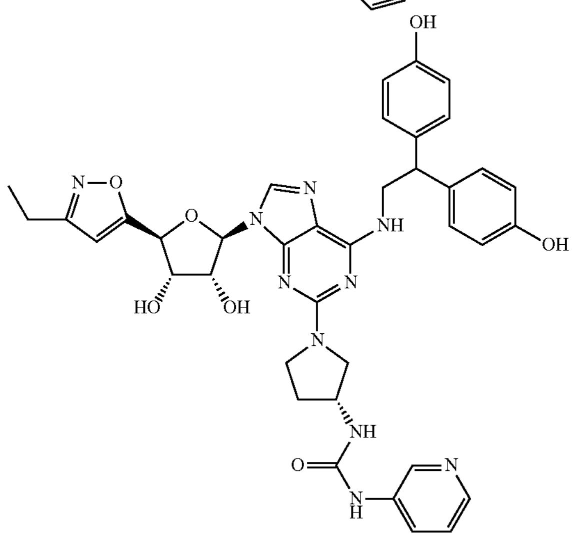 | 3-ethyl-5-methylisoxazole-CH₂- | 1,1-bis(4-hydroxyphenyl)propyl | pyridin-3-yl | 1-((R)-1-{6-[2,2-Bis-(4-hydroxy-phenyl)-ethylamino]-9-[(2R,3R,4S,5S)-5-(3-ethyl-isoxazol-5-yl)-3,4-dihydroxy-tetrahydro-furan-2-yl]-9H-purin-2-yl]-pyrrdidin-3-yl)-3-pyridin-3-yl-urea |

-continued

| Ex. | Structure | R¹ | R² | R³ | Name |
|---|---|---|---|---|---|
| 23 | 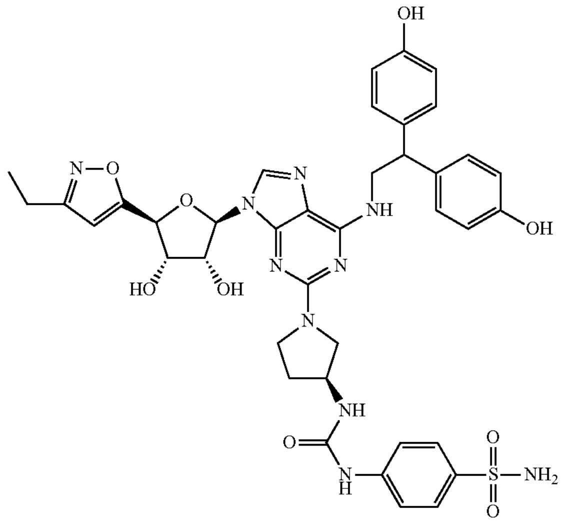 | 5-methyl-3-ethyl-isoxazole | 1,1-bis(4-hydroxyphenyl)propyl | 4-sulfamoylphenyl | 4-[3-((R)-1-{6-[2,2-Bis-(4-hydroxyphenyl)-ethylamino]-9-[(2R,3R,4S,5S)-5-(3-ethyl-isoxazol-5-yl)-3,4-dihydroxy-tetrahydro-furan-2-yl]-9H-purin-2-yl]-pyrrolidin-3-yl)-ureido]-benzenesulfonamide |
| 24 | 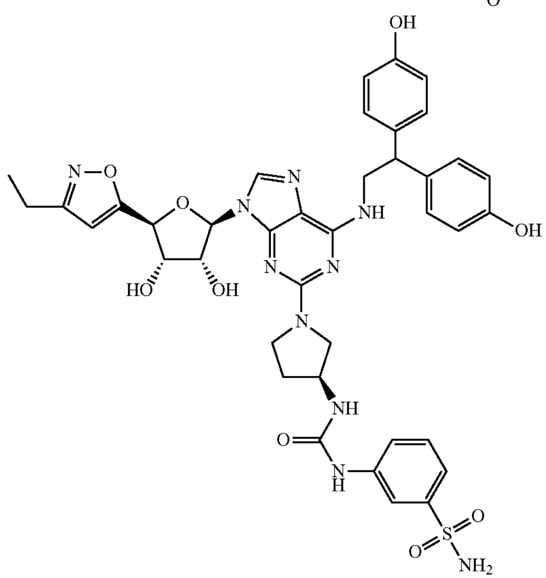 | 5-methyl-3-ethyl-isoxazole | 1,1-bis(4-hydroxyphenyl)propyl | 3-sulfamoylphenyl | 3-[3-((R)-1-{6-[2,2-Bis-(4-hydroxyphenyl)-ethylamino]-9-[(2R,3R,4S,5S)-5-(3-ethyl-isoxazol-5-yl)-3,4-dihydroxy-tetrahydro-furan-2-yl]-9H-purin-2-yl]-pyrrolidin-3-yl)-ureido]-benzenesulfonamide |

-continued

| Ex. | Structure | R¹ | R² | R³ | Name |
|---|---|---|---|---|---|
| 25 | 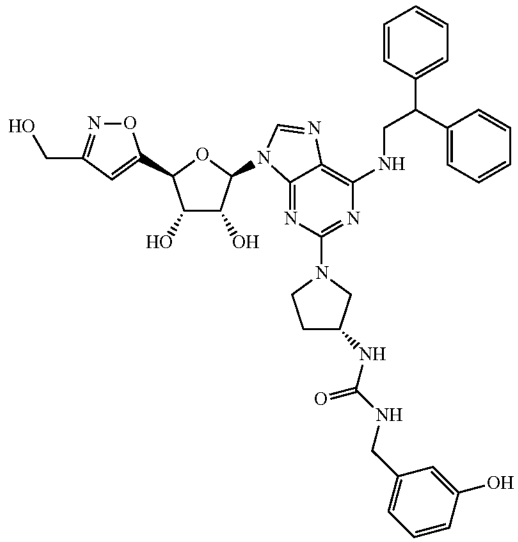 | | | | 1-{(R)-1-[9-[(2R,3R,4S,5S)-3,4-Dihydroxy-5-(3-hydroxymethyl-isoxazol-5-yl)-tetrahydrofuran-2-yl]-6-(2,2-diphenyl-ethylamino)-9H-purin-2-yl]-pyrrolidin-3-yl}-3-(3-hydroxy-benzyl)-urea |
| 26 | 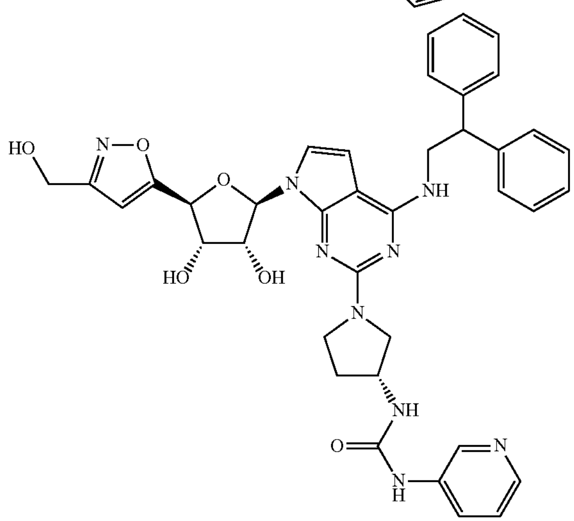 | | | | 1-{(R)-1-[9-[(2R,3R,4S,5S)-3,4-Dihydroxy-5-(3-hydroxymethyl-isoxazol-5-yl)-tetrahydrofuran-2-yl]-6-(2,2-diphenyl-ethylamino)-9H-purin-2-yl]-pyrrolidin-3-yl}-3-pyridin-3-yl-urea |

-continued

| Ex. | Structure | R¹ | R² | R³ | Name |
|---|---|---|---|---|---|
| 27 | 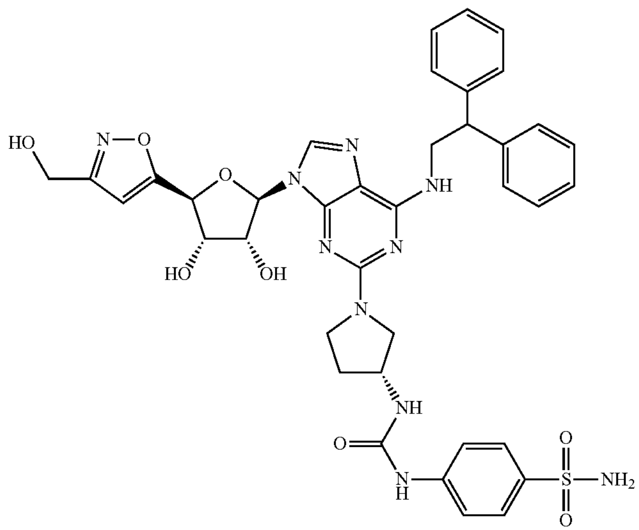 | 5-methylisoxazol-3-yl-methanol (CH₂OH on isoxazole) | 2,2-diphenylethyl | 4-sulfamoyl-methylphenyl (SO₂NH₂) | 4-(3-{(R)-1-[9-[(2R,3R,4S,5S)-3,4-Dihydroxy-5-(3-hydroxymethyl-isoxazol-5-yl)-tetrahydro-furan-2-yl]-6-(2,2-diphenyl-ethylamino)-9H-purin-2-yl]-pyrrolidin-3-yl]-ureido)-benzenesulfonamide |
| 28 | 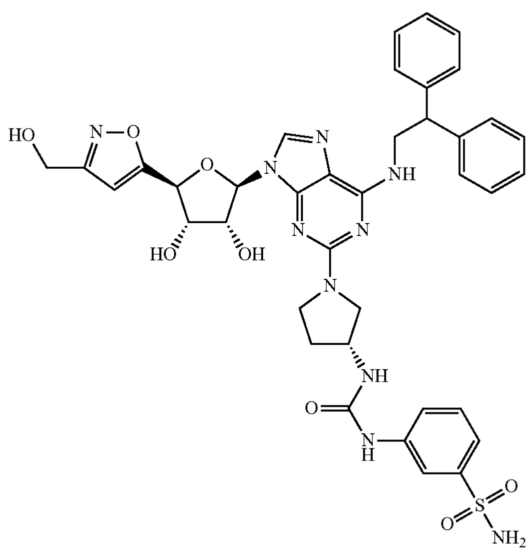 | 5-methylisoxazol-3-yl-methanol | 2,2-diphenylethyl | 3-sulfamoyl-methylphenyl (SO₂NH₂) | 3-(3-{(R)-1-[9-[(2R,3R,4S,5S)-3,4-Dihydroxy-5-(3-hydroxymethyl-isoxazol-5-yl)-tetrahydro-furan-2-yl]-6-(2,2-diphenyl-ethylamino)-9H-purin-2-yl]-pyrrolidin-3-yl]-ureido)-benzenesulfonamide |

-continued

| Ex. Structure | R¹ | R² | R³ | Name |
|---|---|---|---|---|
| 29 | 5-methyl-3-(hydroxymethyl)isoxazole | (S)-2-methyl-3-phenylpropan-1-ol | 3-hydroxybenzyl | 1-{(R)-1-[9-[(2R,3R,4S,5S)-3,4-Dihydroxy-5-(3-hydroxymethyl-isoxazol-5-yl)-tetrahydro-furan-2-yl]-6-((S)-1-hydroxymethyl-2-phenyl-ethylamino)-9H-purin-2-yl]-pyrrolidin-3-yl}-3-(3-hydroxy-benzyl)-urea |
| 30 | 5-methyl-3-(hydroxymethyl)isoxazole | (S)-2-methyl-3-phenylpropan-1-ol | pyridin-3-yl | 1-{(R)-1-[9-[(2R,3R,4S,5S)-3,4-Dihydroxy-5-(3-hydroxymethyl-isoxazol-5-yl)-tetrahydro-furan-2-yl]-6-((S)-1-hydroxymethyl-2-phenyl-ethylamino)-9H-purin-2-yl]-pyrrolidin-3-yl]-3-pyridin-3-yl-urea |

| Ex. | Structure | R¹ | R² | R³ | Name |
|---|---|---|---|---|---|
| 31 | 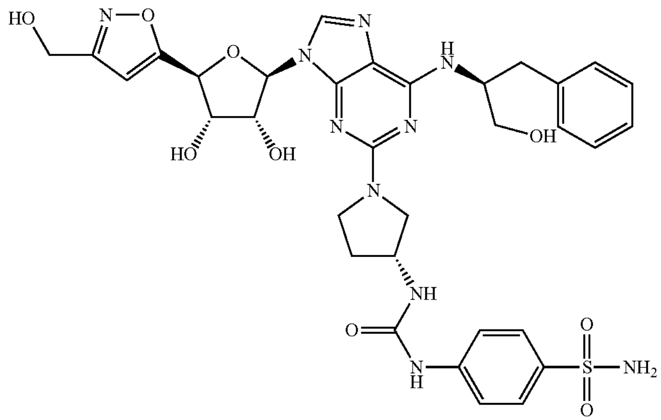 | 5-methylisoxazol-3-yl-methanol | (R)-2-benzyl-propan-1-ol | 4-methyl-benzenesulfonamide (para SO₂NH₂) | 4-(3-{(R)-1-[9-[(2R,3R,4S,5S)-3,4-Dihydroxy-5-(3-hydroxymethyl-isoxazol-5-yl)-tetrahydrofuran-2-yl]-6-((S)-1-hydroxymethyl-2-phenyl-ethylamino)-9H-purin-2-yl]-pyrrolidin-3-yl}-ureido)-benzenesulfonamide |
| 32 | 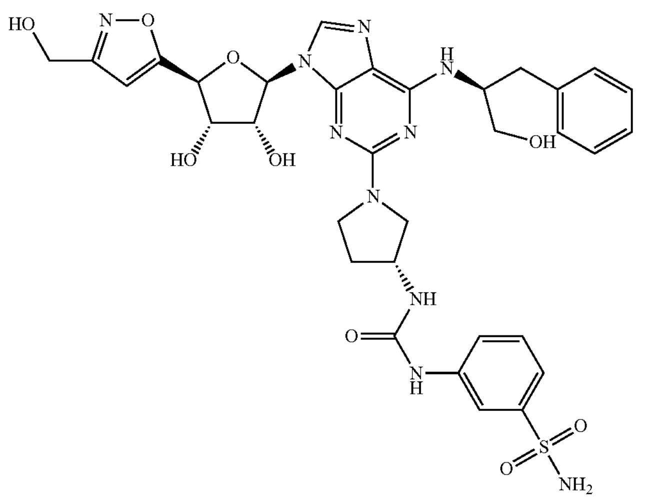 | 5-methylisoxazol-3-yl-methanol | (R)-2-benzyl-propan-1-ol | 3-methyl-benzenesulfonamide (meta SO₂NH₂) | 3-(3-{(R)-1-[9-[(2R,3R,4S,5S)-3,4-Dihydroxy-5-(3-hydroxymethyl-isoxazol-5-yl)-tetrahydrofuran-2-yl]-6-((S)-1-hydroxymethyl-2-phenyl-ethylamino)-9H-purin-2-yl]-pyrrolidin-3-yl}-ureido)-benzenesulfonamide |

-continued

| Ex. | Structure | R¹ | R² | R³ | Name |
|---|---|---|---|---|---|
| 33 | 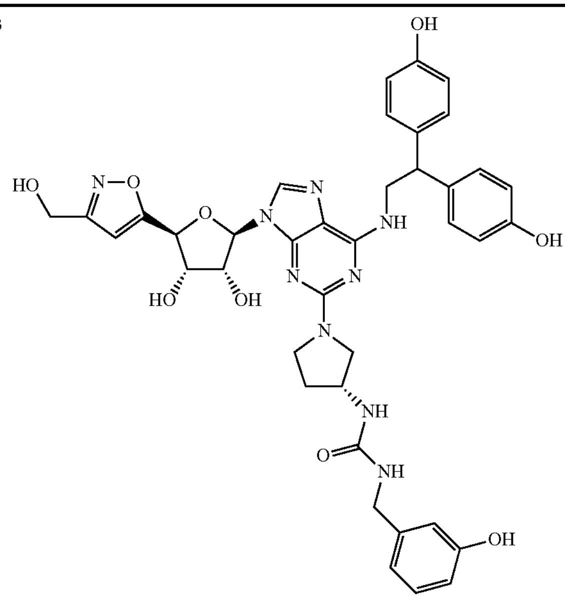 | 5-methyl-isoxazol-3-yl-methanol with CH₂OH | 1,1-bis(4-hydroxyphenyl)propyl | 3-hydroxybenzyl | 1-((R)-1-{6-[2,2-Bis-(4-hydroxy-phenyl)-ethylamino]-9-[(2R,3R,4S,5S)-3,4-dihydroxy-5-(3-hydroxymethyl-isoxazol-5-yl)-tetrahydro-furan-2-yl]-9H-purin-2-yl]-pyrrolidin-3-yl)-3-(3-hydroxy-benzyl)-urea |

| Ex. | Structure | R¹ | R² | R³ | Name |
|---|---|---|---|---|---|
| 34 | 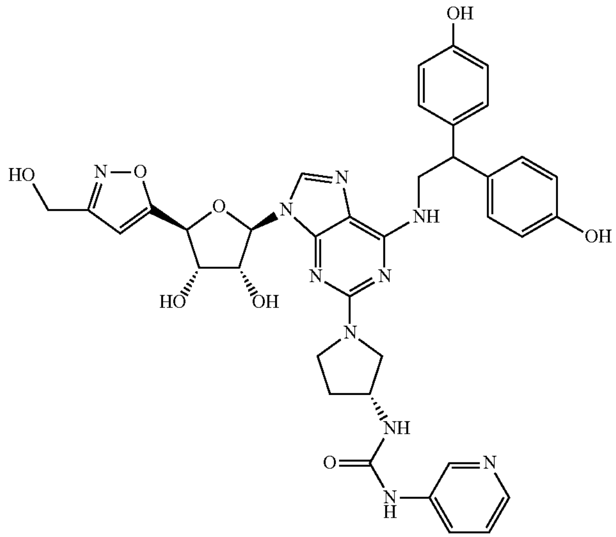 | 5-methylisoxazol-3-yl-methanol (with CH₂OH) | 1,1-Bis(4-hydroxyphenyl)propyl | pyridin-3-yl | 1-((R)-1-{6-[2,2-Bis-(4-hydroxy-phenyl)-ethylamino]-9-[(2R,3R,4S,5S)-3,4-dihydroxy-5-(3-hydroxymethyl-isoxazol-5-yl)-tetrahydro-furan-2-yl]-9H-purin-2-yl]-pyrrolidin-3-yl)-3-pyridin-3-yl-urea |
| 35 | 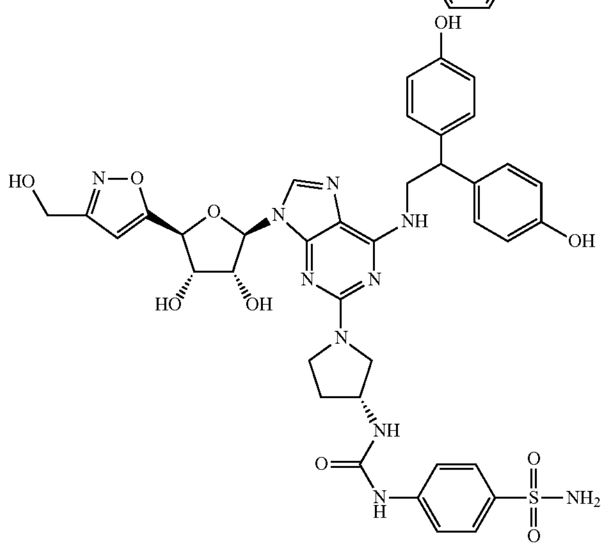 | 5-methylisoxazol-3-yl-methanol (with CH₂OH) | 1,1-Bis(4-hydroxyphenyl)propyl | 4-SO₂NH₂-phenyl | 4-[3-((R)-1-{6-[2,2-Bis-(4-hydroxy-phenyl)-ethylamino]-9-[(2R,3R,4S,5S)-3,4-dihydroxy-5-(3-hydroxymethyl-isoxazol-5-yl)-tetrahydro-furan-2-yl]-9H-purin-2-yl]-pyrrolidin-3-yl)-ureido]-benzenesulfonamide |

-continued

| Ex. | Structure | R¹ | R² | R³ | Name |
|---|---|---|---|---|---|
| 36 | 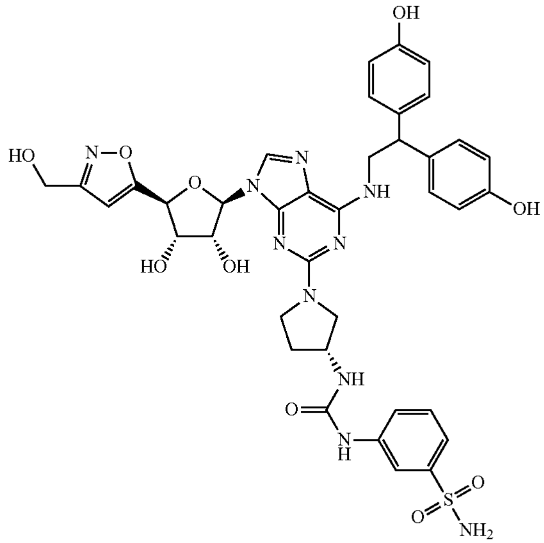 | 5-methylisoxazol-3-yl-methanol (with CH₂OH) | 1,1-bis(4-hydroxyphenyl)propyl | 3-methylbenzenesulfonamide | 3-[3-((R)-1-{6-[2,2-Bis-(4-hydroxyphenyl)-ethylamino]-9-[(2R,3R,4S,5S)-3,4-dihydroxy-5-(3-hydroxymethyl-isoxazol-5-yl)-tetrahydro-furan-2-yl]-9H-purin-2-yl]-pyrrolidin-3-yl)-ureido]-benzenesulfonamide |
| 37 | 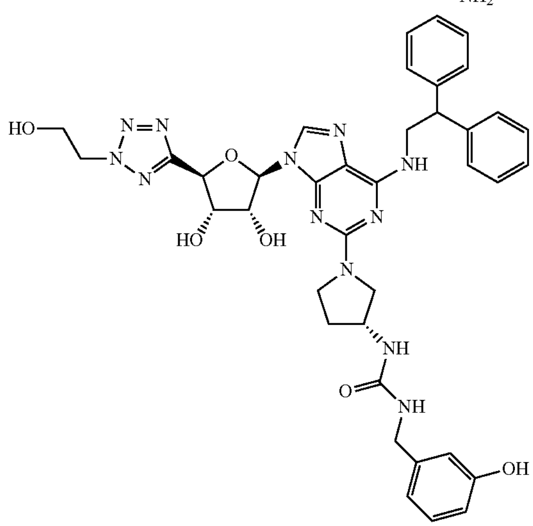 | 2-(5-methyl-2H-tetrazol-2-yl)ethanol | 2,2-diphenylethyl | 3-hydroxyphenyl | 1-{(R)-1-[9-{(2R,3R,4S,5R)-3,4-Dihydroxy-5-[2-(2-hydroxy-ethyl)-2H-tetrazol-5-yl]-tetrahydro-furan-2-yl}-6-(2,2-diphenyl-ethylamino)-9H-purin-2-yl]-pyrrolidin-3-yl}-3-(3-hydroxy-benzyl)-urea |

-continued

| Ex. | Structure | R¹ | R² | R³ | Name |
|---|---|---|---|---|---|
| 38 | 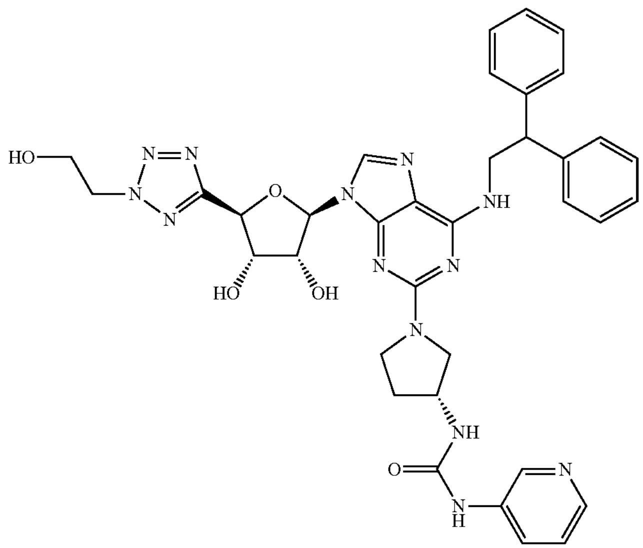 | | | | 1-{(R)-1-[9-{(2R,3R,4S,5R)-3,4-Dihydroxy-5-[2-(2-hydroxy-ethyl)-2H-tetrazol-5-yl]-tetrahydro-furan-2-yl]-6-(2,2-diphenyl-ethylamino)-9H-purin-2-yl]-pyrrolidin-3-yl}-urea |
| 39 | 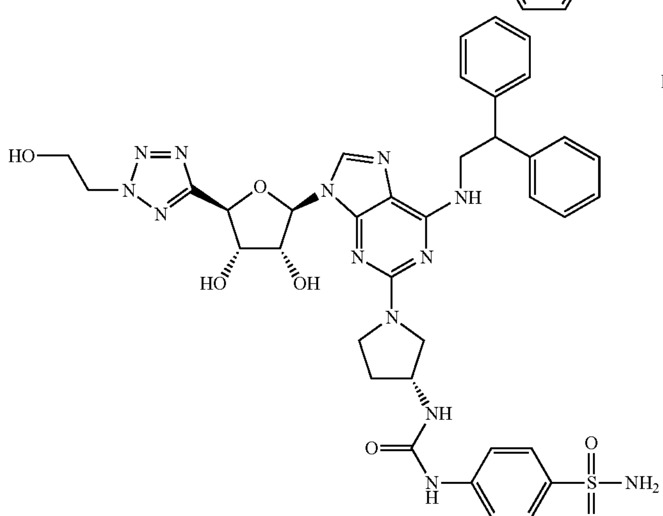 | | | | 4-(3-{(R)-1-[9-{(2R,3R,4S,5R)-3,4-Dihydroxy-5-[2-(2-hydroxy-ethyl)-2H-tetrazol-5-yl]-tetrahydro-furan-2-yl]-6-(2,2-diphenyl-ethylamino)-9H-purin-2-yl]-pyrrolidin-3-yl}-ureido)-benzenesulfonamide |

-continued

| Ex. | Structure | R¹ | R² | R³ | Name |
|---|---|---|---|---|---|
| 40 | 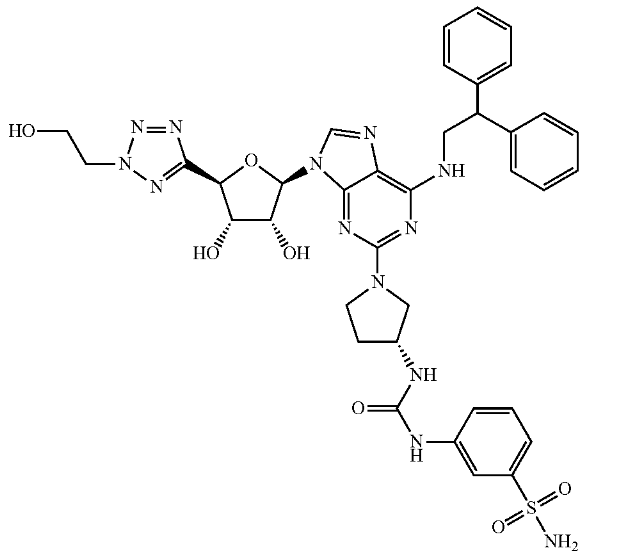 | | | | 3-(3-{(R)-1-[9-{(2R,3R,4S,5R)-3,4-Dihydroxy-5-[2-(2-hydroxy-ethyl)-2H-tetrazol-5-yl]-tetrahydro-furan-2-yl]-6-(2,2-diphenyl-ethylamino)-9H-purin-2-yl]-pyrrolidin-3-yl]-ureido)-benzenesulfonamide |
| 41 | 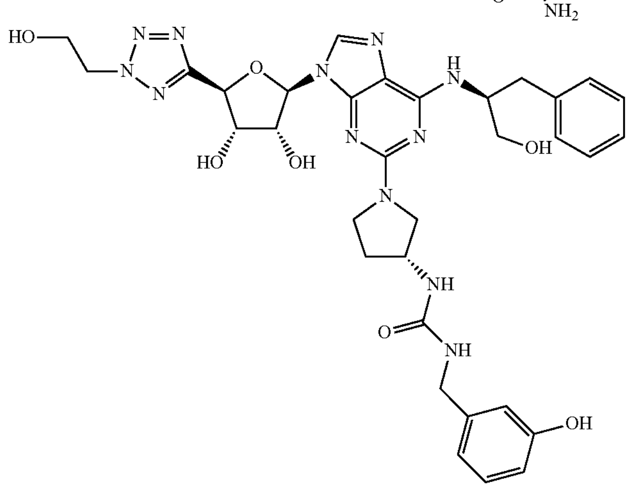 | | | | 1-{(R)-1-[9-{(2R,3R,4S,5R)-3,4-Dihydroxy-5-[2-(2-hydroxy-ethyl)-2H-tetrazol-5-yl]-tetrahydro-furan-2-yl]-6-((S)-1-hydroxymethyl-2-phenyl-ethylamino)-9H-purin-2-yl]-pyrrolidin-3-yl}-3-(3-hydroxy-benzyl)-urea |

-continued

| Ex. | Structure | R¹ | R² | R³ | Name |
|---|---|---|---|---|---|
| 42 | [structure] | [structure] | [structure] | [structure] | 1-{(R)-1-[9-{(2R,3R,4S,5R)-3,4-Dihydroxy-5-[2-(2-hydroxy-ethyl)-2H-tetrazol-5-yl]-tetrahydro-furan-2-yl]-6-((S)-1-hydroxymethyl-2-phenyl-ethylamino)-9H-purin-2-yl]-pyrrolidin-3-yl}-3-pyridin-3-yl-urea |
| 43 | [structure] | [structure] | [structure] | [structure] | 4-(3-{(R)-1-[9-{(2R,3R,4S,5R)-3,4-Dihydroxy-5-[2-(2-hydroxy-ethyl)-2H-tetrazol-5-yl]-tetrahydro-furan-2-yl]-6-((S)-1-hydroxymethyl-2-phenyl-ethylamino)-9H-purin-2-yl]-pyrrolidin-3-yl}-ureido)-benzenesulfonamide |

-continued

| Ex. | Structure | R¹ | R² | R³ | Name |
|---|---|---|---|---|---|
| 44 | 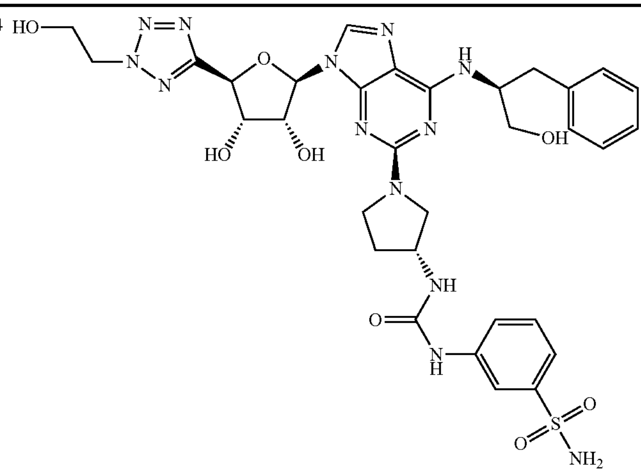 | | | | 3-(3-{(R)-1-[9-{(2R,3R,4S,5R)-3,4-Dihydroxy-5-[2-(2-hydroxy-ethyl)-2H-tetrazol-5-yl]-tetrahydro-furan-2-yl]-6-((S)-1-hydroxymethyl-2-phenyl-ethylamino)-9H-purin-2-yl]-pyrrolidin-3-yl}-ureido)-benzenesulfonamide |
| 45 | 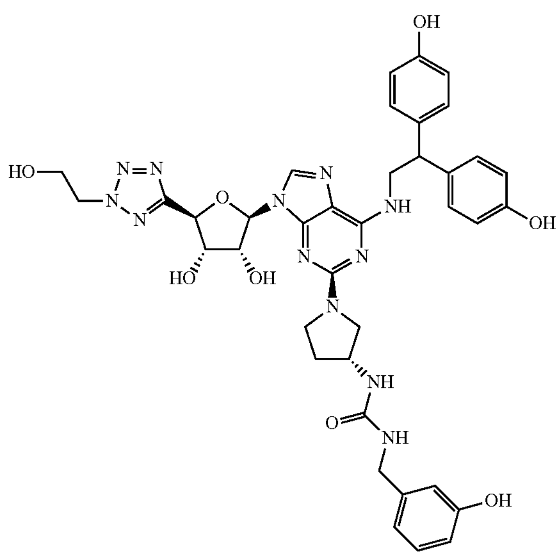 | | | | 1-[(R)-1-(6-[2,2-Bis-(4-hydroxy-phenyl)-ethylamino]-9-{(2R,3R,4S,5R)-3,4-dihydroxy-5-[2-(2-hydroxy-ethyl)-2H-tetrazol-5-yl]-tetrahydro-furan-2-yl]-9H-purin-2-yl)-pyrrolidin-3-yl]-3-(3-hydroxy-benzyl)-urea |

-continued

| Ex. | Structure | R¹ | R² | R³ | Name |
|---|---|---|---|---|---|
| 46 | 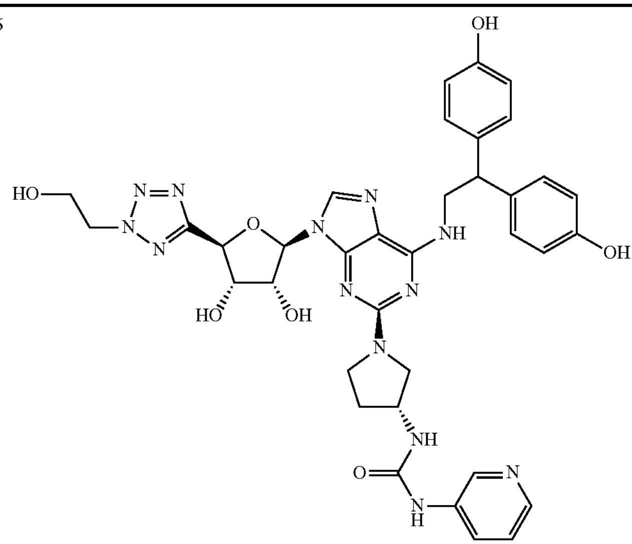 | 2-(2-hydroxyethyl)-5-methyl-tetrazole with hydroxyethyl | 1,1-Bis(4-hydroxyphenyl)propyl | pyridin-3-yl | 1-[(R)-1-(6-[2,2-Bis-(4-hydroxy-phenyl)-ethylamino]-9-{(2R,3R,4S,5R)-3,4-dihydroxy-5-[2-(2-hydroxy-ethyl)-2H-tetrazol-5-yl]-tetrahydro-furan-2-yl}-9H-purin-2-yl)-pyrrolidin-3-yl]-3-pyridin-3-yl-urea |
| 47 | 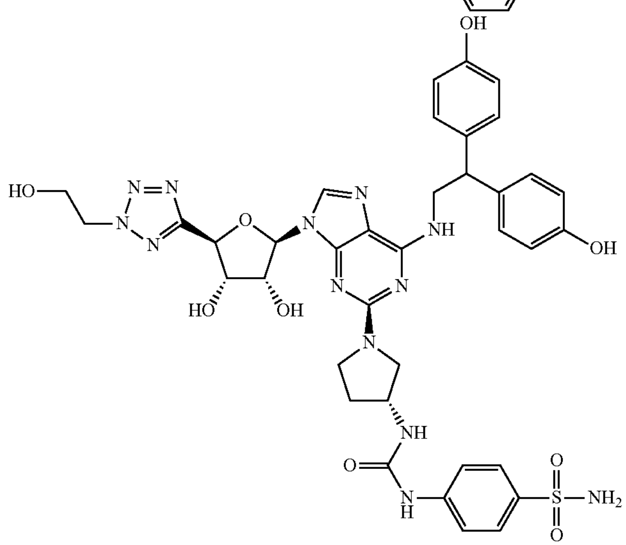 | 2-(2-hydroxyethyl)-5-methyl-tetrazole with hydroxyethyl | 1,1-Bis(4-hydroxyphenyl)propyl | 4-SO₂NH₂-phenyl | 4-{3-[(R)-1-(6-[2,2-Bis-(4-hydroxy-phenyl)-ethylamino]-9-{(2R,3R,4S,5R)-3,4-dihydroxy-5-[2-(2-hydroxy-ethyl)-2H-tetrazol-5-yl]-tetrahydro-furan-2-yl}-9H-purin-2-yl)-pyrrolidin-3-yl]-ureido}-benzenesulfonamide |

| Ex. | Structure | R¹ | R² | R³ | Name |
|---|---|---|---|---|---|
| 48 | 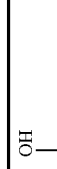 | 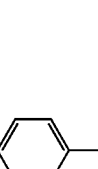 | 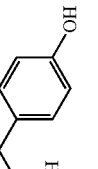 | | 3-{3-[(R)-1-(6-[2,2-Bis-(4-hydroxy-phenyl)-ethylamino]-9-{(2R,3R,4S,5R)-3,4-dihydroxy-5-[2-(2-hydroxy-ethyl)-2H-tetrazol-5-yl]-tetrahydro-furan-2-yl}-9H-purin-2-yl)-pyrrolidin-3-yl]-ureido)-benzenesulfonamide |

Preparation of Intermediate Compounds

Intermediate A 4,4'-(2-Aminoethylidene)bis-phenol

This compound is prepared by the procedure of R. M. Schelkun et al., *Bioorg Med Chem Lett*, Vol. 9, pp. 2447-2452 (1999).

Intermediate BA (3-Hydroxy-benzyl)-carbamic acid phenyl ester

3-Hydroxybenzylamine (200 mg, 1.62 mmol) and sodium hydrogen carbonate (273 mg, 3.25 mmol) suspended in water/DCM (4 mL, 1:1) is treated with phenyl chloroformate (0.204 mL, 1.62 mmol). After stirring at RT overnight, the reaction mixture is diluted with more DCM/water and the organic phase is separated. The organic portion is concentrated in vacuo to afford the titled compound. (MH+244)

Intermediate BB Pyridin-3-yl-carbamic acid phenyl ester

Phenyl chloroformate (0.733 mL, 5.84 mmol) is suspended in pyridine/DCM (3 mL, 2:1). The solution is stirred at 0° C., and 3-aminopyridine (500 mg, 5.31 mmol) dissolved in DCM (1 mL) is added dropwise. The reaction mixture is at 0° C. for 1 hour. The solvent is removed in vacuo and the residue is dissolved in ethyl acetate. This organic portion is washed with 0.1 M HCl and then concentrated in vacuo to afford the titled compound. (MH+215)

Intermediates BC and BD
These compounds namely,
(3-Sulfamoyl-phenyl)-carbamic acid phenyl ester (Intermediate BC); and
(4-Sulfamoyl-phenyl)-carbamic acid phenyl ester (Intermediate BD),
are prepared analogously to Intermediate BB by replacing 3-aminopyridine with the appropriate amine.

The following intermediates of formula (C)

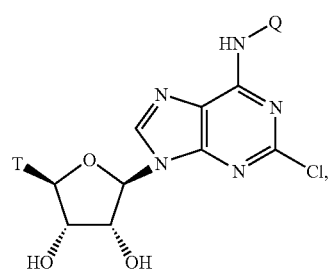

(C)

are shown below in Table 1a, the methods of preparation being described hereinafter.

TABLE 1

| Intermediate | T | Q |
|---|---|---|
| CA | H₃C-isoxazole-methyl | OH-CH₂-CH(CH₃)-CH₂-phenyl |
| CB | H₃C-isoxazole-methyl | bis(4-hydroxyphenyl)propyl |
| CC | H₃C-isoxazole-methyl | 1,1-diphenylpropyl |
| CD | H₃C-CH₂-tetrazole-methyl | OH-CH₂-CH(CH₃)-CH₂-phenyl |
| CE | H₃C-CH₂-tetrazole-methyl | bis(4-hydroxyphenyl)propyl |
| CF | H₃C-CH₂-tetrazole-methyl | 1,1-diphenylpropyl |
| CG | HO-CH₂-isoxazole-methyl | OH-CH₂-CH(CH₃)-CH₂-phenyl |

TABLE 1-continued

| Intermediate | T | Q |
|---|---|---|
| CH | HO-CH2-isoxazole (3-hydroxymethyl-5-methyl-isoxazole) | bis(4-hydroxyphenyl)propyl |
| CI | HO-CH2-isoxazole (3-hydroxymethyl-5-methyl-isoxazole) | 1,1-diphenylpropyl |
| CJ | 2-benzyl-5-methyl-tetrazole | (S)-2-methyl-3-phenyl-propan-1-ol |
| CK | 2-benzyl-5-methyl-tetrazole | 1-(4-hydroxyphenyl)propyl |

Intermediate CA (2R,3R,4S,5S)-2-[6-((S)-1-Benzyl-
2-hydroxy-ethylamino)-2-chloro-purin-9-yl]-5-(3-
ethyl-isocazol-5-yl)-tetrahydro-furan-3,4-diol Step CA1: Acetic acid (2R,3R,4R,5S)-4-acetoxy-2-
[6-((S)-1-benzyl-2-hydroxy-ethylamino)-2-chloro-
purin-9-yl]-5-(3-ethyl-isoxazol-5-yl)-tetrahydro-
furan-3-yl ester hydrochloride A mixture comprising acetic acid (2R,3R,4R,5S)-4-acetoxy-2-(2,6-dichloro-purin-9-yl)-5-(3-ethyl-isoxazol-5-yl)-tetrahydro-furan-3-yl ester (WO 99/38877) (1 g, 2.13 mmol), (S)-2-amino-3-phenyl-propan-1-ol (0.321 g, 2.13 mmol) and DIPEA (0.275 g, 2.13 mmol) in DCE (5 mL) is stirred under an inert atmosphere of argon overnight. After cooling to room temperature (RT), 1 M HCl is added, the organic portion is separated and concentrated in vacuo to afford the title compound which is used in the next step without further purification. (MH+585.1)

Step CA2: (2R,3R,4S,5S)-2-[6-((S)-1-Benzyl-2-
hydroxy-ethylamino)-2-chloro-purin-9-yl]-5-(3-
ethyl-isoxazol-5-yl)-tetrahydro-furan-3,4-diol A solution of acetic acid (2R,3R,4R,5S)-4-acetoxy-2-[6-((S)-1-benzyl-2-hydroxy-ethyl amino)-2-chloro-purin-9-yl]-5-(3-ethyl-isoxazol-5-yl)tetrahydro-furan-3-yl ester hydrochloride (Step AC1) (1.194 g, 2.02 mmol) in MeOH/chloroform (4 at, 3:1 MeOH/chloroform) is treated with saturated potassium carbonate solution (10 mL). After stirring at RT overnight, the reaction mixture is diluted with DCM/water and the organic portion is separated. The organic portion is concentrated in vacuo to afford the title compound. (MH+501)

Intermediate CB-CC

These intermediates namely,
(2R,3R,4S,5S)-2-{6-[2,2-bis-(4-Hydroxy-phenyl)-ethylamino]-2-chloro-purin-9-yl}-5-(3-ethyl-isoxazol-5-yl)-tetrahydro-furan-3,4-diol (Intermediate CB); and
(2R,3R,4S,5S)-2-[2-Chloro-6-(2,2-diphenyl-ethylamino)-purin-9-yl]-5-(3-ethyl-isoxazol-5-yl)-tetrahydro-furan-3,4-diol (Intermediate CC),
are prepared analogously to Intermediate CA by replacing (S)-2-amino-3-phenyl-propan-1-ol with the appropriate amine.

Intermediate CD (2R,3R,4S,5R)-2-[6-((S)-1-Benzyl-
2-hydroxyethylamino)-2-chloro-purin-9-yl]-5-(2-
ethyl-2-tetrazol-5-yl)-tetrahydro-furan-3,4-diol Step CD1: Acetic acid (2R,3R,4R,5R)-4-acetoxy-2-
[6-((S)-1-benzyl-2-hydroxy-ethyl amino)-2-chloro-
purin-9-yl]-5-(2 ethyl-2H-tetrazol-5-yl)-tetrahydro-
furan-3-yl ester The title compound is prepared analogously to acetic acid (2R,3R,4R,5S)-4-acetoxy-2-[6-((S)-1-benzyl-2-hydroxy-ethyl amino)-2-chloro-purin-9-yl]5-(3-ethyl-isoxazol-5-yl)-tetrahydro-furan-3-yl ester hydrochloride (Step CA1) by replacing acetic acid (2R,3R,4R,5S)-4-acetoxy-2-(2,6-dichloro-purin-9-yl)-5-(3-ethyl-isoxazol-5-yl)-tetrahydro-furan-3-yl ester (WO 99/38877) with acetic acid (2R,3R,4R,5R)-4-acetoxy-2-(2,6-dichloro-purin-9-yl)-5-(2-ethyl-2H-tetrazol-5-yl)-tetrahydro-furan-3-yl ester (WO 98/28319).

Step CD2: (2R,3R,4S,5R)-2-[6-((S)-1-Benzyl-2-
hydroxy-ethylamino)-2-chloro-purin-1-yl]-5-(2-
ethyl-2H-tetrazol-5-yl)-tetrahydro-furan-3,4-diol The title compound is prepared from acetic acid (2R,3R,4R,5R)-4-acetoxy-2-[6-((S)-1-benzyl-2-hydroxy-ethylamino)-2-chloro-purin-9-yl]-5-(2-ethyl-2H-tetrazol-5-yl)-tetrahydro-furan-3-yl ester (Step CD1) analogously to (2R,3R,4S,5S)-2-[6-((S)-1-benzyl-2-hydroxy-ethylamino-2-chloro-purin-9-yl]-5-(3-ethyl-isoxazol-5-yl)-tetrahydro-furan-3,4-diol (Step CA 2).

Intermediates CE and CF

These intermediates namely,
(2R,3R,4S,5R)-2 {6-[2,2-bis-(4-Hydroxy-phenyl)-ethylamino]-2-chloro-purin-9-yl}-5-(2-ethyl-2H-tetrazol-5-yl)-tetrahydro-furan-3,4-diol (Intermediate CE); and
(2R,3R,4S,5R)-2-[2-Chloro-6-(2,2-diphenyl-ethylamino)-purin-9-yl]-5-(2-ethyl-2H-tetrazol-5-yl)-tetrahydro-furan-3,4-diol (Intermediate CF),
are prepared analogously to Intermediate CD by replacing (S)-2-amino-3-phenyl-propan-1-ol with the appropriate amine.

Intermediate CG (2R,3R,4S,5S)-2-[2-Chloro-6-(2,2-diphenyl-ethylamino)-purin-yl]5-(3-hydroxymethyl-isoxazol-5-yl)-tetrahydro-furan-3,4-diol

Step CG1: Acetic acid (2R,3R,4R,5S-4-acetoxy-5-(3-acetoxymethyl-isoxazo-5-yl)-2-[2-chloro-6-(2,2-diphenyl-ethylamino)-purin-9-yl]-tetrahydro-furan-3-yl ester A mixture containing acetic acid (2R,3R,4R,5S)-4-acetoxy-5-(3-acetoxymethyl-isoxazol-5-yl)-2-(2,6-dichloro-purin-9-yl)-tetrahydro-furan-3-yl ester (WO 99/38877), 2,2-diphenylethylamine and DIPEA in DCE is stirred under an inert atmosphere of argon at 50° C. overnight. After cooling to RT, 0.1 M HCl is added, the organic portion separated and concentrated in vacuo to afford the titled compound which is used in the next step without further purification.

Step CG2: (2R,3R,4S,5S)-2-[2-Chloro-6-(2,2-diphenyl-ethylamino)-purin-9-yl]-5-(3-hydroxymethyl-isoxazol-5-yl)-tetrahydro-furan-3,4-diol A solution of acetic acid (2R,3R,4S,5S)-4-acetoxy-5-(3-acetoxymethyl-isoxazol-5-yl)-2-[2-chloro-6-(2,2-diphenyl-ethylamino)-purin-9-yl]-tetrahydro-furan-3-yl ester (Step CG1) in MeOH/chloroform (3:1 MeOH/chloroform) is treated with saturated potassium carbonate solution. After stirring at RT overnight, the reaction is diluted with DCM/water and the organic portion is separated. The organic portion is concentrated in vacuo to afford the titled compound.

Intermediate CH (2R,3R,4S,5S)-2-{6-[2,2-bis(4-Hydroxy-phenyl)-ethylamino]-2-chloro-purin-9-yl}-5-(3-hydroxymethyl-isoxazol-5-yl)-tetrahydrofuran-3,4-diol The title compound is prepared from acetic acid (2R,3R,4R,5S)-4-acetoxy-5-(3-acetoxymethyl-isoxazol-5-yl)-2-(2,6-dichloro-purin-9-yl)-tetrahydro-furan-3-yl ester (WO 99/38877) analogously to (2R,3R,4S,5S)-2-[2-chloro-6-(2,2-diphenyl-ethylamino)-purin-9-yl]-5-(3-hydroxymethyl-isoxazol-5-yl)-tetrahydro-furan-3,4-diol (Intermediate CG) by replacing 2,2-diphenylethylamine with 4,4'-(2-aminoethylidene)bisphenol (Intermediate A).

Intermediate CI (2R,3R,4S,5S)-2-[2-Chloro-6-(S)-1-hydroxymethyl-2-phenyl-ethylamino)-purin-9-yl]-5-(3-hydroxymethyl-isoxazol-yl)-tetrahydro-furan-3,4 diol The title compound is prepared from acetic acid (2R,3R,4R,5S)-4-acetoxy-5-(3-acetoxymethyl-isoxazol-5-yl)-2-(2,6-dichloro-purin-9-yl)-tetrahydro-furan-3-yl ester (WO 99/38877) analogously to (2R,3R,4S,5S)-2-[2-chloro-6-(2,2-diphenyl-ethylamino)-purin-9-yl]-5-(3-hydroxymethyl-isoxazol-5-yl)-tetrahydro-furan-3,4-diol (Intermediate CG) by replacing 2,2-diphenylethylamine with (S)-2-amino-3-phenyl-propan-1-ol.

Intermediate CJ (2R,3R,4S,5R)-2-[6-((S)-1-Benzyl-2-hydroxyethylamino)-2-chloro-purin-9-yl]-5-(2-benzyl-2H-tetrazol-5-yl)-tetrahydro-furan-3,4-diol The title compound is prepared in an analogous fashion to (2R,3S,4R,5R)-2-(2-benzyl-2H-tetrazol-5-yl)-5-[2-chloro-6-(2,2-diphenylethylamino)-purin-9-yl]-tetrahydro-furan-3,4-diol (WO 99/38877) by replacing 2,2-diphenylethylamine with (S)-2-amino-3-phenyl-propan-1-ol

Intermediate CK (2R,3S,4R,5R)-2-(2-Benzyl-2H-tetrazol-5-yl)-5-{6-[2,2-bis-(4-hydroxy-phenyl)ethylamino]-2 chloro-purin-9-yl}tetrahydro-furan-3,4-diol The title compound is prepared in an analogous fashion to (2R,3S,4R,5R)-2-(2-benzyl-2H-tetrazol-5-yl)-5-[2-chloro-6-(2,2-diphenyl-ethylamino)-purin-9-yl]-tetrahydro-furan-3,4-diol (WO 99/38877) by replacing 2,2-diphenylethylamine with 4,4'-(2-aminoethylidene)bis-phenol (Intermediate A).

Preparation of Examples

Example 1

1-((R)-1-{6-(2,2-Diphenyl-ethylamino)-9-[(2R,3R,4S,5R)-5-(2-ethyl-2H tetrazol-5-yl)-3,4-dihydroxy-tetrahydro-furan-2-yl]-9H-purin-2-yl}-pyrrolidin-3 yl)-3-(3-hydroxy-benzyl)-urea trifluoroacetate

Step 1: (2R,3R,4S,5R)-2-[6-(2,2-Diphenyl-ethylamino)-2-((R)-3-BOC-amino-pyrrolidin-1-yl)-purin-9-yl]-5-(2-ethyl-2H-tetrazol-5-yl-tetrahydro-furan-3,4-diol (2R,3R,4S,5R)-2-[2-Chloro-6-(2,2-diphenyl-ethylamino)-purin-9-yl]-5-(2-ethyl-2H-tetrazol-5-yl)-tetrahydro-furan-3,4-diol (Intermediate CF) (1 g, 1.82 mmol), (3R)-3-(BOC-amino)pyrrolidine (1.02 g, 5.47 mmol) and sodium iodide (273 mg, 1.82 mmol) are dissolved in acetonitrile (10 mL) and NMP (0.5 mL). The reaction mixture is heated using microwave radiation at 160° C. for 30 minutes in the Personal Chemistry Emrys™ Optimizer microwave reactor. The reaction mixture is concentrated in vacuo and purified by C-18 reverse phase column chromatography eluting with acetonitrile:water (0.1% TFA) (gradient 0-100% acetonitrile) to afford the titled compound.

Step 2: (2R,3R,4S,5R)-2-[2-((R)-3-Amino-pyrrolidin-1-yl)-6-(2,2-diphenylethylamino)-purin-9-yl]-5-(2-ethyl-2H-tetrazol-5-yl)tetrahydro-furan-3,4-diol trifluoroacetate (2R,3R,4S,5R)-2-[6-(2,2-Diphenyl-ethylamino-2-((F-3-BOC-amino-pyrrolidin-1-yl)-purin-9-yl]-5-(2-ethyl-2H-tetrazol-5-yl)-tetrahydro-furan-3,4-diol (Step AA1) is dissolved in DCM and TFA and stirred at RT overnight. The reaction mixture is concentrated in vacuo to afford the titled compound.

Step 3: 1-((R)-1-{6-(2,2-Diphenyl-ethylamino)-9-[(2R,3R,4S,5R)-5-(2-ethyl-2H-tetrazol-5-yl)-3,4-dihydroxy-tetrahydro-furan-2-yl]-9H-purin-2-yl}-pyrrolidin-3-yl)-3-(3-hydroxy-benzyl)-urea trifluoroacetate (2R,3R,4S,5R)-2-[2-((R)-3-Amino-pyrrolidin-1-yl)-(2,2-diphenyl-ethylamino)-purin-9-yl]-5-(2-ethyl-2H-tetrazol-5-yl-tetrahydro-furan-3,4-diol trifluoroacetate and (3-hydroxy-benzyl)-carbamic acid phenyl ester (Intermediate BA) are dissolved in methanol and TEA. The reaction mixture is heated using microwave radiation at 100° C. for 30 minutes in the Personal Chemistry Emrys™ Optimizer microwave reactor. The reaction mixture is concentrated in vacuo and purified by C-18 reverse phase column chromatography eluting with acetonitrile:water (0.1% TFA) (gradient 0-100% acetonitrile) to afford the titled compound.

Examples 2-36

These are prepared analogously to Example 1 by combining the appropriate starting compound from Table 1a (Intermediates CA-CI) with the appropriate phenyl esters (Intermediates BA-BD).

Example 37

1-{(R)-1-[9-{(2R,3R,4S,5R)-3,4-Dihydroxy-5-[2-(2-hydroxyethyl)-2H-tetrazol-5-yl]-tetrahydro-furan-2-yl}6-(2,2-diphenyl-ethylamino)-9H-purin-2-yl]-pyrrolidin 3-yl}-3-(3-hydroxy-benzyl)-urea

Step 1: 1-{(R)-1-[9-[(2R,3R,4S,5R)-6-(2-Benzyl-2H-tetrazol-5-yl)-3,4-dihydroxy-tetrahydro-furan-2-yl]-6-(2,2-diphenyl-ethylamino)-9H-purin-2-yl]-pyrrolidin-3-yl}-3-pyridin-3-yl-urea This compound is prepared from (2R,3S,4R,5R)-2-(2-benzyl-2H-tetrazol-5-yl)-5-[2-chloro-6-(2,2-diphenyl-ethylamino)-purin-9-yl]-tetrahydro-furan-3,4-diol (WO 99/38877) and pyridin-3-yl-carbamic acid phenyl ester (Intermediate BB) analogously to Example 1.

Step 2: 1-((R)-1-[9-[(2R,3R,4S,5R)-3,4-Dihydroxy-5-(2H-tetrazol-5-yl)-tetrahydro-furan-2-yl]-6-(2,2-diphenyl-ethylamino)-9H-purin-2-yl]-pyrrolidin-3-yl}-3-pyridin-3-yl-urea A solution of 1-{(R)-1-[9-[(2R,3R,4S,5R)-5-(2-Benzyl-2H-tetrazol-5-yl)-3,4-dihydroxy-tetrahydro-furan-2-yl]-6-(2,2-diphenyl-ethylamino)-9H-purin-2-yl]-pyrrolidin-3-yl}-3-pyridin-3-yl-urea in EtOH under an inert atmosphere of argon is treated with 10% palladium on carbon followed by ammonium formate. The reaction mixture is heated to 50° C. for 4 hours and then filtered through Celite®. The filtrate is concentrated in vacuo to afford the title compound.

Step 3: 1-{(R)-1-[9-{(2R,3R,4S,5R)-3,4-Dihydroxy-5-[2-(2-hydroxy-ethyl)-2H-tetrazol-5-yl]-tetrahydro-furan-2-yl}-6-(2,2-diphenyl-ethylamino)-9H-purin-2-yl]-pyrrolidin-3-yl}-3-pyridin-3-yl-urea A solution of 1-{(R)-1-[9-[(2R,3R,4S R)-3,4-dihydroxy-5-(2H-tetrazol-5-yl)-tetrahydro-furan-2-yl]-6-(2,2-diphenyl-ethylamino)-9H-purin-2-yl]-pyrrolidin-3-yl}-3-pyridin-3-yl-urea in DMF is treated with potassium carbonate followed by 3-bromoethanol and stirred at RT for 18 hours. The mixture is then filtered and the filtrate is concentrated in vacuo. Purification of the crude product by C-18 reverse phase column chromatography eluting with acetonitrile:water (0.1% TFA) (gradient 0-100% acetonitrile) to affords the titled compound.

Examples 38-40

These compounds are prepared analogously to Example 37 by replacing pyridin-3-yl-carbamic acid phenyl ester (Intermediate BB) with Intermediates BA, BD and BC, respectively.

Examples 41-44

These examples are prepared analogously to Examples 37-40 by replacing (2R,3S,4R,5R)-2-(2-benzyl-2H-tetrazol-5-yl)-5-[2-chloro-6-(2,2-diphenyl-ethylamino)-purin-9-yl]-tetrahydro-furan-3,4-diol (WO 99/38877) with (2R,3R,4S,5R)-2-[6-((S)-1-Benzyl-2-hydroxy-ethylamino)-2-chloro-purin-9-yl]-5-(2-benzyl-2H-tetrazol-5-yl)-tetrahydro-furan-3,4-diol (Intermediate CJ).

Examples 45-48

These examples are prepared analogously to Examples 37-40 by replacing (2R,3S,4R,5R)-2-(2-benzyl-2H-tetrazol-5-yl)-5-[2-chloro-6-(2,2-diphenylethylamino)-purin-9-yl]-tetrahydro-furan-3,4-diol (WO 99/38877) with (2R,3S,4R,5R)-2-(2-Benzyl-2H-tetrazol-5-yl)-5-{6-[2,2-bis-(4-hydroxy-phenyl)ethylamino]-2-chloro-purin-9-yl}-tetrahydro-furan-3,4-diol (Intermediate CK)

Carbocylclic Examples

Examples C1-C84

Compounds of formula (I)

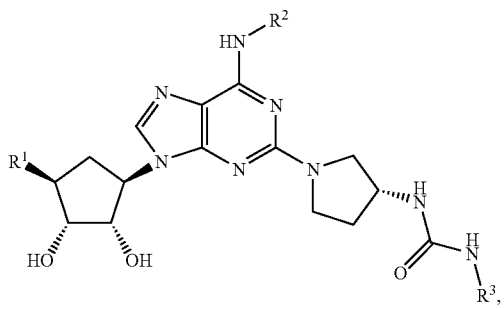

are shown in the following table. Methods for preparing such compounds are described hereinafter. The table also shows mass spectrometry, MH⁺ {ESMS}, data. The Examples are trifluoroacetate salts.

| Ex. | Structure | R¹ |
|---|---|---|
| C1 | 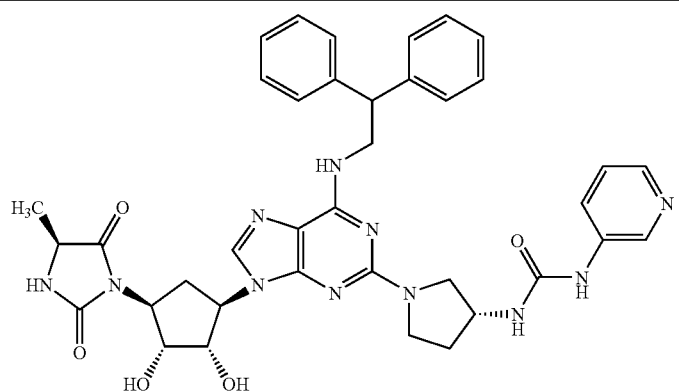 | 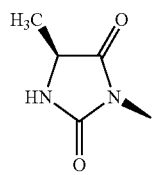 |
| C2 | 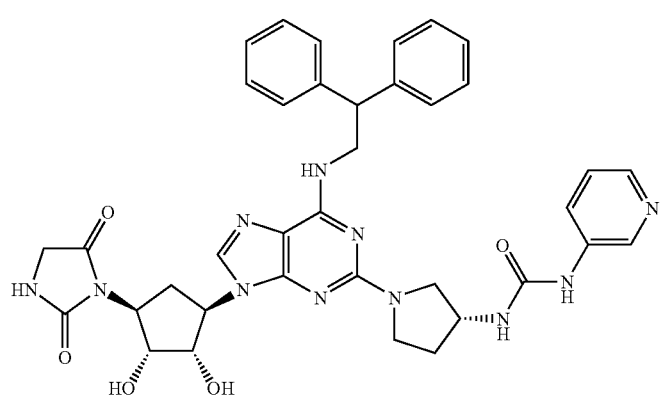 | 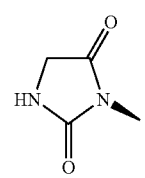 |
| C3 | 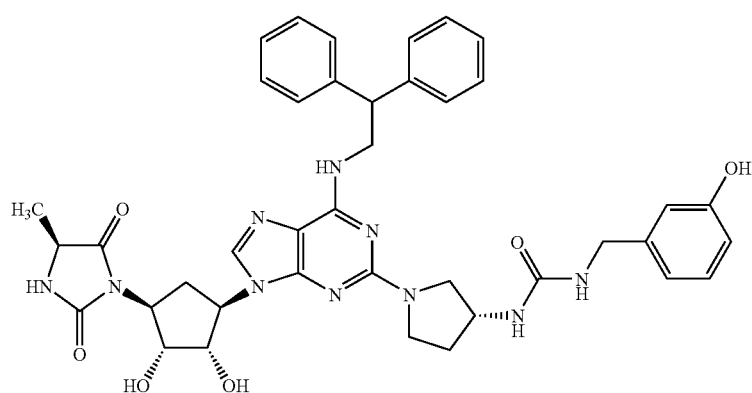 | 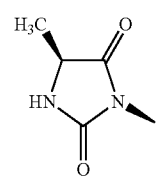 |
| C4 | 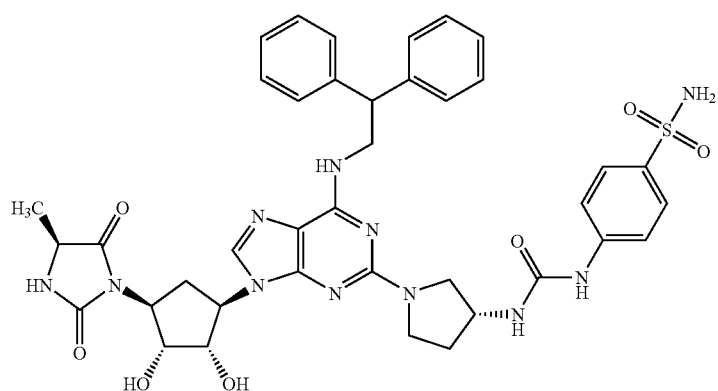 | 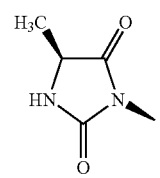 |

-continued
C5 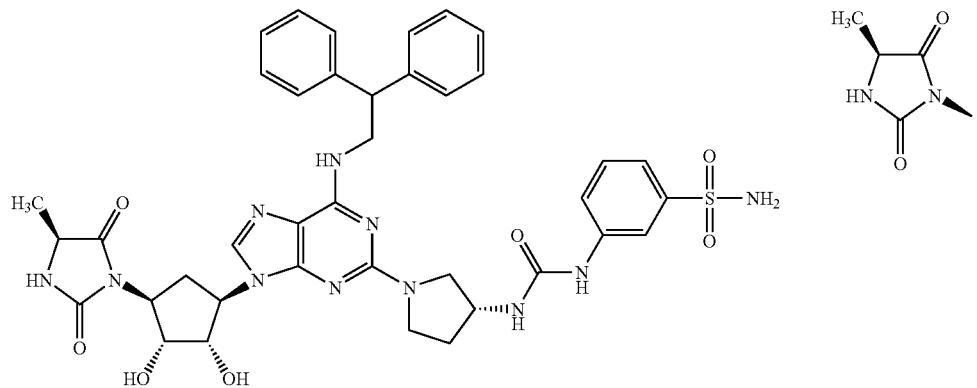
C6 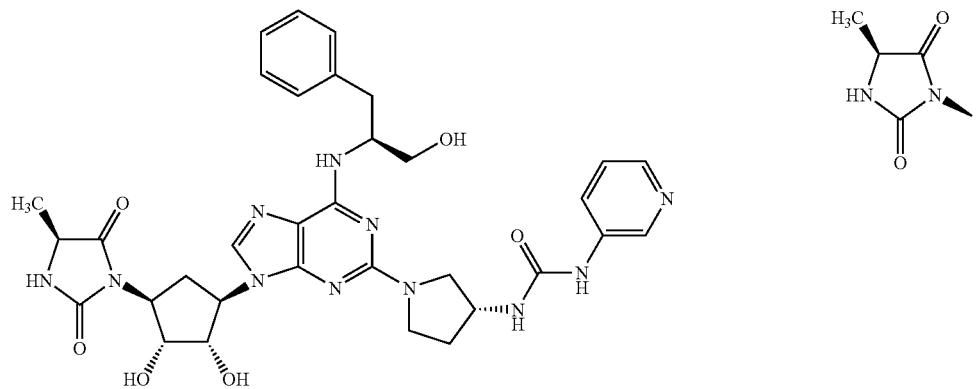
C7 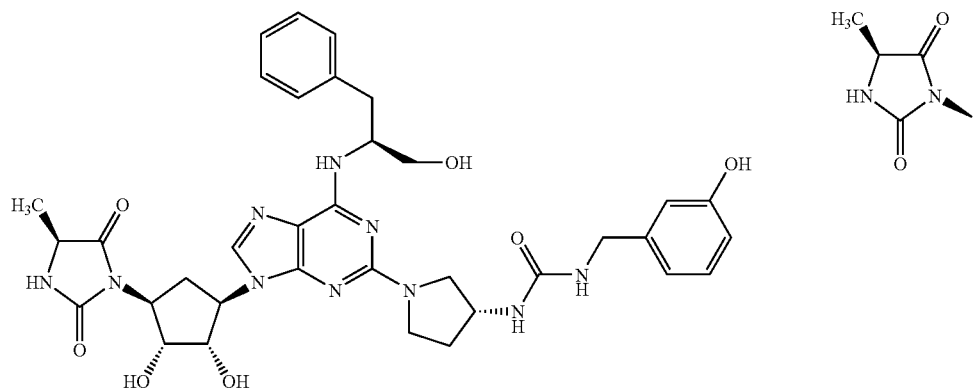
C8 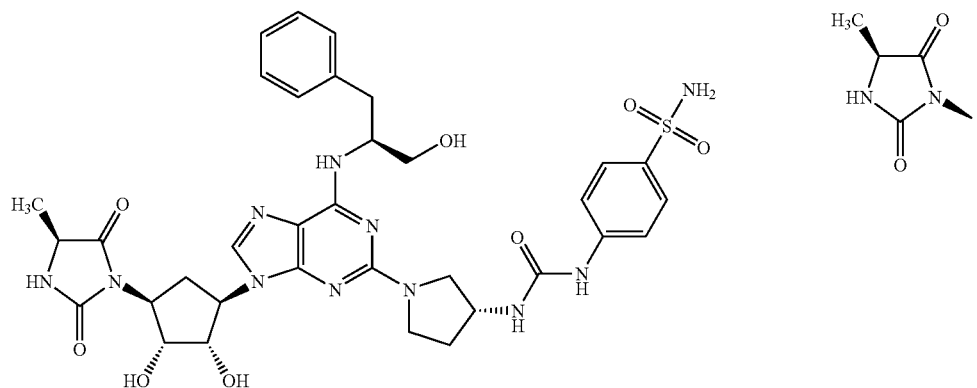

-continued
C9 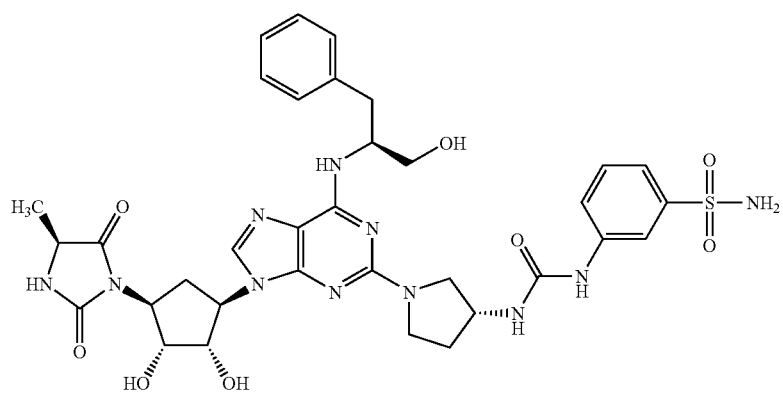 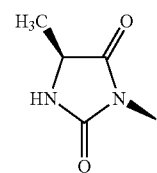
C10 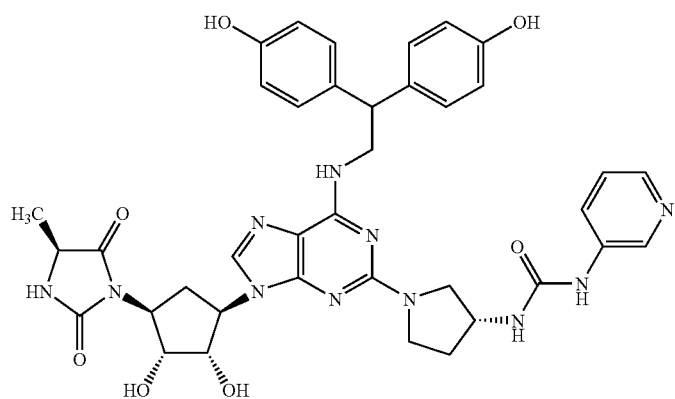 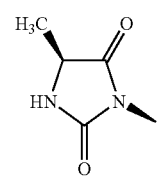
C11 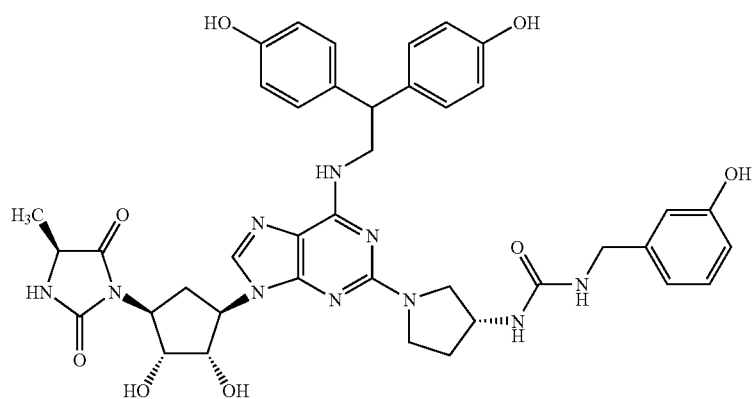 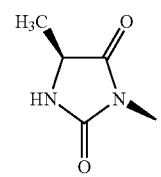
C12 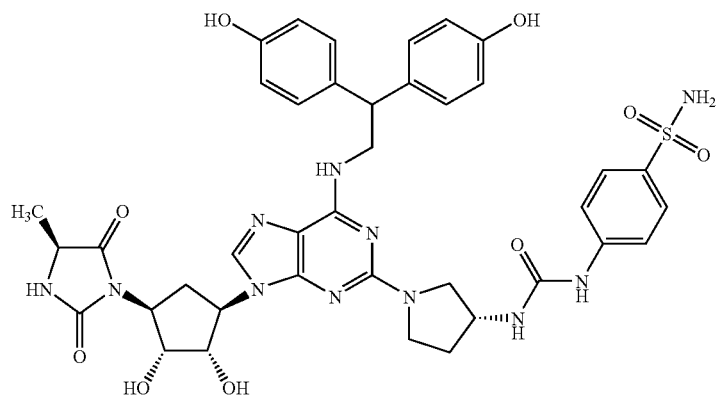 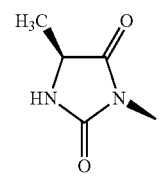

| | | |
|---|---|---|
| C13 | 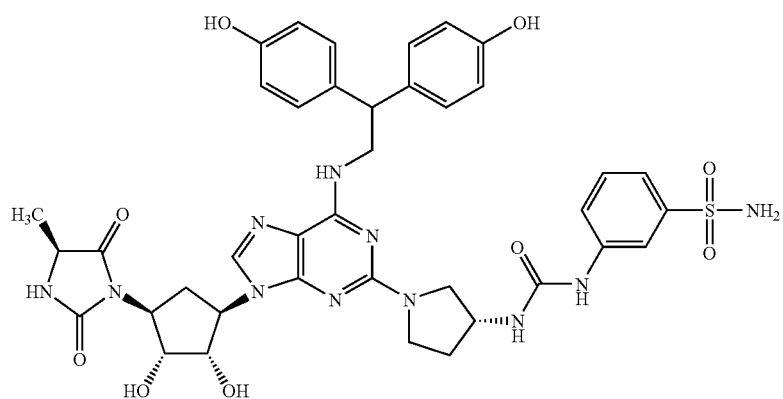 | 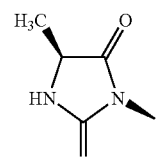 |
| C14 | 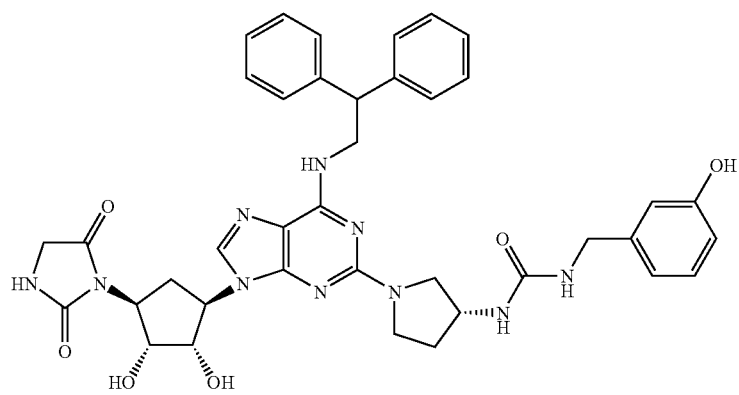 | 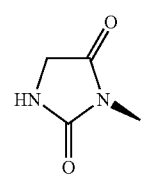 |
| C15 | 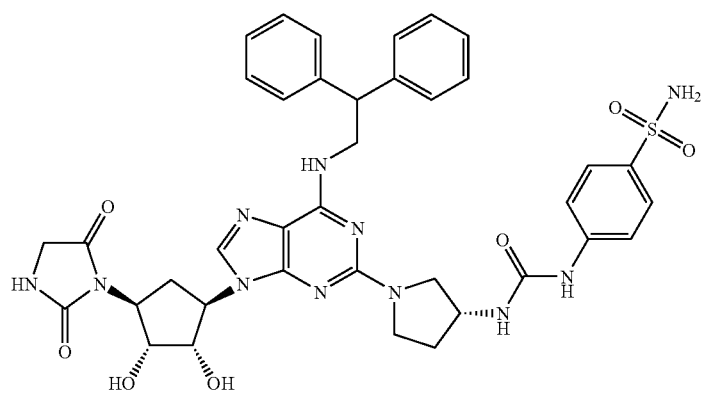 | 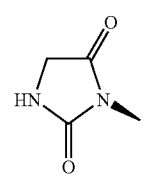 |
| C16 | 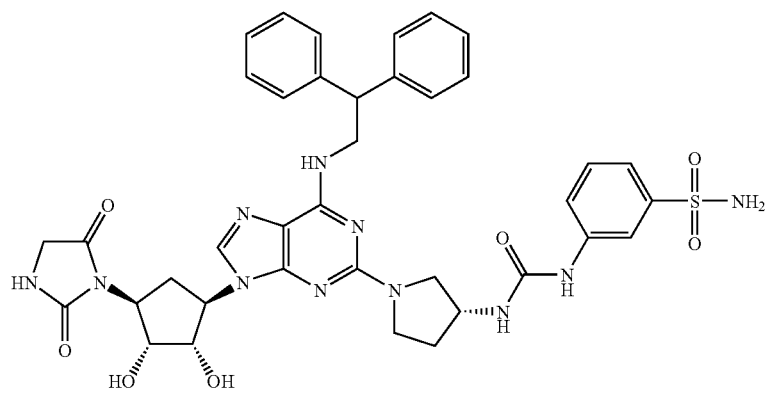 | 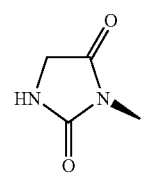 |

| | 95 | 96 |
|---|---|---|
| C17 | 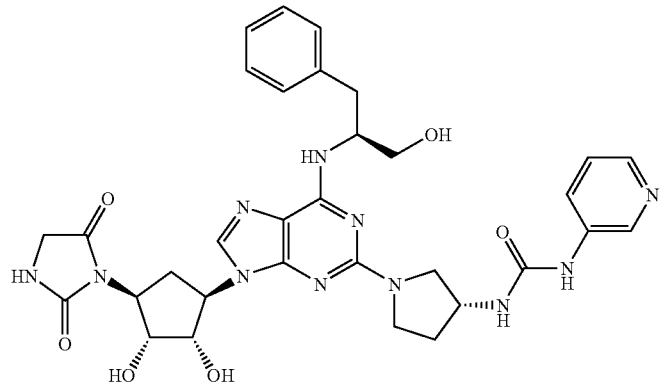 | 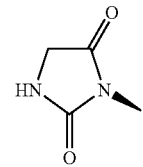 |
| C18 | 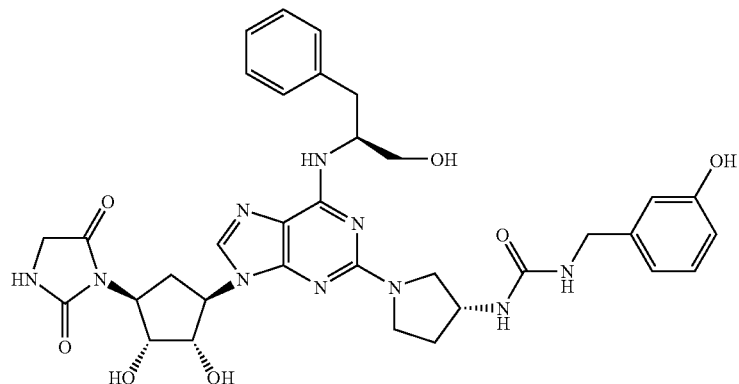 | 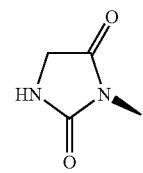 |
| C19 | 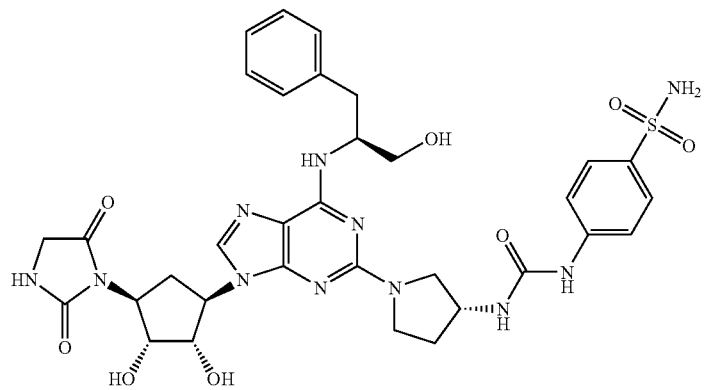 | 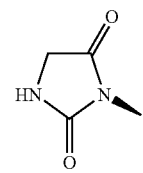 |
| C20 | 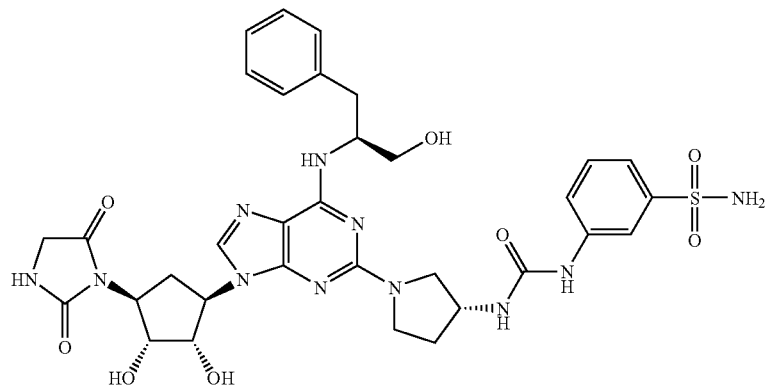 | 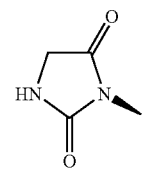 |

| | | |
|---|---|---|
| C21 | 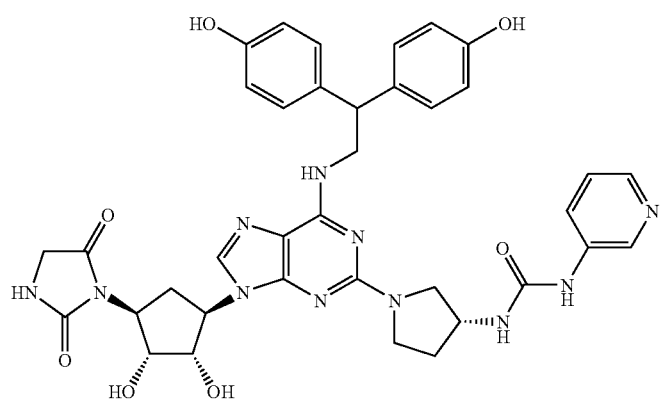 | 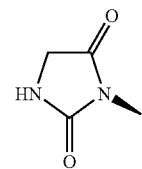 |
| C22 | 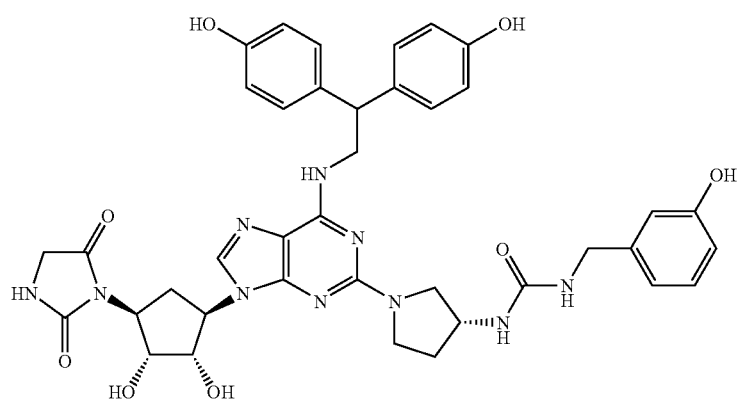 | 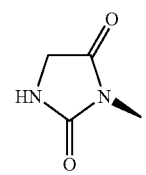 |
| C23 | 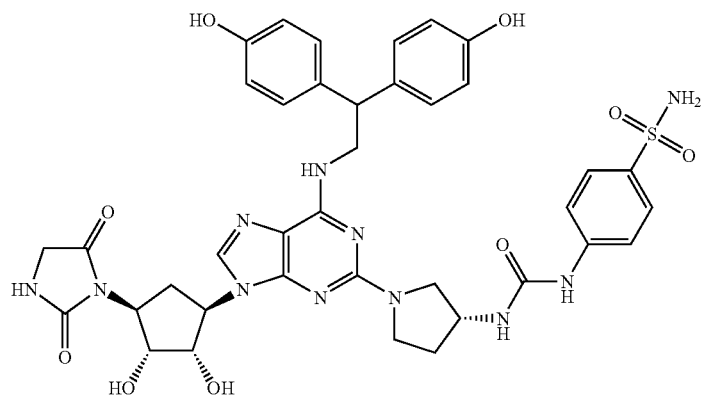 | 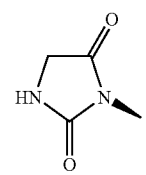 |
| C24 | 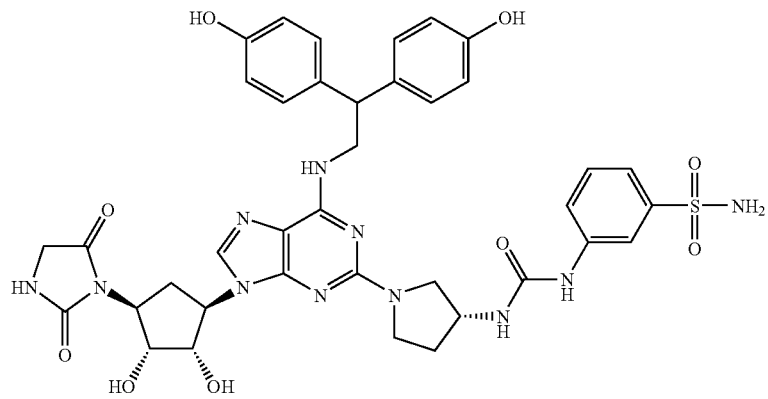 | 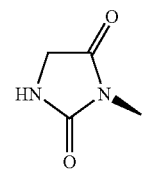 |

-continued
C25 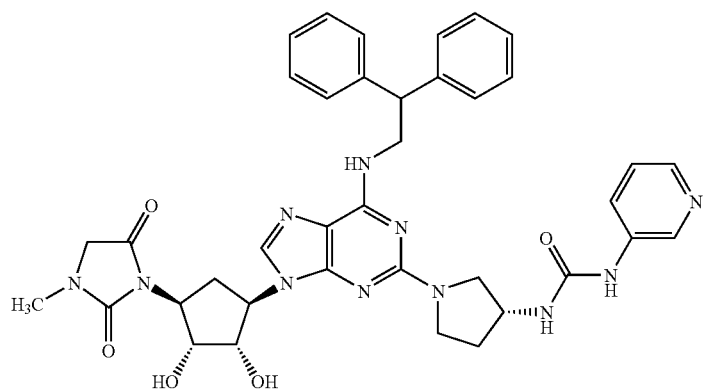 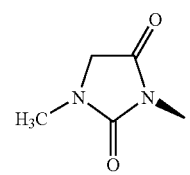
C26 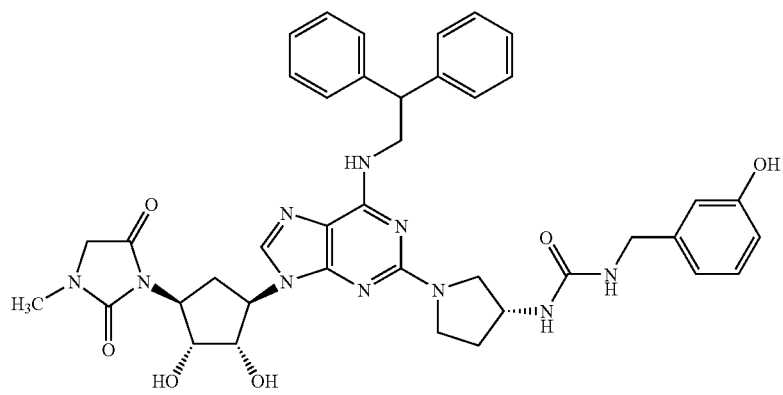 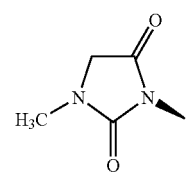
C27 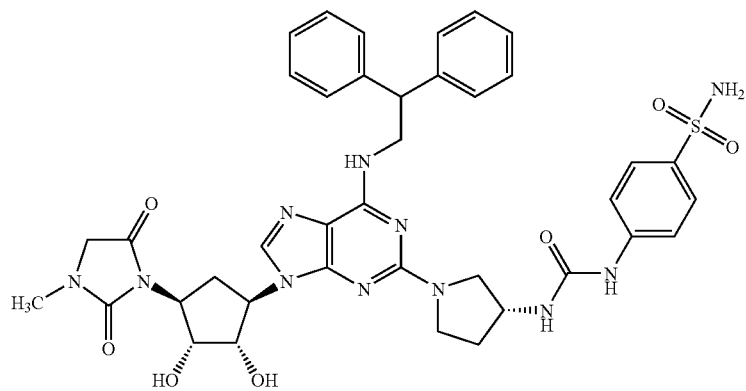 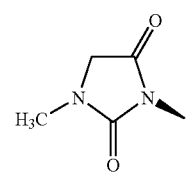
C28 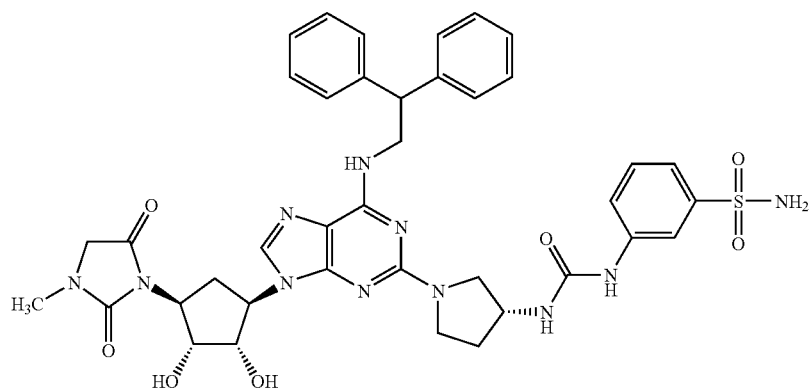 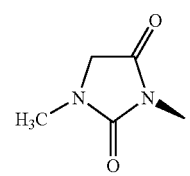

| 101 | 102 |
|---|---|
| C29 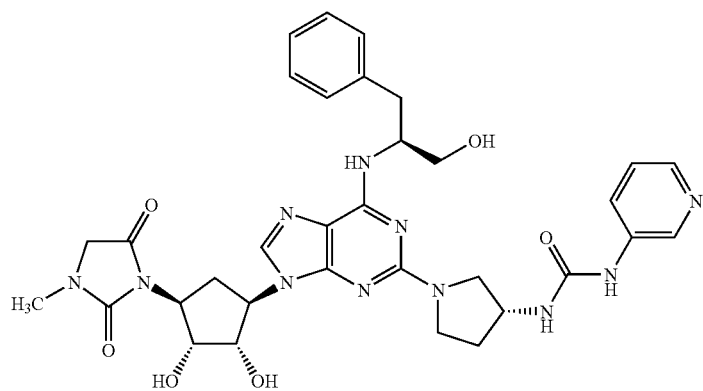 | 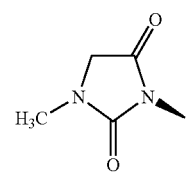 |
| C30 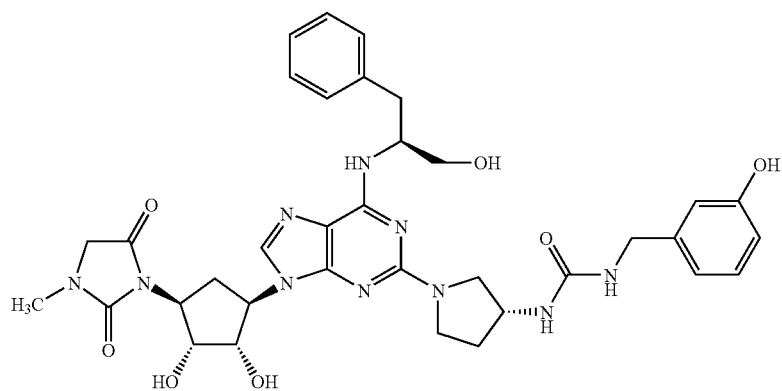 | 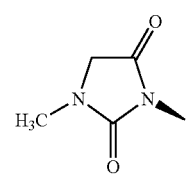 |
| C31 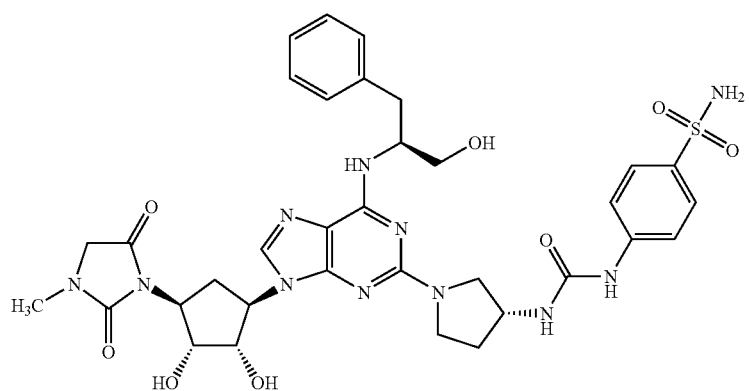 | 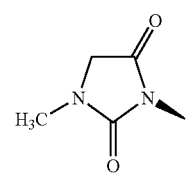 |
| C32 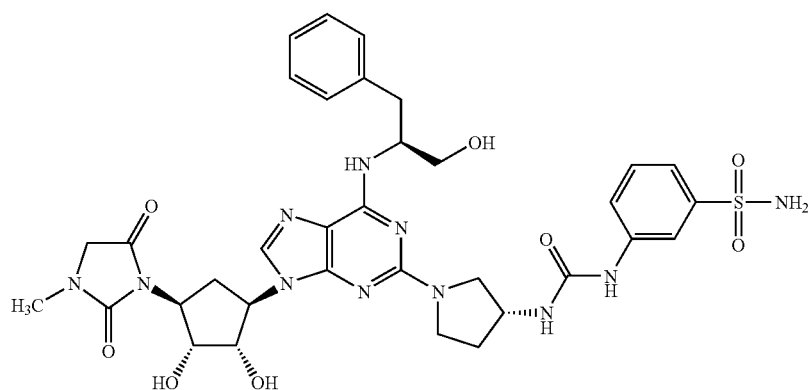 | 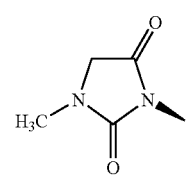 |

-continued
| | 103 | 104 |
|---|---|---|
| C33 | 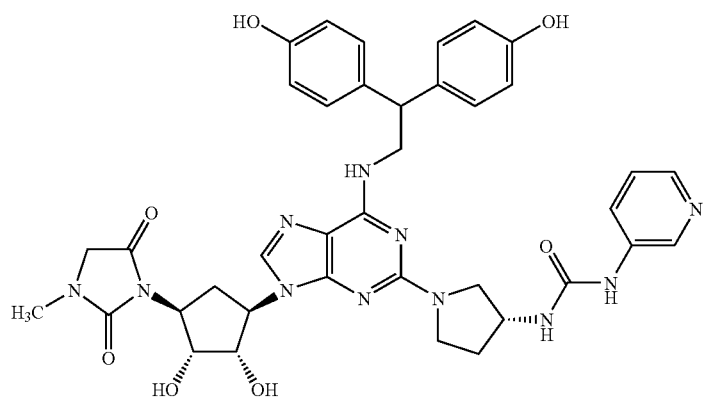 | 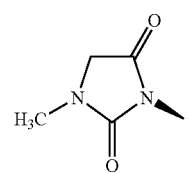 |
| C34 | 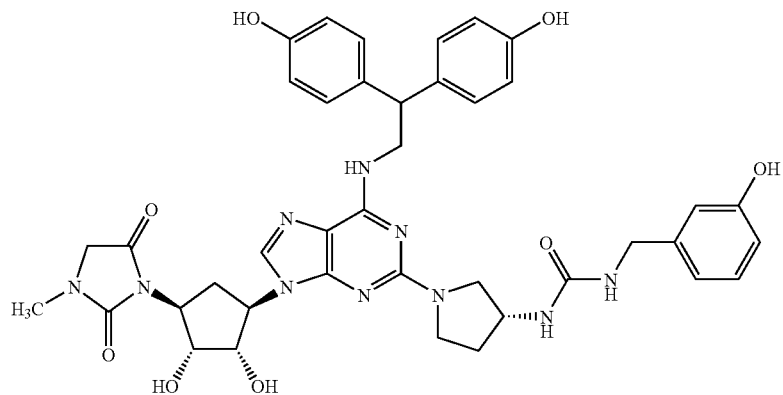 | 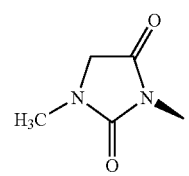 |
| C35 | 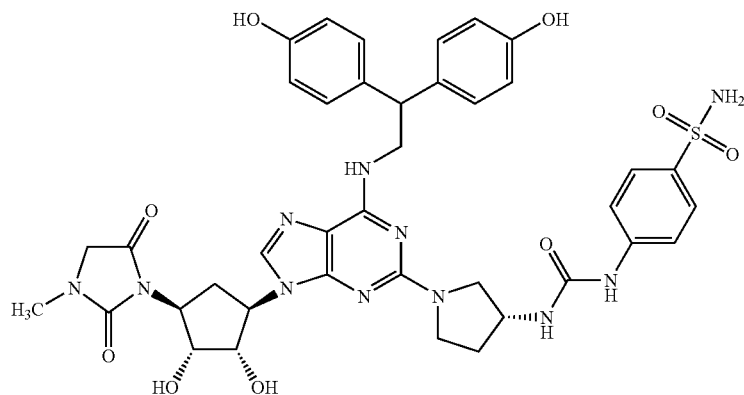 | 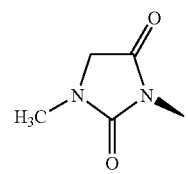 |
| C36 | 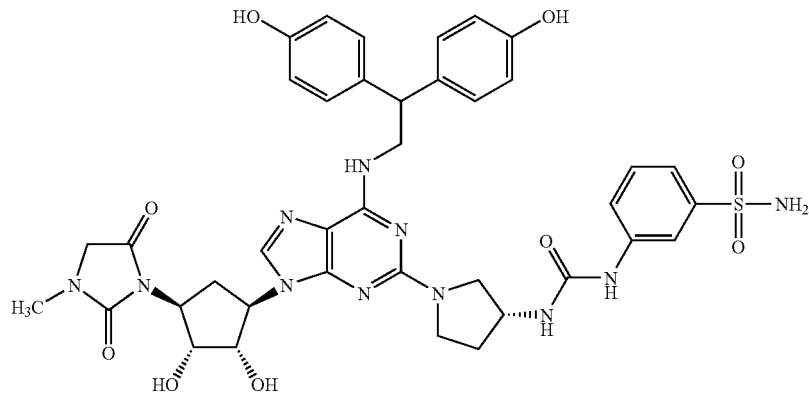 | 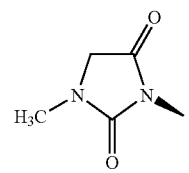 |

| 105 | 106 |
|---|---|
| C37 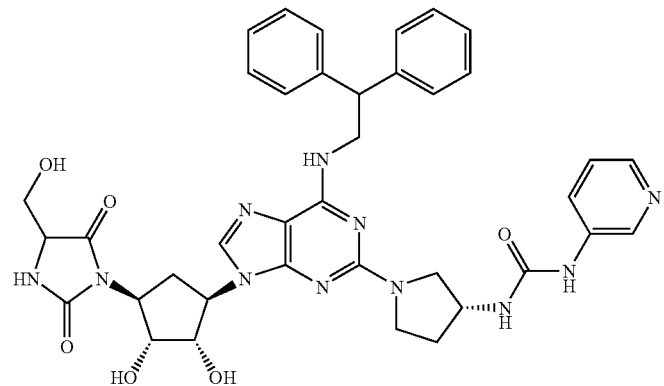 | 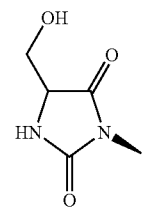 |
| C38 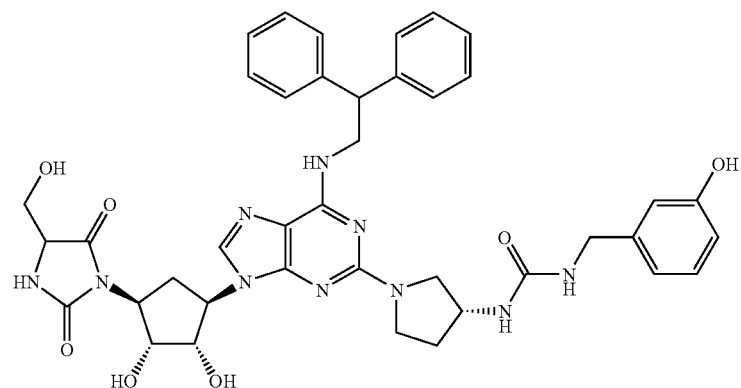 | 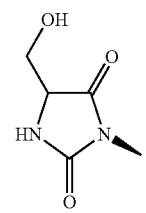 |
| C39 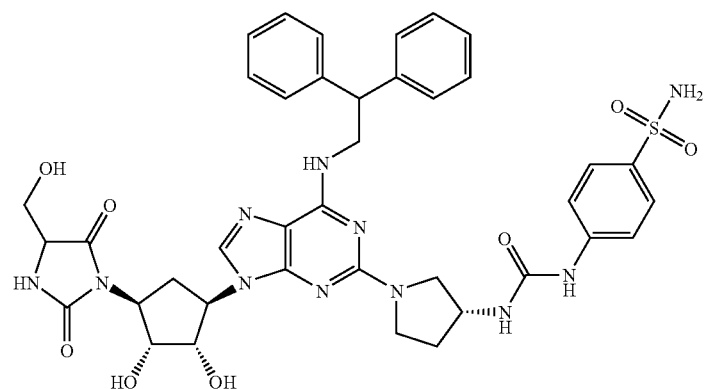 | 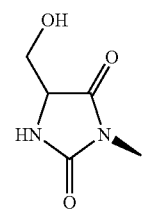 |
| C40 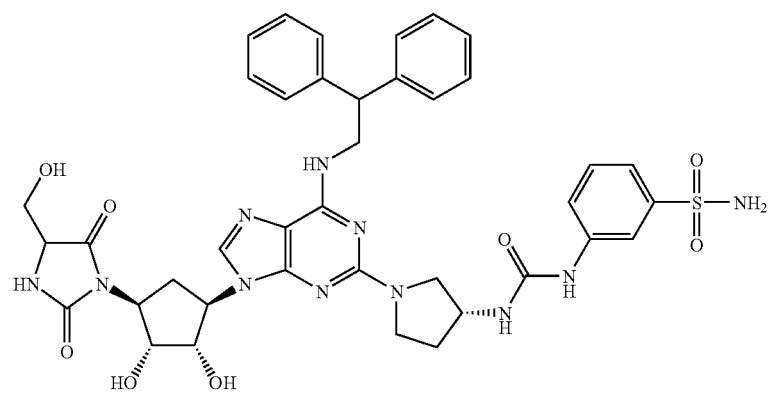 | 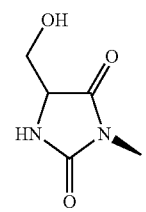 |

-continued
| | 107 | 108 |
|---|---|---|
| C41 | 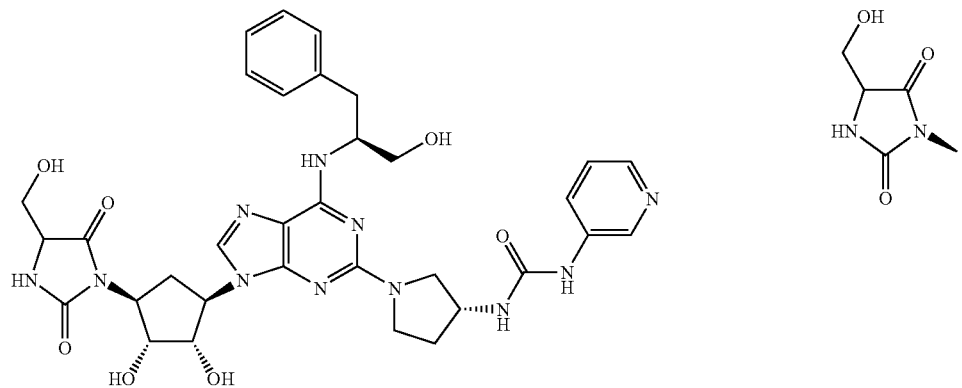 | |
| C42 | 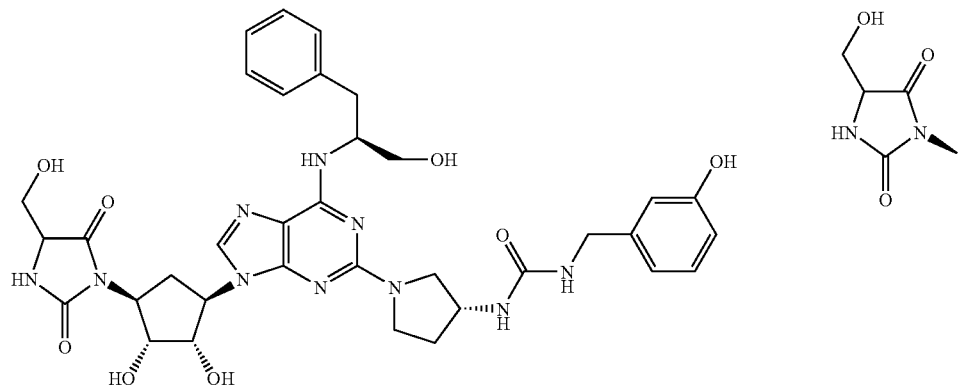 | |
| C43 | 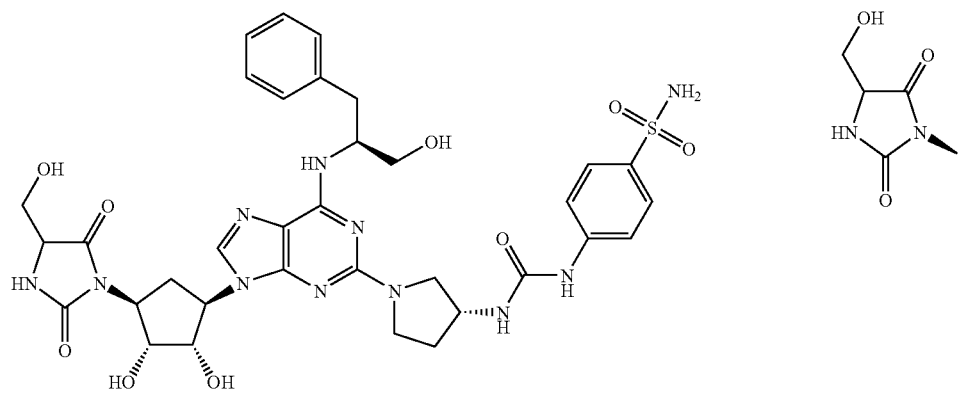 | |
| C44 | 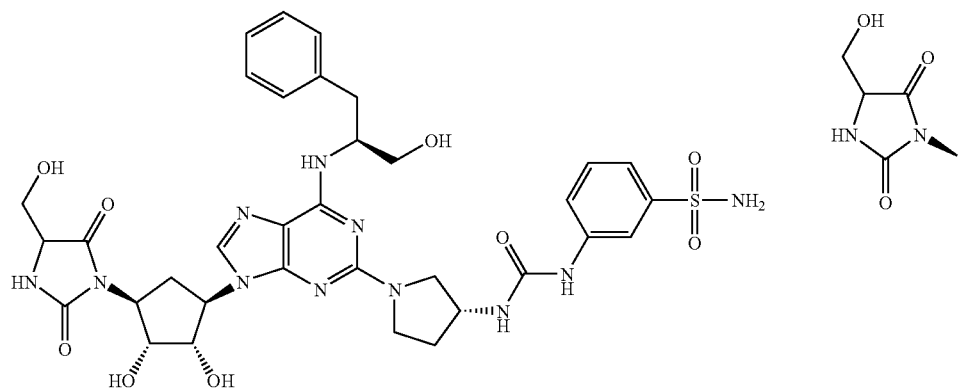 | |

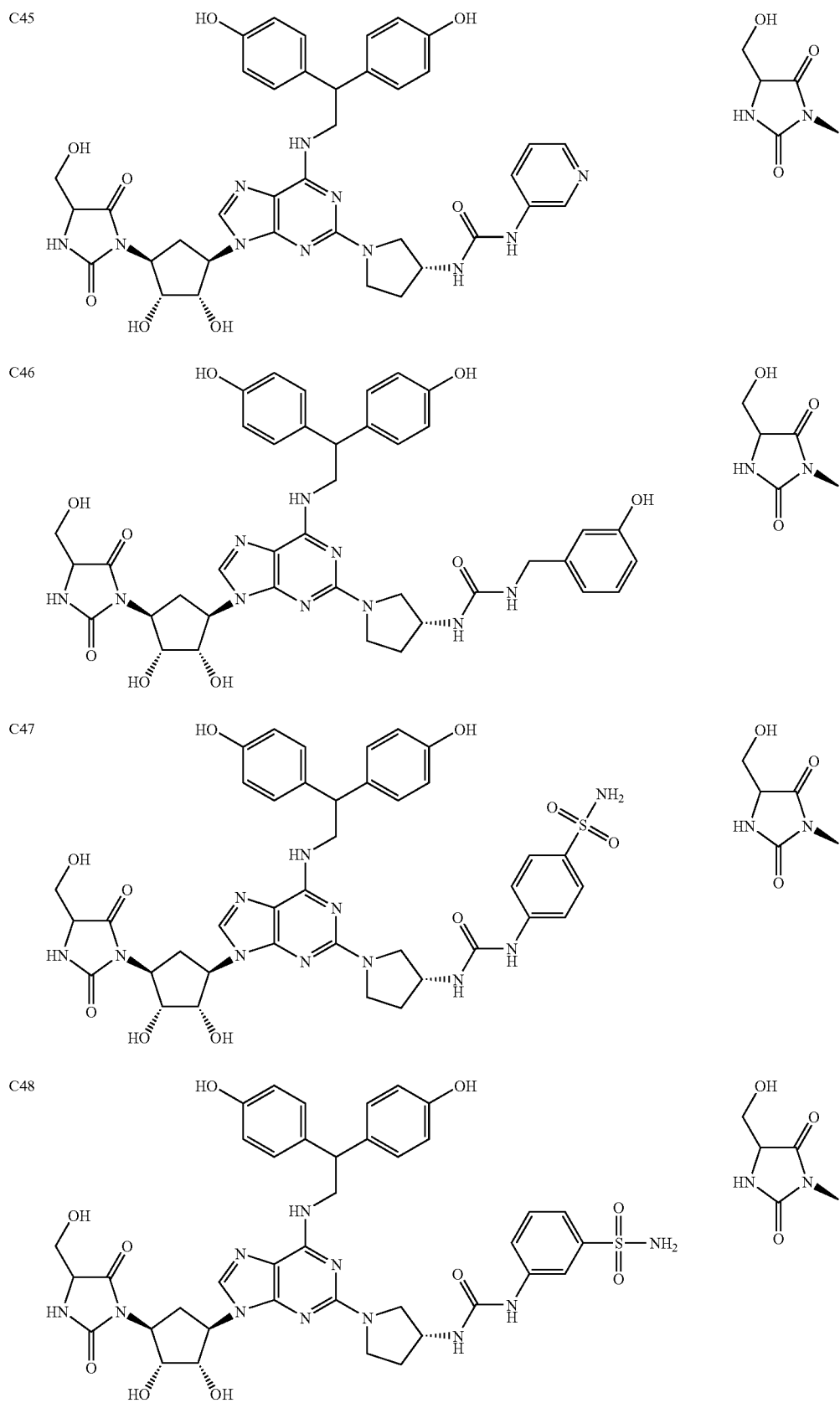

| 111 | 112 |
|---|---|
| C49 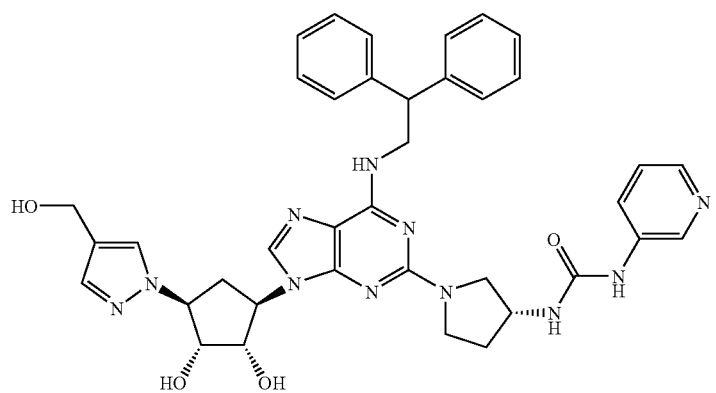 | 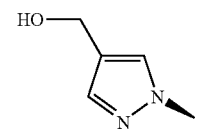 |
| C50 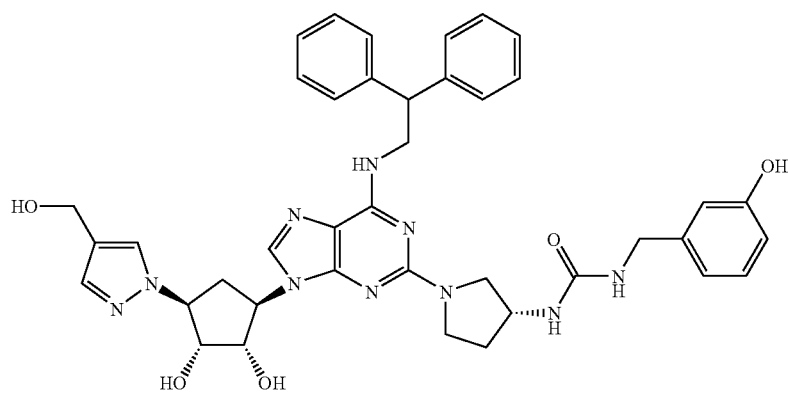 | 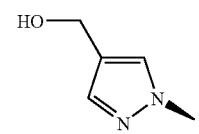 |
| C51 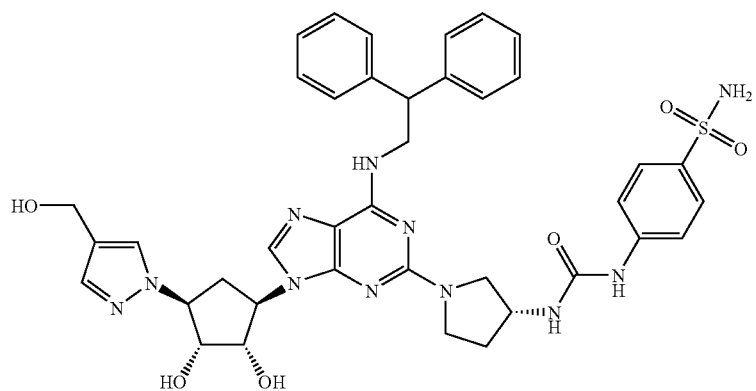 | 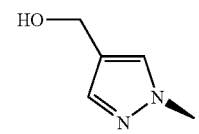 |
| C52 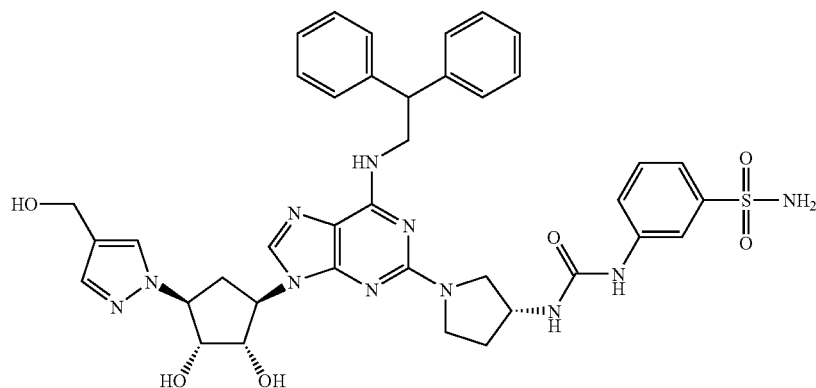 | 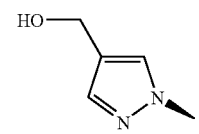 |

| | 113 | 114 |
|---|---|---|
| C53 | 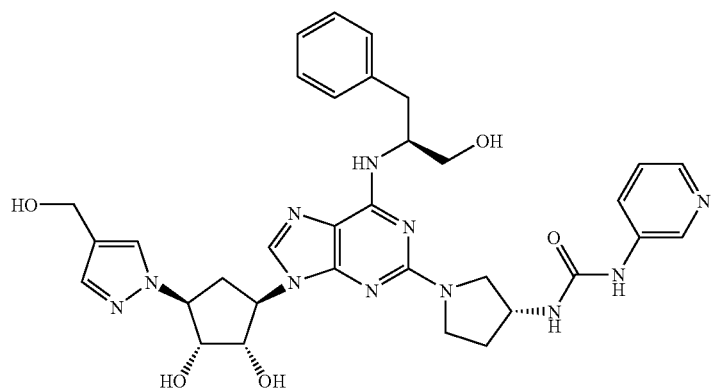 | 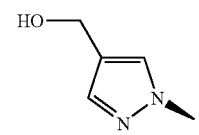 |
| C54 | 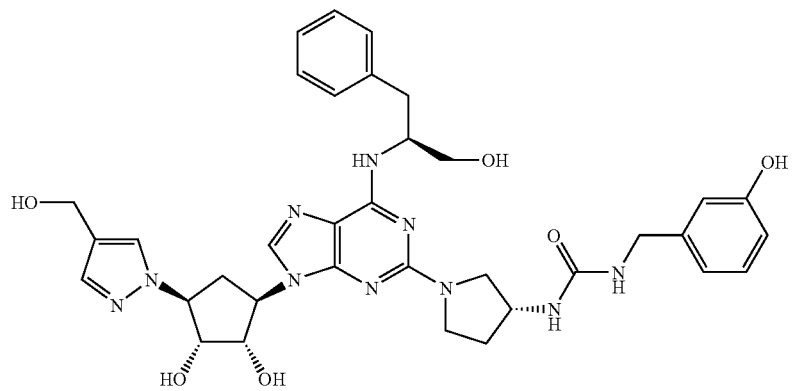 | 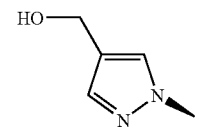 |
| C55 | 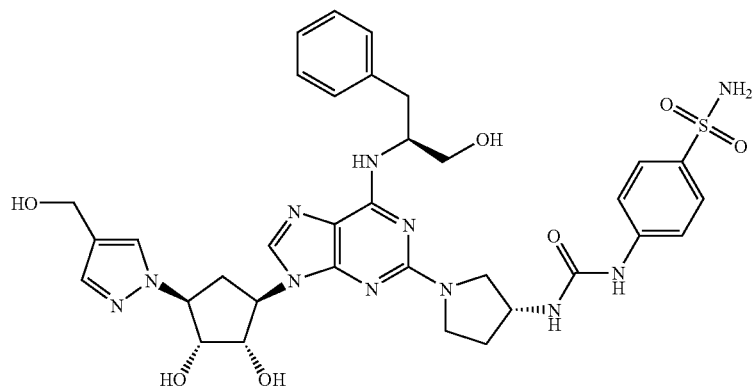 | 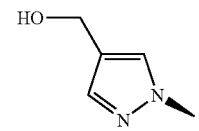 |
| C56 | 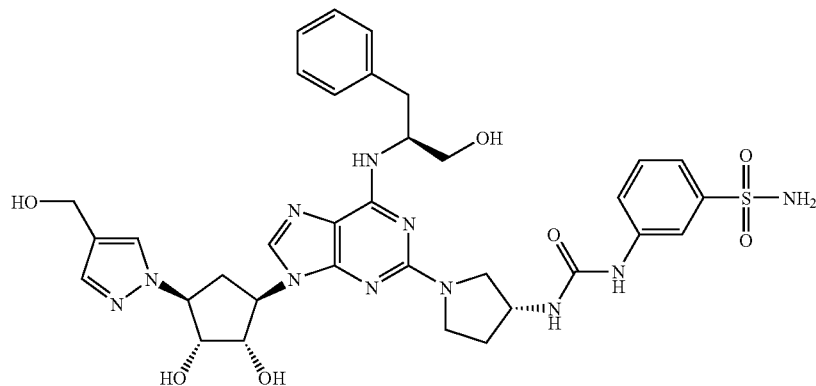 | 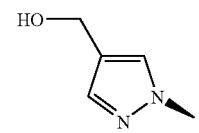 |

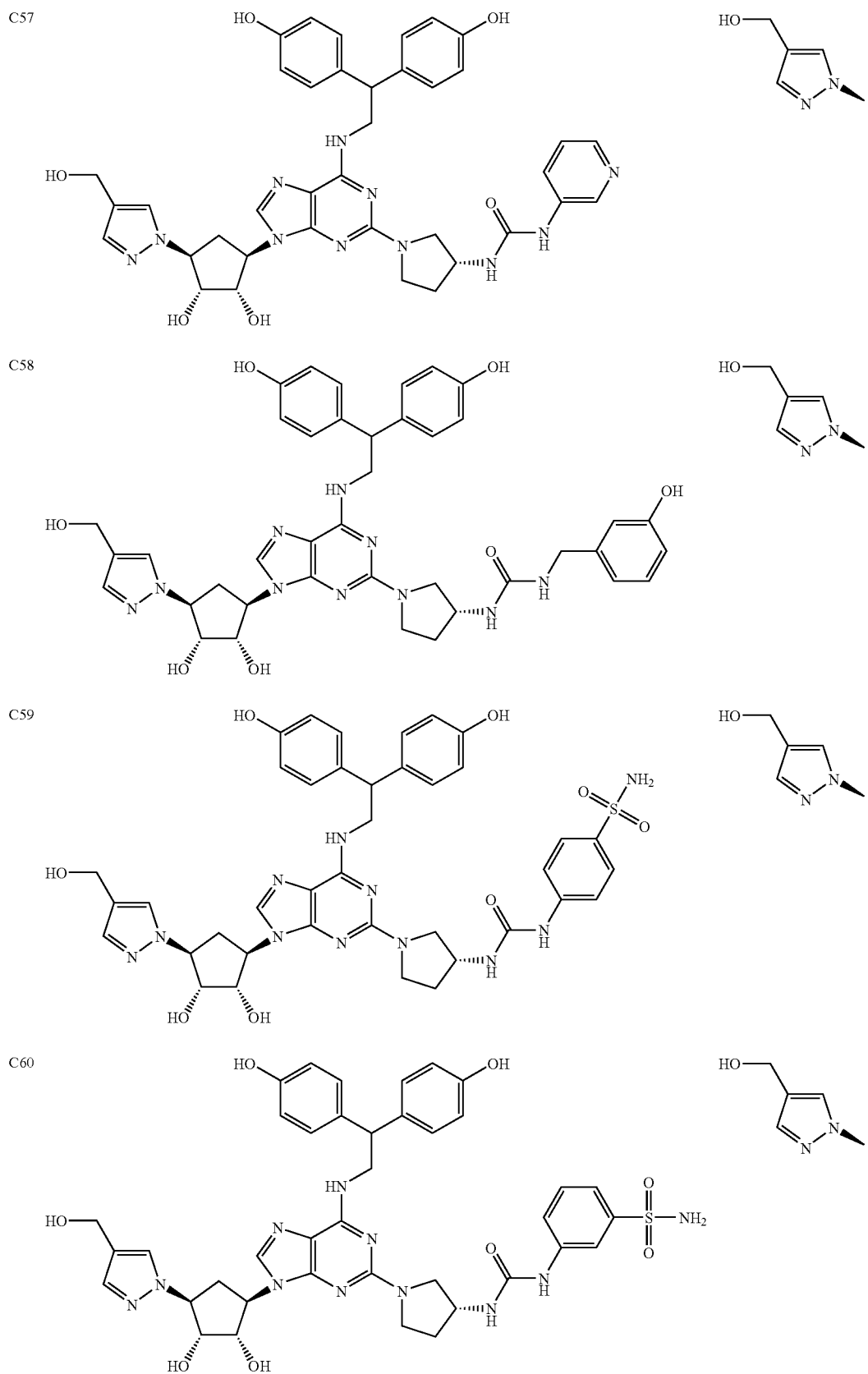

| | |
|---|---|
| C61 | 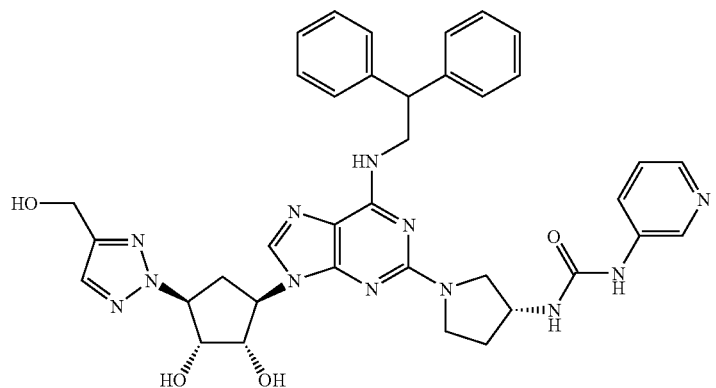 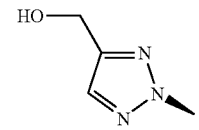 |
| C62 | 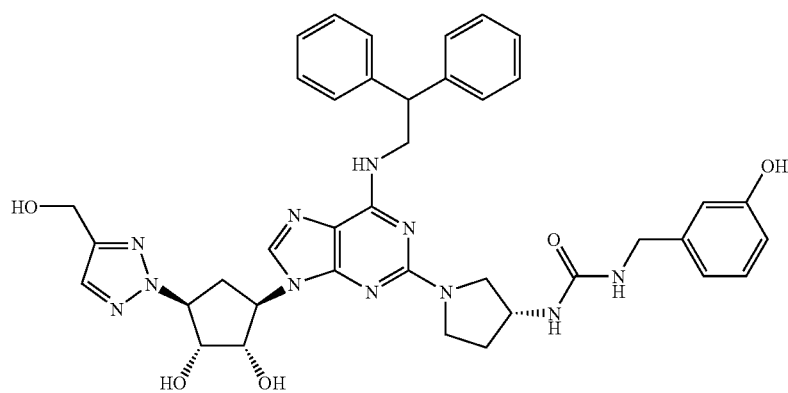 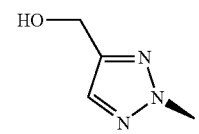 |
| C63 | 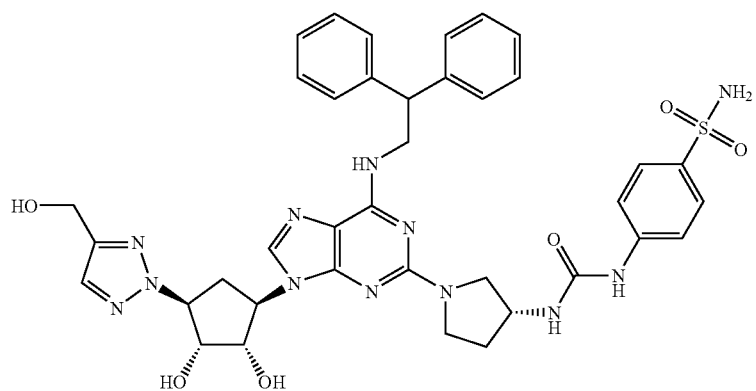 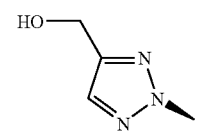 |
| C64 | 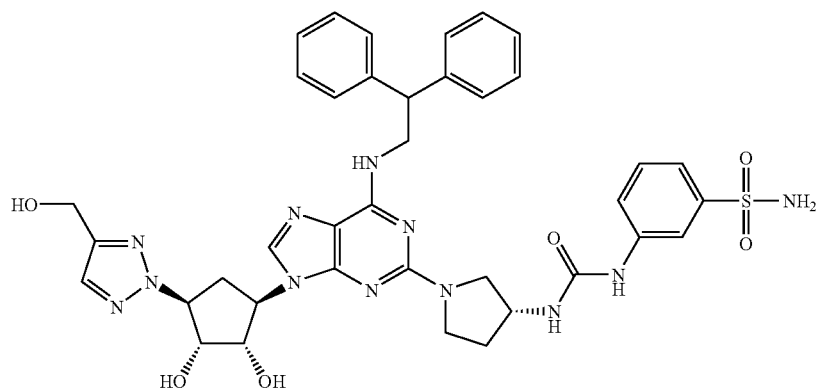 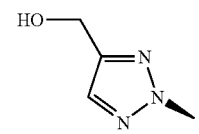 |

-continued
C65 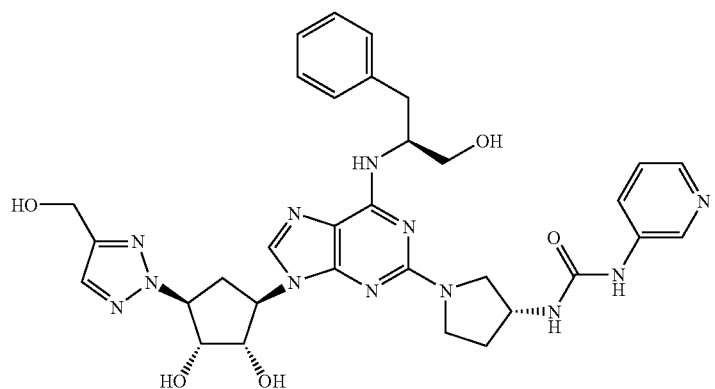 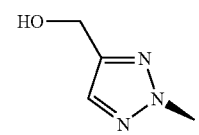
C66 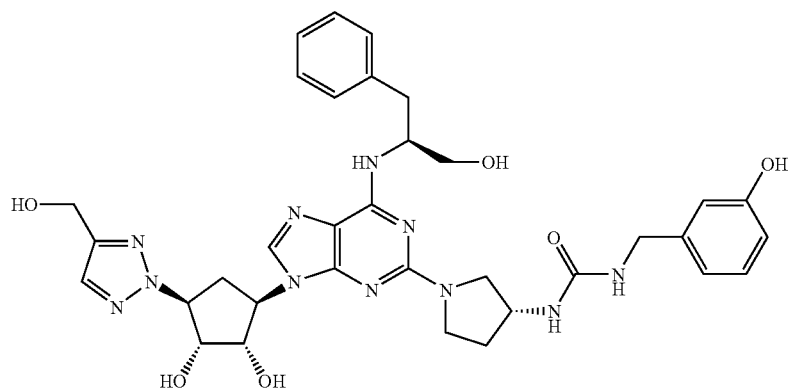 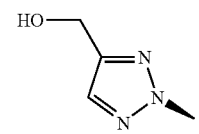
C67 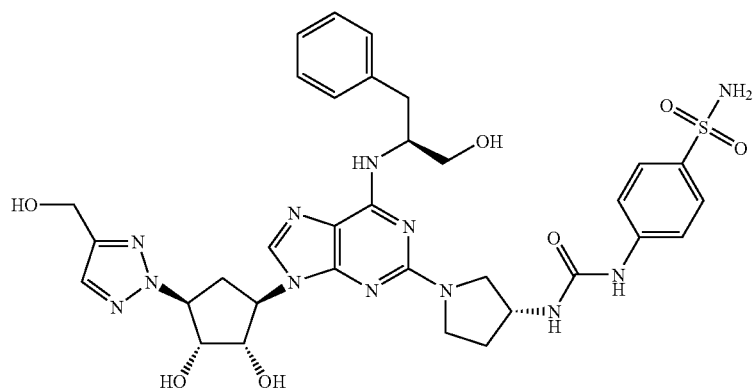 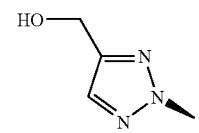
C68 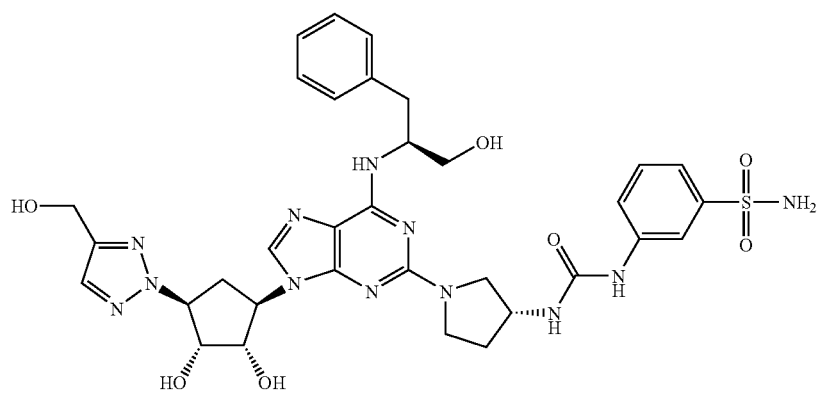 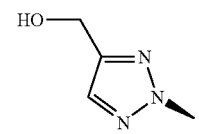

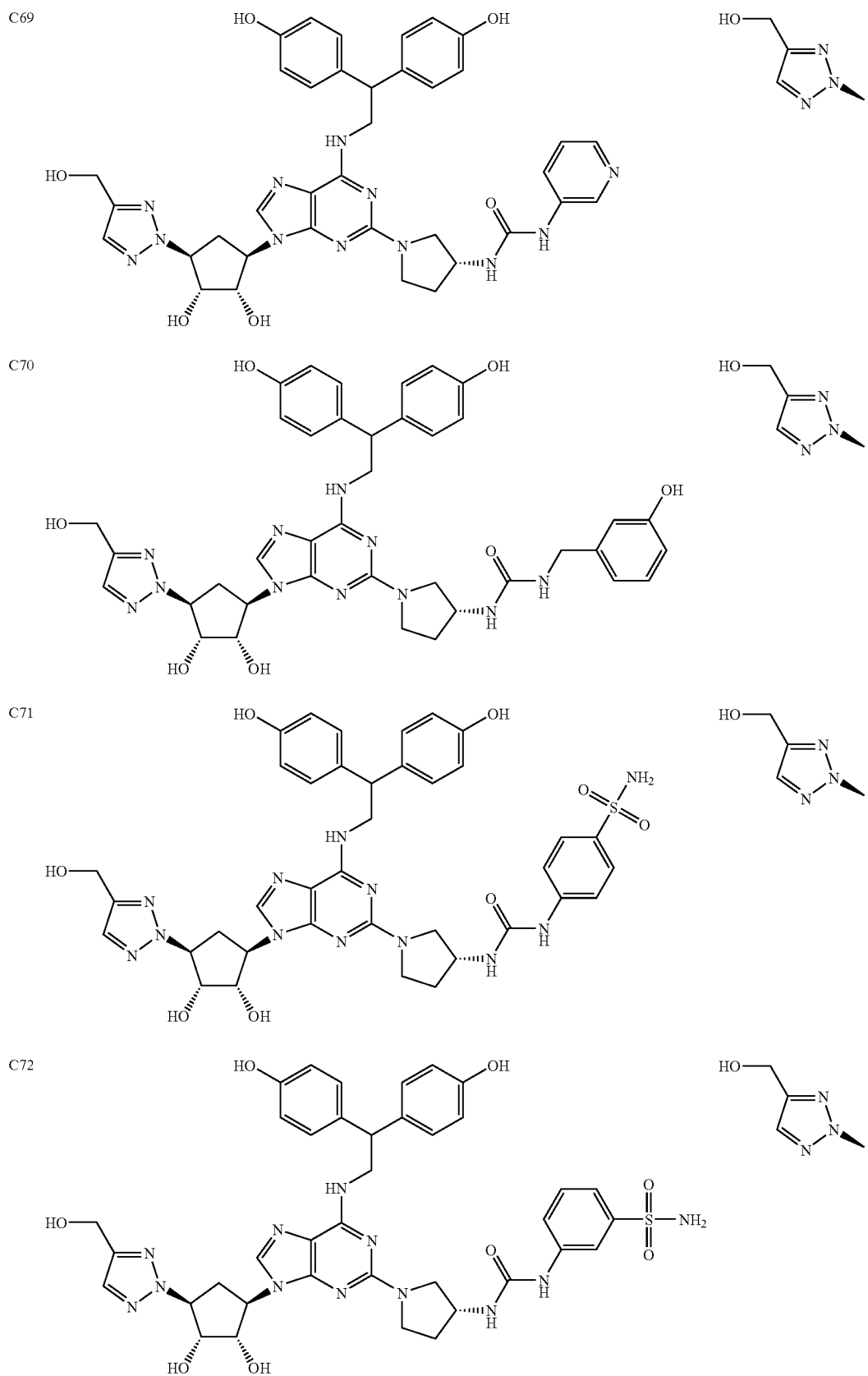

| 123 | 124 |
|---|---|
| C73 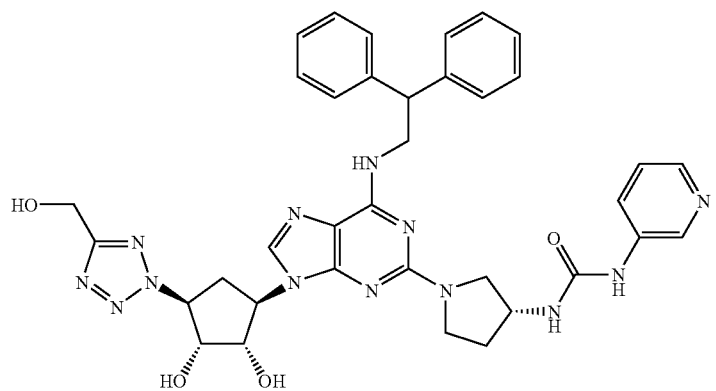 | 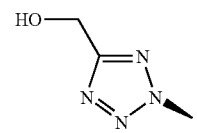 |
| C74 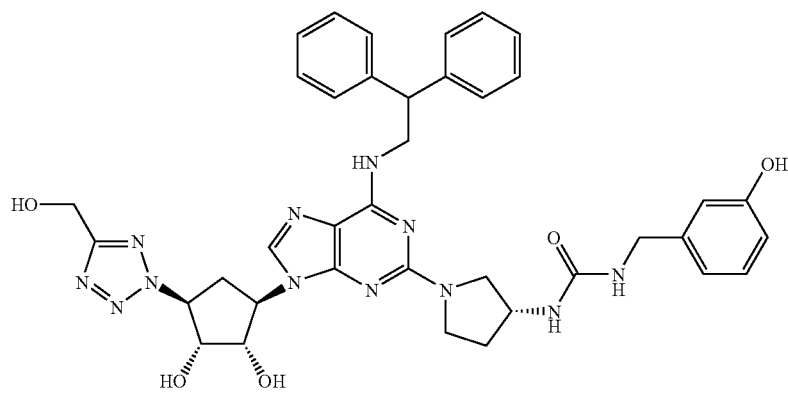 | 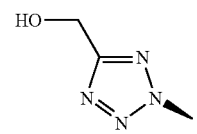 |
| C75 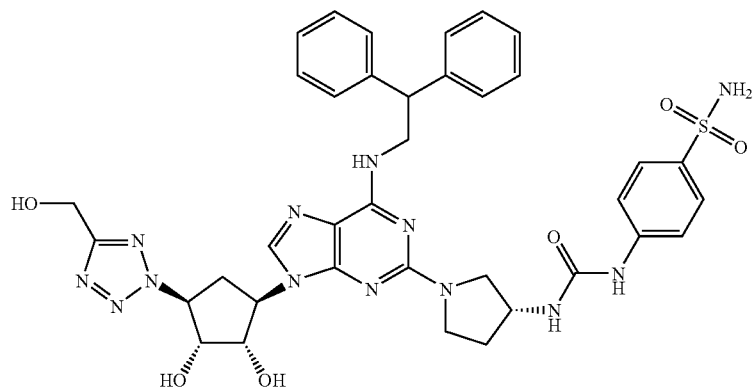 | 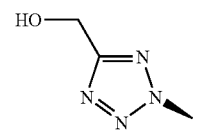 |
| C76 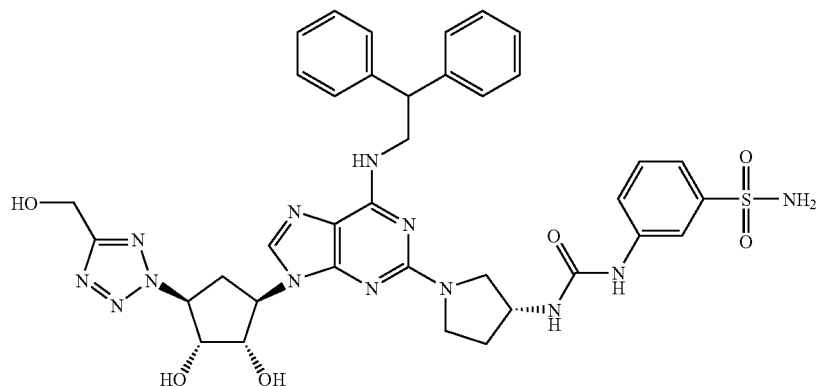 | 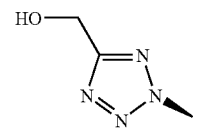 |

-continued
C77 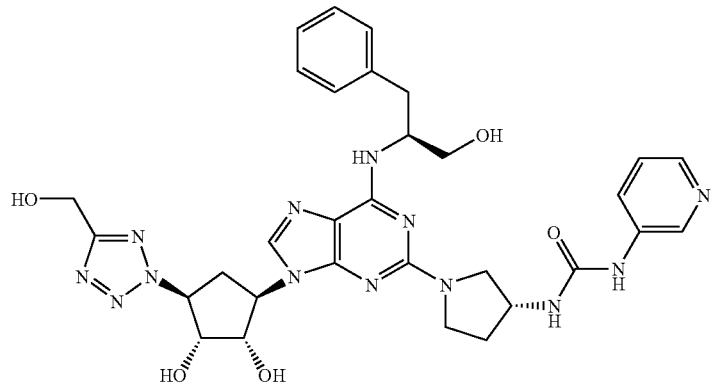 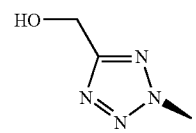
C78 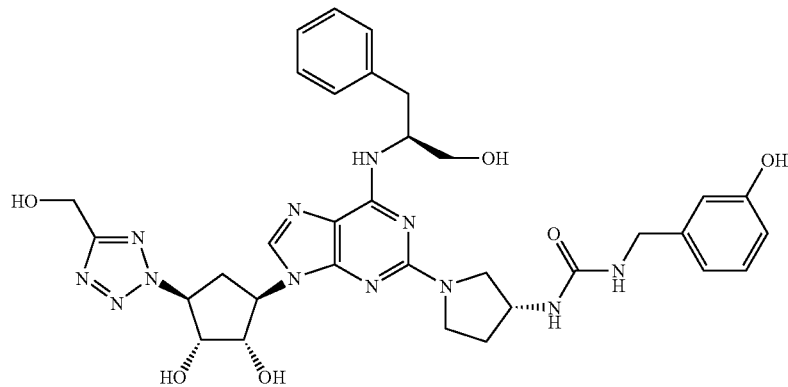 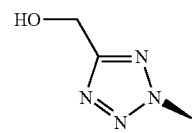
C79 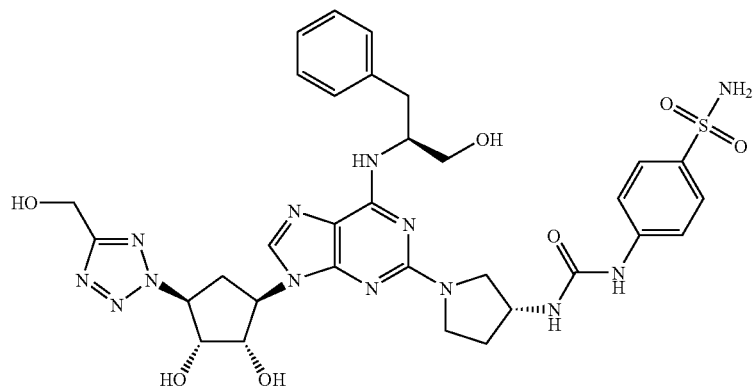 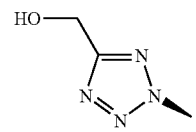
C80 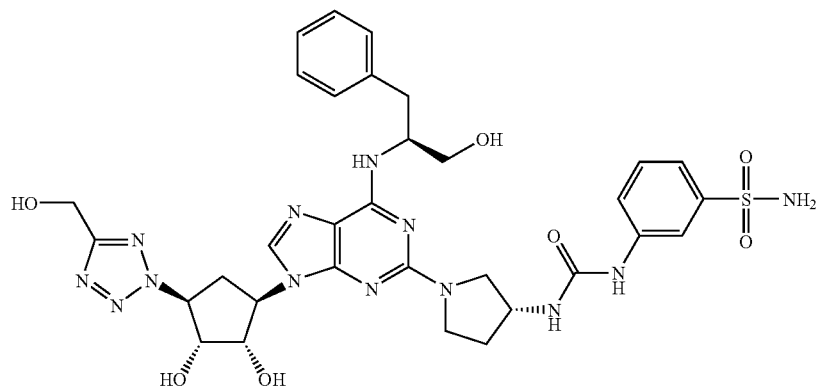 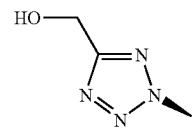

-continued
C81 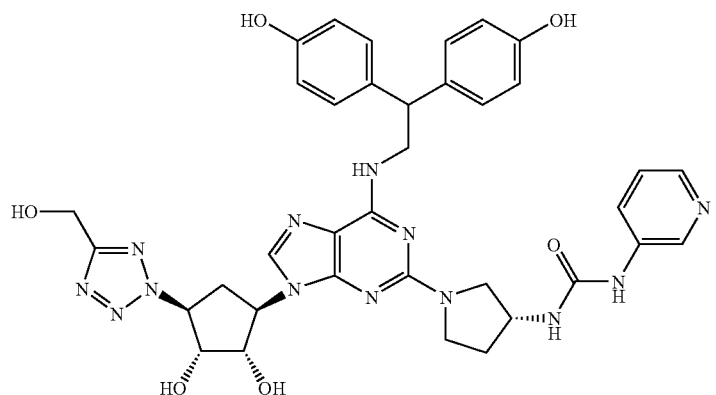 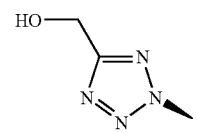
C82 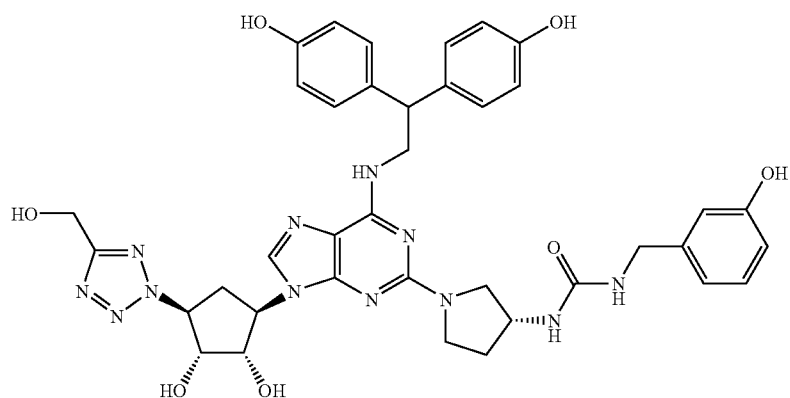 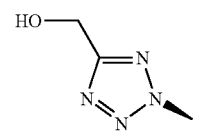
C83 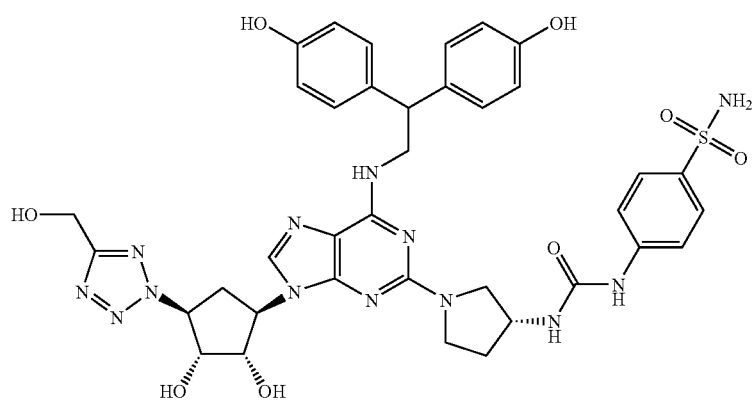 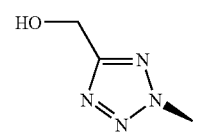
C84 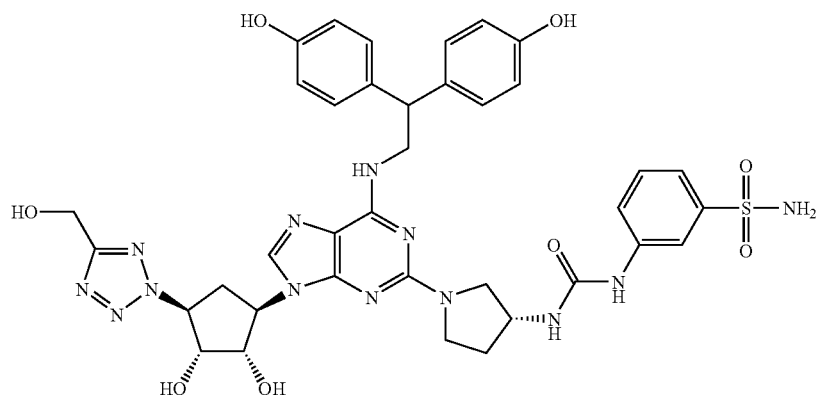 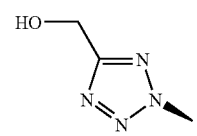

-continued

C85 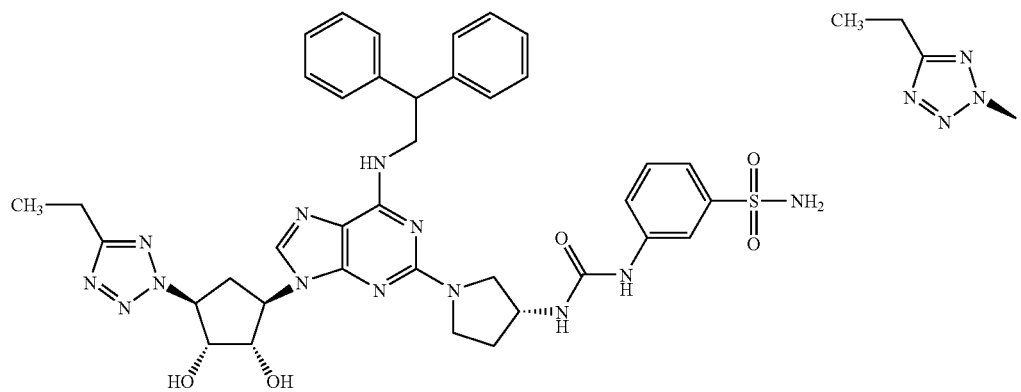

| Ex. | R² | R³ | Name |
|---|---|---|---|
| C1 | 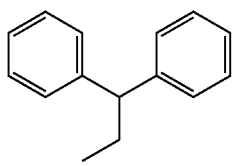 | 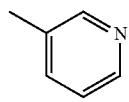 | 1-{(R)-1-[9-[(1R,2S,3R,4S)-2,3-Dihydroxy-4-((S)-4-methyl-2,5-dioxo-imidazolidin-1-yl)-cyclopentyl]-6-(2,2-diphenyl-ethylamino)-9H-purin-2-yl]-pyrrolidin-3-yl}-3-pyridin-3-yl-urea |
| C2 | 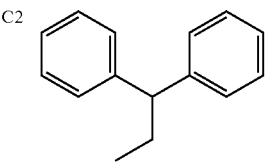 | 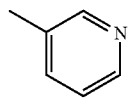 | 1-{(R)-1-[9-[(1R,2S,3R,4S)-4-(2,5-Dioxo-imidazolidin-1-yl)-2,3-dihydroxy-cyclopentyl]-6-(2,2-diphenyl-ethylamino)-9H-purin-2-yl]-pyrrolidin-3-yl}-3-pyridin-3-yl-urea |
| C3 | 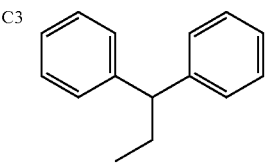 | 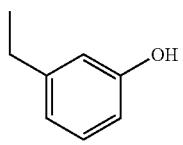 | 1-{(R)-1-[9-[(1R,2S,3R,4S)-2,3-Dihydroxy-4-((S)-4-methyl-2,5-dioxo-imidazolidin-1-yl)-cyclopentyl]-6-(2,2-diphenyl-ethylamino)-9H-purin-2-yl]-pyrrolidin-3-yl}-3-(3-hydroxy-benzyl)-urea |
| C4 | 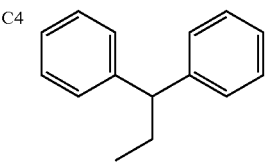 | 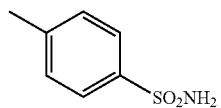 | 4-(3-{(R)-1-[9-[(1R,2S,3R,4S)-2,3-Dihydroxy-4-((S)-4-methyl-2,5-dioxo-imidazolidin-1-yl)-cyclopentyl]-6-(2,2-diphenyl-ethylamino)-9H-purin-2-yl]-pyrrolidin-3-yl}-ureido)-benzenesulfonamide |
| C5 | 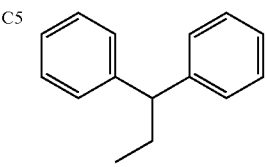 | 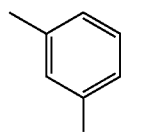 | 3-(3-{(R)-1-[9-[(1R,2S,3R,4S)-2,3-Dihydroxy-4-((S)-4-methyl-2,5-dioxo-imidazolidin-1-yl)-cyclopentyl]-6-(2,2-diphenyl-ethylamino)-9H-purin-2-yl]-pyrrolidin-3-yl}-ureido)-benzenesulfonamide |

-continued

| | | | |
|---|---|---|---|
| C6 | 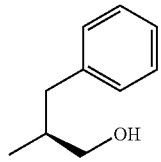 | 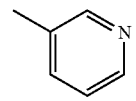 | 1-{(R)-1-[9-[(1R,2S,3R,4S)-2,3-Dihydroxy-4-((S)-4-methyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-3-pyridin-3-yl-urea |
| C7 | 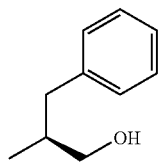 | 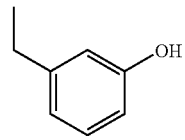 | 1-{(R)-1-[9-[(1R,2S,3R,4S)-2,3-Dihydroxy-4-((S)-4-methyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-3-(3-hydroxy-benzyl)-urea |
| C8 | 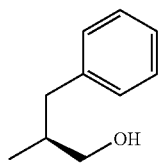 | 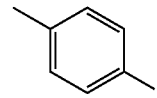 | 4-(3-{(R)-1-[9-[(1R,2S,3R,4S)-2,3-Dihydroxy-4-((S)-4-methyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-ureido)-benzenesulfonamide |
| C9 | 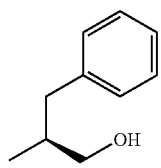 | 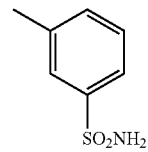 | 3-(3-{(R)-1-[9-[(1R,2S,3R,4S)-2,3-Dihydroxy-4-((S)-4-methyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-ureido)-benzenesulfonamide |
| C10 | 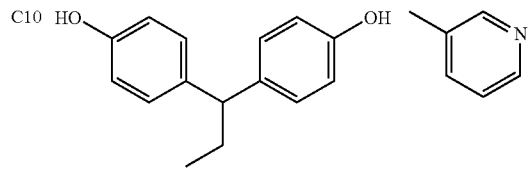 | | 1-((R)-1-{6-[2,2-Bis-(4-hydroxy-phenyl)-ethylamino]-9-[1R,2S,3R,4S)-2,3-dihydroxy-4-((S)-4-methyl-2,5-dioxo-imidazolidin-1-yl)-cyclopentyl]-9H-purin-2-yl}-pyrrolidin-3-yl)-3-pyridin-3-yl-urea |
| C11 | 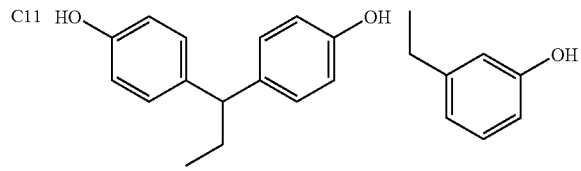 | | 1-((R)-1-{6-(2,2-Bis-(4-hydroxy-phenyl)-ethylamino]-9-[(1R,2S,3R,4S)-2,3-dihydroxy-4-((S)-4-methyl-2,5-dioxo-imidazolidin-1-yl)-cyclopentyl]-9H-purin-2-yl}-pyrrolidin-3-yl)-3-(3-hydroxy-benzyl)-urea |

-continued

| | | | |
|---|---|---|---|
| C12 | (structure: 1,1-bis(4-hydroxyphenyl)propyl) | (structure: 4-methyl-benzenesulfonamide) | 4-[3-((R)-1-{6-[2,2-Bis-(4-hydroxy-phenyl)-ethylamino]-9-[(1R,2S,3R,4S)-2,3-dihydroxy-4-((S)-4-methyl-2,5-dioxo-imidazolidin-1-yl)-cyclopentyl]-9H-purin-2-yl}-pyrrolidin-3-yl)-ureido]-benzenesulfonamide |
| C13 | (structure: 1,1-bis(4-hydroxyphenyl)propyl) | (structure: 3-methyl-benzenesulfonamide) | 3-[3-((R)-1-{6-[2,2-Bis-(4-hydroxy-phenyl)-ethylamino]-9-[(1R,2S,3R,4S)-2,3-dihydroxy-4-((S)-4-methyl-2,5-dioxo-imidazolidin-1-yl)-cyclopentyl]-9H-purin-2-yl}-pyrrolidin-3-yl)-ureido]-benzenesulfonamide |
| C14 | (structure: 1,1-diphenylpropyl) | (structure: 3-hydroxy-methylbenzene) | 1-{(R)-1-[9-[(1R,2S,3R,4S)-4-(2,5-Dioxo-imidazolidin-1-yl)-2,3-dihydroxy-cyclopentyl]-6-(2,2-diphenyl-ethylamino)-9H-purin-2-yl]-pyrrolidin-3-yl}-3-(3-hydroxy-benzyl)-urea |
| C15 | (structure: 1,1-diphenylpropyl) | (structure: 4-methyl-benzenesulfonamide) | 4-(3-{(R)-1-[9-[(1R,2S,3R,4S)-4-(2,5-Dioxo-imidazolidin-1-yl)-2,3-dihydroxy-cyclopentyl]-6-(2,2-diphenyl-ethylamino)-9H-purin-2-yl]-pyrrolidin-3-yl}-ureido)-benzenesulfonamide |
| C16 | (structure: 1,1-diphenylpropyl) | (structure: 3-methyl-benzenesulfonamide) | 3-(3-{(R)-1-[9-[(1R,2S,3R,4S)-4-(2,5-Dioxo-imidazolidin-1-yl)-2,3-dihydroxy-cyclopentyl]-6-(2,2-diphenyl-ethylamino)-9H-purin-2-yl]-pyrrolidin-3-yl}-ureido)-benzenesulfonamide |
| C17 | (structure: (S)-2-methyl-3-phenyl-propan-1-ol) | (structure: 3-methyl-pyridine) | 1-{(R)-1-[9-[(1R,2S,3R,4S)-4-(2,5-Dioxo-imidazolidin-1-yl)-2,3-dihydroxy-cyclopentyl]-6-((S)-1-hydroxymethyl-2-phenyl-ethylamino)-9H-purin-2-yl]-pyrrolidin-3-yl}-3-pyridin-3-yl-urea |

| | | | |
|---|---|---|---|
| C18 | 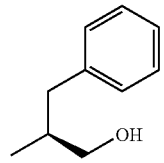 | 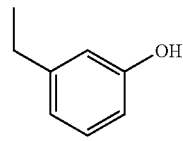 | 1-{(R)-1-[9-[(1R,2S,3R,4S)-4-(2,5-Dioxo-imidazolidin-1-yl)-2,3-dihydroxy-cyclopentyl]-6-((S)-1-hydroxymethyl-2-phenyl-ethylamino)-9H-purin-2-yl]-pyrrolidin-3-yl}-3-(3-hydroxy-benzyl)-urea |
| C19 | 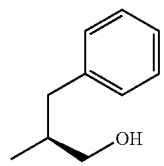 | 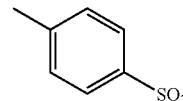 | 4-(3-{(R)-1-[9-[(1R,2S,3R,4S)-4-(2,5-Dioxo-imidazolidin-1-yl)-2,3-dihydroxy-cyclopentyl]-6-((S)-1-hydroxymethyl-2-phenyl-ethylamino)-9H-purin-2-yl]-pyrrolidin-3-yl}-ureido)-benzenesulfonamide |
| C20 | 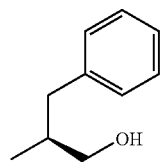 | 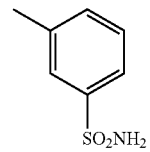 | 3-(3-{(R)-1-[9-[(1R,2S,3R,4S)-4-(2,5-Dioxo-imidazolidin-1-yl)-2,3-dihydroxy-cyclopentyl]-6-((S)-1-hydroxymethyl-2-phenyl-ethylamino)-9H-purin-2-yl]-pyrrolidin-3-yl}-ureido)-benzenesulfonamide |
| C21 | 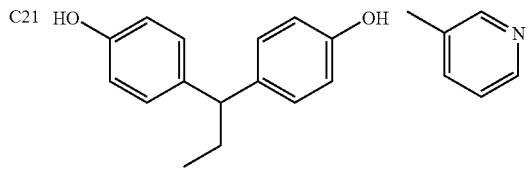 | | 1-((R)-1-{6-[2,2-Bis-(4-hydroxy-phenyl)-ethylamino]-9-[(1R,2S,3R,4S)-4-(2,5-dioxo-imidazolidin-1-yl)-2,3-dihydroxy-cyclopentyl]-9H-purin-2-yl}-pyrrolidin-3-yl)-3-pyridin-3-yl-urea |
| C22 | 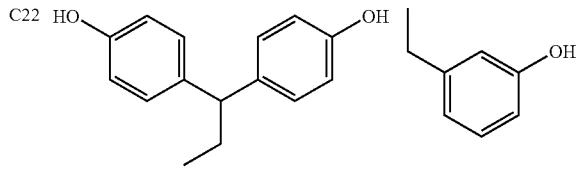 | | 1-((R)-1-{6-[2,2-Bis-(4-hydroxy-phenyl)-ethylamino]-9-[(1R,2S,3R,4S)-4-(2,5-dioxo-imidazolidin-1-yl)-2,3-dihydroxy-cyclopentyl]-9H-purin-2-yl}-pyrrolidin-3-yl)-3-(3-hydroxy-benzyl)-urea |
| C23 | 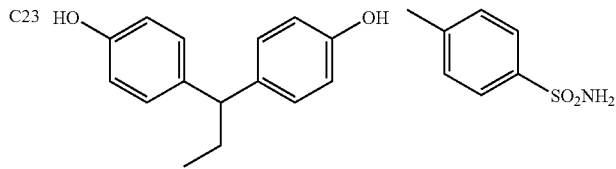 | | 4-[3-((R)-1-{6-[2,2-Bis-(4-hydroxy-phenyl)-ethylamino]-9-[(1R,2S,3R,4S)-4-(2,5-dioxo-imidazolidin-1-yl)-2,3-dihydroxy-cyclopentyl]-9H-purin-2-yl}-pyrrolidin-3-yl)-ureido]-benzenesulfonamide |

-continued

| | | | |
|---|---|---|---|
| C24 | [structure: bis(4-hydroxyphenyl)ethyl with propyl] | [structure: 3-methylbenzenesulfonamide] | 3-[3-((R)-1-{6-[2,2-Bis-(4-hydroxy-phenyl)-ethylamino]-9-[(1R,2S,3R,4S)-4-(2,5-dioxo-imidazolidin-1-yl)-2,3-dihydroxy-cyclopentyl]-9H-purin-2-yl}-pyrrolidin-3-yl)-ureido]-benzenesulfonamide |
| C25 | [structure: 2,2-diphenylethyl] | [structure: 3-methylpyridine] | 1-{(R)-1-[9-[(1R,2S,3R,4S)-2,3-Dihydroxy-4-(3-methyl-2,5-dioxo-imidazolidin-1-yl)-cyclopentyl]-6-(2,2-diphenyl-ethylamino)-9H-purin-2-yl]-pyrrolidin-3-yl}-3-pyridin-3-yl-urea |
| C26 | [structure: 2,2-diphenylethyl] | [structure: 3-methylphenol] | 1-{(R)-1-[9-[(1R,2S,3R,4S)-2,3-Dihydroxy-4-(3-methyl-2,5-dioxo-imidazolidin-1-yl)-cyclopentyl]-6-(2,2-diphenyl-ethylamino)-9H-purin-2-yl]-pyrrolidin-3-yl}-3-(3-hydroxy-benzyl)-urea |
| C27 | [structure: 2,2-diphenylethyl] | [structure: 4-methylbenzenesulfonamide] | 4-(3-{(R)-1-[9-[(1R,2S,3R,4S)-2,3-Dihydroxy-4-(3-methyl-2,5-dioxo-imidazolidin-1-yl)-cyclopentyl]-6-(2,2-diphenyl-ethylamino)-9H-purin-2-yl]-pyrrolidin-3-yl}-ureido)-benzenesulfonamide |
| C28 | [structure: 2,2-diphenylethyl] | [structure: 3-methylbenzenesulfonamide] | 3-(3-{(R)-1-[9-[(1R,2S,3R,4S)-2,3-Dihydroxy-4-(3-methyl-2,5-dioxo-imidazolidin-1-yl)-cyclopentyl]-6-(2,2-diphenyl-ethylamino)-9H-purin-2-yl]-pyrrolidin-3-yl}-ureido)-benzenesulfonamide |
| C29 | [structure: (S)-3-hydroxy-2-methyl-1-phenylpropyl] | [structure: 3-methylpyridine] | 1-{(R)-1-[9-[(1R,2S,3R,4S)-2,3-Dihydroxy-4-(3-methyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-3-pyridin-3-yl-urea |
| C30 | [structure: (S)-3-hydroxy-2-methyl-1-phenylpropyl] | [structure: 3-methylphenol] | 1-{(R)-1-[9-[(1R,2S,3R,4S)-2,3-Dihydroxy-4-(3-methyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-3-(3-hydroxy-benzyl)-urea |

| | | | |
|---|---|---|---|
| C31 | 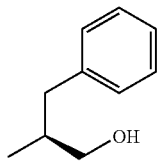 | 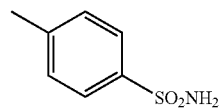 | 4-(3-{(R)-1-[9-[(1R,2S,3R,4S)-2,3-Dihydroxy-4-(3-methyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-ureido)-benzenesulfonamide |
| C32 | 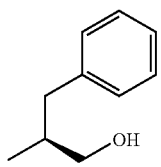 | 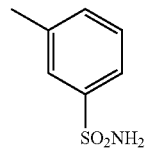 | 3-(3-{(R)-1-[9-[(1R,2S,3R,4S)-2,3-Dihydroxy-4-(3-methyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-ureido)-benzenesulfonamide |
| C33 | 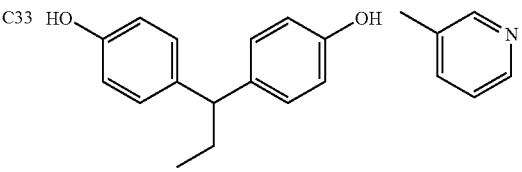 | | 1-((R)-1-{6-[2,2-Bis-(4-hydroxy-phenyl)-ethylamino]-9-[(1R,2S,3R,4S)-2,3-dihydroxy-4-(3-methyl-2,5-dioxo-imidazolidin-1-yl)-cyclopentyl]-9H-purin-2-yl}-pyrrolidin-3-yl)-3-pyridin-3-yl-urea |
| C34 | 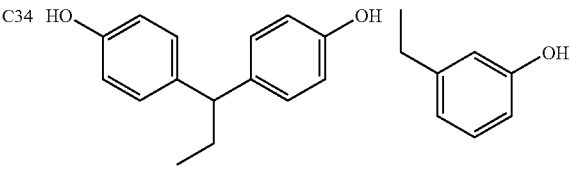 | | 1-((R)-1-{6-[2,2-Bis-(4-hydroxy-phenyl)-ethylamino]-9-[(1R,2S,3R,4S)-2,3-dihydroxy-4-(3-methyl-2,5-dioxo-imidazolidin-1-yl)-cyclopentyl]-9H-purin-2-yl}-pyrrolidin-3-yl)-3-(3-hydroxy-benzyl)-urea |
| C35 | 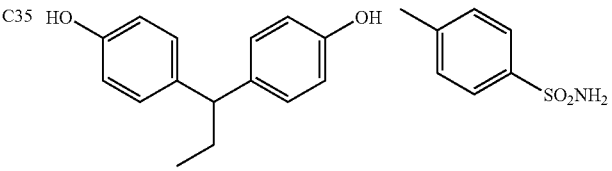 | | 4-[3-((R)-1-{6-[2,2-Bis-(4-hydroxy-phenyl)-ethylamino]-9-[(1R,2S,3R,4S)-2,3-dihydroxy-4-(3-methyl-2,5-dioxo-imidazolidin-1-yl)-cyclopentyl]-9H-purin-2-yl}-pyrrolidin-3-yl)-ureido]-benzenesulfonamide |
| C36 | 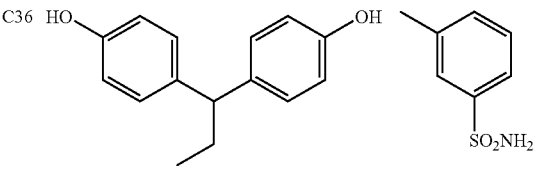 | | 3-[3-((R)-1-{6-[2,2-Bis-(4-hydroxy-phenyl)-ethylamino]-9-[(1R,2S,3R,4S)-2,3-dihydroxy-4-(3-methyl-2,5-dioxo-imidazolidin-1-yl)-cyclopentyl]-9H-purin-2-yl}-pyrrolidin-3-yl)-ureido]-benzenesulfonamide |

-continued

| | | | |
|---|---|---|---|
| C37 | 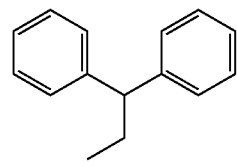 | 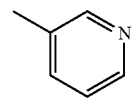 | 1-{(R)-1-[9-[(1R,2S,3R,4S)-2,3-Dihydroxy-4-(4-hydroxymethyl-2,5-dioxo-imidazolidin-1-yl)-cyclopentyl]-6-(2,2-diphenyl-ethylamino)-9H-purin-2-yl]-pyrrolidin-3-yl}-3-pyridin-3-yl-urea |
| C38 | 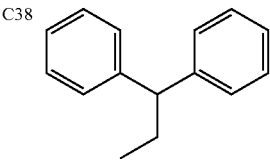 | 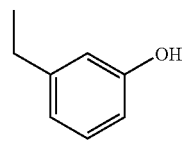 | 1-{(R)-1-[9-[(1R,2S,3R,4S)-2,3-Dihydroxy-4-(4-hydroxymethyl-2,5-dioxo-imidazolidin-1-yl)-cyclopentyl]-6-(2,2-diphenyl-ethylamino)-9H-purin-2-yl]-pyrrolidin-3-yl}-3-(3-hydroxy-benzyl)-urea |
| C39 | 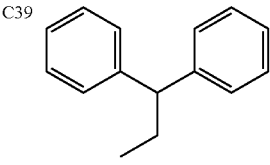 | 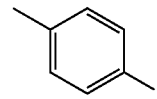 | 4-(3-{(R)-1-[9-[(1R,2S,3R,4S)-2,3-Dihydroxy-4-(4-hydroxymethyl-2,5-dioxo-imidazolidin-1-yl)-cyclopentyl]-6-(2,2-diphenyl-ethylamino)-9H-purin-2-yl]-pyrrolidin-3-yl}-ureido)-benzenesulfonamide |
| C40 | 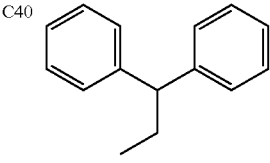 | 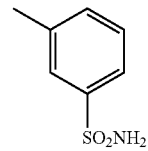 | 3-(3-{(R)-1-[9-[(1R,2S,3R,4S)-2,3-Dihydroxy-4-(4-hydroxymethyl-2,5-dioxo-imidazolidin-1-yl)-cyclopentyl]-6-(2,2-diphenyl-ethylamino)-9H-purin-2-yl]-pyrrolidin-3-yl}-ureido)-benzenesulfonamide |
| C41 | 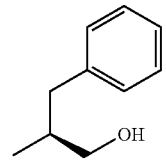 | 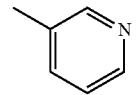 | 1-{(R)-1-[9-[(1R,2S,3R,4S)-2,3-Dihydroxy-4-(4-hydroxymethyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-3-pyridin-3-yl-urea |
| C42 | 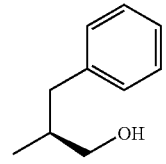 | 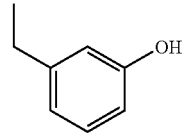 | 1-{(R)-1-[9-[(1R,2S,3R,4S)-2,3-Dihydroxy-4-(4-hydroxymethyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-3-(3-hydroxy-benzyl)-urea |

| | | | |
|---|---|---|---|
| C43 | 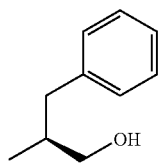 | 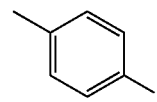 | 4-(3-{(R)-1-[9-[(1R,2S,3R,4S)-2,3-Dihydroxy-4-(4-hydroxymethyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-ureido)-benzenesulfonamide |
| C44 | 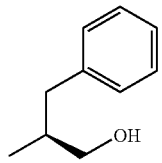 | 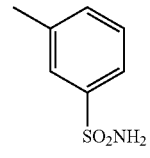 | 3-(3-{(R)-1-[9-[(1R,2S,3R,4S)-2,3-Dihydroxy-4-(4-hydroxymethyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-ureido)-benzenesulfonamide |
| C45 | 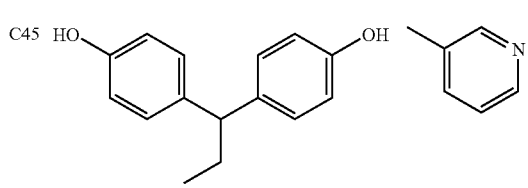 | | 1-((R)-1-{6-[2,2-Bis-(4-hydroxy-phenyl)-ethylamino]-9-[(1R,2S,3R,4S)-2,3-dihydroxy-4-(4-hydroxymethyl-2,5-dioxo-imidazolidin-1-yl)-cyclopentyl]-9H-purin-2-yl}-pyrrolidin-3-yl)-3-pyridin-3-yl-urea |
| C46 | 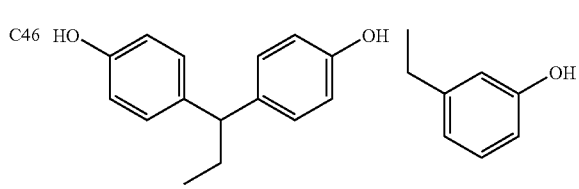 | | 1-((R)-1-{6-[2,2-Bis-(4-hydroxy-phenyl)-ethylamino]-9-[(1R,2S,3R,4S)-2,3-dihydroxy-4-(4-hydroxymethyl-2,5-dioxo-imidazolidin-1-yl)-cyclopentyl]-9H-purin-2-yl}-pyrrolidin-3-yl)-3-(3-hydroxy-benzyl)-urea |
| C47 | 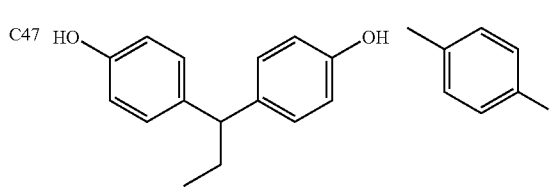 | | 4-[3-((R)-1-{6-[2,2-Bis-(4-hydroxy-phenyl)-ethylamino]-9-[(1R,2S,3R,4S)-2,3-dihydroxy-4-(4-hydroxymethyl-2,5-dioxo-imidazolidin-1-yl)-cyclopentyl]-9H-purin-2-yl}-pyrrolidin-3-yl)-ureido]-benzenesulfonamide |
| C48 | 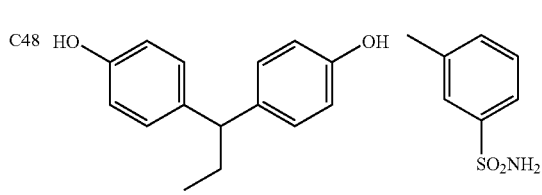 | | 3-[3-((R)-1-{6-[2,2-Bis-(4-hydroxy-phenyl)-ethylamino]-9-[(1R,2S,3R,4S)-2,3-dihydroxy-4-(4-hydroxymethyl-2,5-dioxo-imidazolidin-1-yl)-cyclopentyl]-9H-purin-2-yl}-pyrrolidin-3-yl)-ureido]-benzenesulfonamide |

-continued

C49 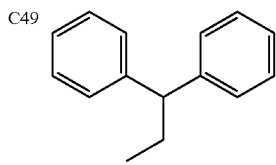 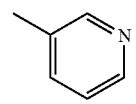 1-{(R)-1-[9-[(1R,2S,3R,4S)-2,3-Dihydroxy-4-(4-hydroxymethyl-pyrazol-1-yl)-cyclopentyl]-6-(2,2-diphenyl-ethylamino)-9H-purin-2-yl]-pyrrolidin-3-yl}-3-pyridin-3-yl-urea C50 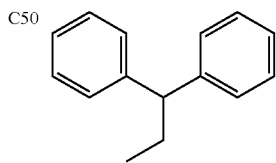 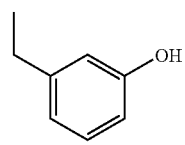 1-{(R)-1-[9-[(1R,2S,3R,4S)-2,3-Dihydroxy-4-(4-hydroxymethyl-pyrazol-1-yl)-cyclopentyl]-6-(2,2-diphenyl-ethylamino)-9H-purin-2-yl]-pyrrolidin-3-yl}-3-(3-hydroxy-benzyl)-urea C51 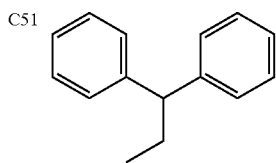 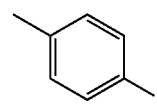 4-(3-{(R)-1-[9-[(1R,2S,3R,4S)-2,3-Dihydroxy-4-(4-hydroxymethyl-pyrazol-1-yl)-cyclopentyl]-6-(2,2-diphenyl-ethylamino)-9H-purin-2-yl]-pyrrolidin-3-yl}-ureido)-benzenesulfonamide C52 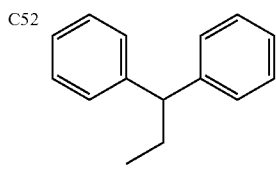 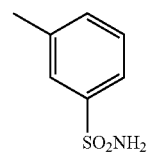 3-(3-{(R)-1-[9-[(1R,2S,3R,4S)-2,3-Dihydroxy-4-(4-hydroxymethyl-pyrazol-1-yl)-cyclopentyl]-6-(2,2-diphenyl-ethylamino)-9H-purin-2-yl]-pyrrolidin-3-yl}-ureido)-benzenesulfonamide C53 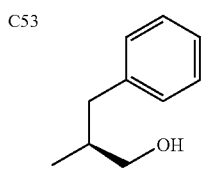 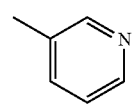 1-{(R)-1-[9-[(1R,2S,3R,4S)-2,3-Dihydroxy-4-(4-hydroxymethyl-pyrazol-1-yl)-cyclopentyl]-6-((S)-1-hydroxymethyl-2-phenyl-ethylamino)-9H-purin-2-yl]-pyrrolidin-3-yl}-3-pyridin-3-yl-urea C54 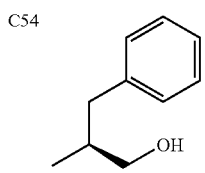 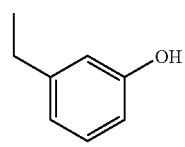 1-{(R)-1-[9-[(1R,2S,3R,4S)-2,3-Dihydroxy-4-(4-hydroxymethyl-pyrazol-1-yl)-cyclopentyl]-6-((S)-1-hydroxymethyl-2-phenyl-ethylamino)-9H-purin-2-yl]-pyrrolidin-3-yl}-3-(3-hydroxy-benzyl)-urea

| | | | |
|---|---|---|---|
| C55 | 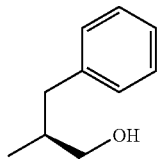 | 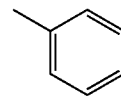 | 4-(3-{(R)-1-[9-[(1R,2S,3R,4S)-2,3-Dihydroxy-4-(4-hydroxymethyl-pyrazol-1-yl)-cyclopentyl]-6-((S)-1-hydroxymethyl-2-phenyl-ethylamino)-9H-purin-2-yl]-pyrrolidin-3-yl}-ureido)-benzenesulfonamide |
| C56 | 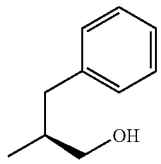 | 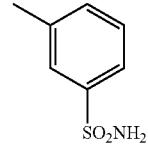 | 3-(3-{(R)-1-[9-[(1R,2S,3R,4S)-2,3-Dihydroxy-4-(4-hydroxymethyl-pyrazol-1-yl)-cyclopentyl]-6-((S)-1-hydroxymethyl-2-phenyl-ethylamino)-9H-purin-2-yl]-pyrrolidin-3-yl}-ureido)-benzenesulfonamide |
| C57 | 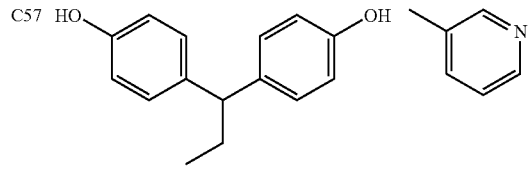 | | 1-((R)-1-{6-[2,2-Bis-(4-hydroxy-phenyl)-ethylamino]-9-[(1R,2S,3R,4S)-2,3-dihydroxy-4-(4-hydroxymethyl-pyrazol-1-yl)-cyclopentyl]-9H-purin-2-yl}-pyrrolidin-3-yl)-3-pyridin-3-yl-urea |
| C58 | 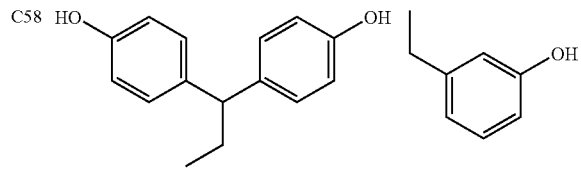 | | 1-((R)-1-{6-[2,2-Bis-(4-hydroxy-phenyl)-ethylamino]-9-[(1R,2S,3R,4S)-2,3-dihydroxy-4-(4-hydroxymethyl-pyrazol-1-yl)-cyclopentyl]-9H-purin-2-yl}-pyrrolidin-3-yl)-3-(3-hydroxy-benzyl)-urea |
| C59 | 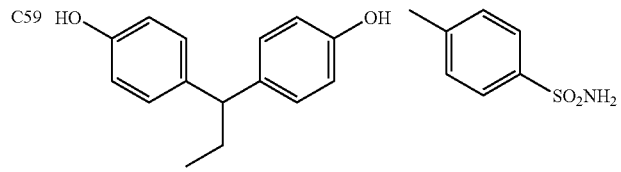 | | 4-[3-((R)-1-{6-[2,2-Bis-(4-hydroxy-phenyl)-ethylamino]-9-[(1R,2S,3R,4S)-2,3-dihydroxy-4-(4-hydroxymethyl-pyrazol-1-yl)-cyclopentyl]-9H-purin-2-yl}-pyrrolidin-3-yl)-ureido]-benzenesulfonamide |
| C60 | 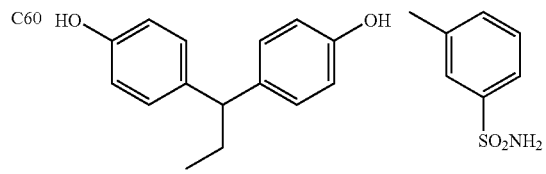 | | 3-[3-((R)-1-{6-[2,2-Bis-(4-hydroxy-phenyl)-ethylamino]-9-[(1R,2S,3R,4S)-2,3-dihydroxy-4-(4-hydroxymethyl-pyrazol-1-yl)-cyclopentyl]-9H-purin-2-yl}-pyrrolidin-3-yl)-ureido]-benzenesulfonamide |

-continued

| | | |
|---|---|---|
| C61 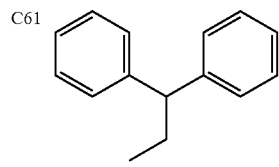 | 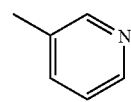 | 1-{(R)-1-[9-[(1R,2S,3R,4S)-2,3-Dihydroxy-4-(4-hydroxymethyl-[1,2,3]triazol-2-yl)-cyclopentyl]-6-(2,2-diphenyl-ethylamino)-9H-purin-2-yl]-pyrrolidin-3-yl}-3-pyridin-3-yl-urea |
| C62 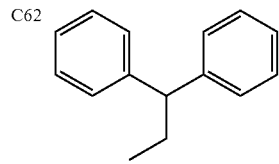 | 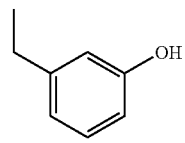 | 1-{(R)-1-[9-[(1R,2S,3R,4S)-2,3-Dihydroxy-4-(4-hydroxymethyl-[1,2,3]triazol-2-yl)-cyclopentyl]-6-(2,2-diphenyl-ethylamino)-9H-purin-2-yl]-pyrrolidin-3-yl}-3-(3-hydroxy-benzyl)-urea |
| C63 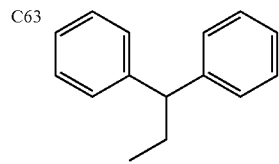 | 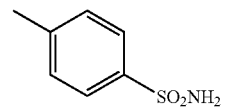 | 4-(3-{(R)-1-[9-[(1R,2S,3R,4S)-2,3-Dihydroxy-4-(4-hydroxymethyl-[1,2,3]triazol-2-yl)-cyclopentyl]-6-(2,2-diphenyl-ethylamino)-9H-purin-2-yl]-pyrrolidin-3-yl}-ureido)-benzenesulfonamide |
| C64 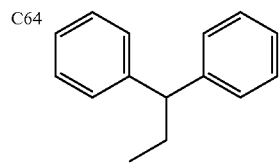 | 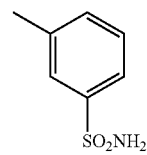 | 3-(3-{(R)-1-[9-[(1R,2S,3R,4S)-2,3-Dihydroxy-4-(4-hydroxymethyl-[1,2,3]triazol-2-yl)-cyclopentyl]-6-(2,2-diphenyl-ethylamino)-9H-purin-2-yl]-pyrrolidin-3-yl}-ureido)-benzenesulfonamide |
| C65 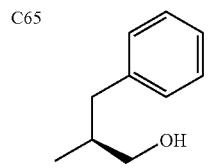 | 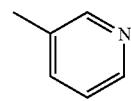 | 1-{(R)-1-[9-[(1R,2S,3R,4S)-2,3-Dihydroxy-4-(4-hydroxymethyl-[1,2,3]triazol-2-yl)-cyclopentyl]-6-((S)-1-hydroxymethyl-2-phenyl-ethylamino)-9H-purin-2-yl]-pyrrolidin-3-yl}-3-pyridin-3-yl-urea |
| C66 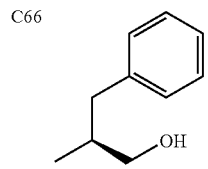 | 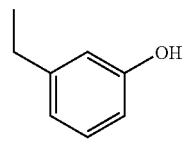 | 1-{(R)-1-[9-[(1R,2S,3R,4S)-2,3-Dihydroxy-4-(4-hydroxymethyl-[1,2,3]triazol-2-yl)-cyclopentyl]-6-((S)-1-hydroxymethyl-2-phenyl-ethylamino)-9H-purin-2-yl]-pyrrolidin-3-yl}-3-(3-hydroxy-benzyl)-urea |

-continued

| | | | |
|---|---|---|---|
| C67 | 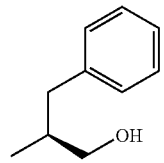 | 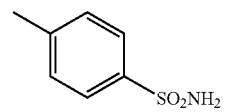 | 4-(3-{(R)-1-[9-[(1R,2S,3R,4S)-2,3-Dihydroxy-4-(4-hydroxymethyl-[1,2,3]triazol-2-yl)-cyclopentyl]-6-((S)-1-hydroxymethyl-2-phenyl-ethylamino)-9H-purin-2-yl]-pyrrolidin-3-yl}-ureido)-benzenesulfonamide |
| C68 | 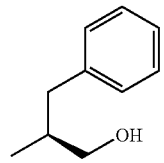 | 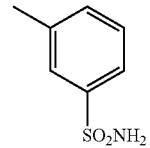 | 3-(3-{(R)-1-[9-[(1R,2S,3R,4S)-2,3-Dihydroxy-4-(4-hydroxymethyl-[1,2,3]triazol-2-yl)-cyclopentyl]-6-((S)-1-hydroxymethyl-2-phenyl-ethylamino)-9H-purin-2-yl]-pyrrolidin-3-yl}-ureido)-benzenesulfonamide |
| C69 | 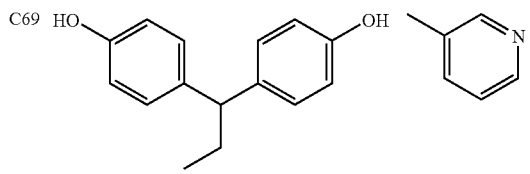 | | 1-((R)-1-{6-[2,2-Bis-(4-hydroxy-phenyl)-ethylamino]-9-[(1R,2S,3R,4S)-2,3-dihydroxy-4-(4-hydroxymethyl-[1,2,3]triazol-2-yl)-cyclopentyl]-9H-purin-2-yl}-pyrrolidin-3-yl)-3-pyridin-3-yl-urea |
| C70 | 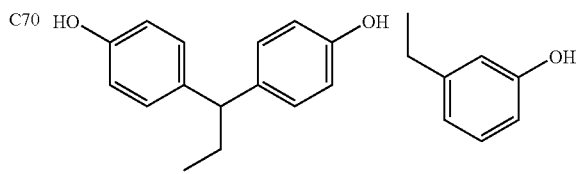 | | 1-((R)-1-{6-[2,2-Bis-(4-hydroxy-phenyl)-ethylamino]-9-[(1R,2S,3R,4S)-2,3-dihydroxy-4-(4-hydroxymethyl-[1,2,3]triazol-2-yl)-cyclopentyl]-9H-purin-2-yl}-pyrrolidin-3-yl)-3-(3-hydroxy-benzyl)-urea |
| C71 | 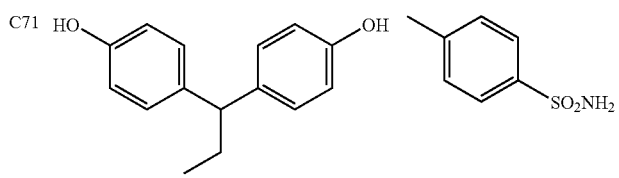 | | 4-[3-((R)-1-{6-[2,2-Bis-(4-hydroxy-phenyl)-ethylamino]-9-[(1R,2S,3R,4S)-2,3-dihydroxy-4-(4-hydroxymethyl-[1,2,3]triazol-2-yl)-cyclopentyl]-9H-purin-2-yl}-pyrrolidin-3-yl)-ureido]-benzenesulfonamide |
| C72 | 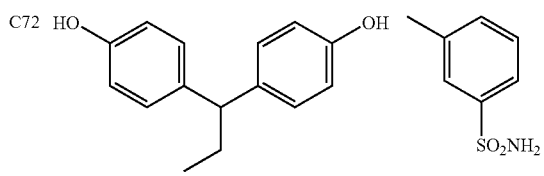 | | 3-[3-((R)-1-{6-[2,2-Bis-(4-hydroxy-phenyl)-ethylamino]-9-[(1R,2S,3R,4S)-2,3-dihydroxy-4-(4-hydroxymethyl-[1,2,3]triazol-2-yl)-cyclopentyl]-9H-purin-2-yl}-pyrrolidin-3-yl)-ureido]-benzenesulfonamide |

-continued

| | | |
|---|---|---|
| C73 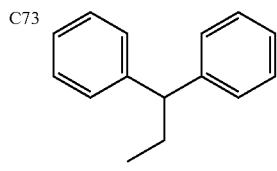 | 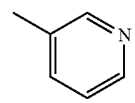 | 1-{(R)-1-[9-[(1R,2S,3R,4S)-2,3-Dihydroxy-4-(5-hydroxymethyl-tetrazol-2-yl)-cyclopentyl]-6-(2,2-diphenyl-ethylamino)-9H-purin-2-yl]-pyrrolidin-3-yl}-3-pyridin-3-yl-urea |
| C74 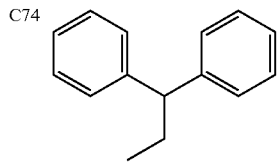 | 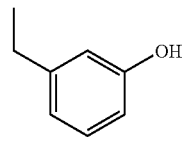 | 1-{(R)-1-[9-[(1R,2S,3R,4S)-2,3-Dihydroxy-4-(5-hydroxymethyl-tetrazol-2-yl)-cyclopentyl]-6-(2,2-diphenyl-ethylamino)-9H-purin-2-yl]-pyrrolidin-3-yl}-3-(3-hydroxy-benzyl)-urea |
| C75 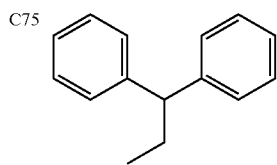 | 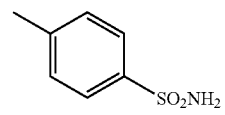 | 4-(3-{(R)-1-[9-[(1R,2S,3R,4S)-2,3-Dihydroxy-4-(5-hydroxymethyl-tetrazol-2-yl)-cyclopentyl]-6-(2,2-diphenyl-ethylamino)-9H-purin-2-yl]-pyrrolidin-3-yl}-ureido)-benzenesulfonamide |
| C76 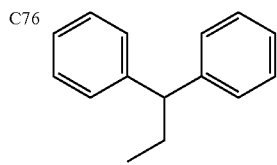 | 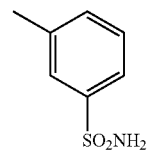 | 3-(3-{(R)-1-[9-[(1R,2S,3R,4S)-2,3-Dihydroxy-4-(5-hydroxymethyl-tetrazol-2-yl)-cyclopentyl]-6-(2,2-diphenyl-ethylamino)-9H-purin-2-yl]-pyrrolidin-3-yl}-ureido)-benzenesulfonamide |
| C77 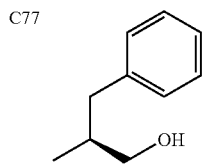 | 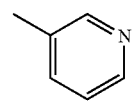 | 1-{(R)-1-[9-[(1R,2S,3R,4S)-2,3-Dihydroxy-4-(5-hydroxymethyl-tetrazol-2-yl)-cyclopentyl]-6-((S)-1-hydroxymethyl-2-phenyl-ethylamino)-9H-purin-2-yl]-pyrrolidin-3-yl}-3-pyridin-3-yl-urea |
| C78 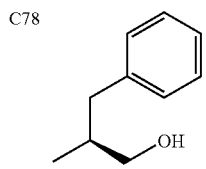 | 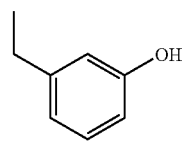 | 1-{(R)-1-[9-[(1R,2S,3R,4S)-2,3-Dihydroxy-4-(5-hydroxymethyl-tetrazol-2-yl)-cyclopentyl]-6-((S)-1-hydroxymethyl-2-phenyl-ethylamino)-9H-purin-2-yl]-pyrrolidin-3-yl}-3-(3-hydroxy-benzyl)-urea |

| | | |
|---|---|---|
| C79 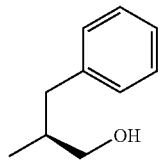 | 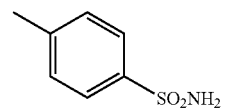 | 4-(3-{(R)-1-[9-[(1R,2S,3R,4S)-2,3-Dihydroxy-4-(5-hydroxymethyl-tetrazol-2-yl)-cyclopentyl]-6-((S)-1-hydroxymethyl-2-phenyl-ethylamino)-9H-purin-2-yl]-pyrrolidin-3-yl}-ureido)-benzenesulfonamide |
| C80 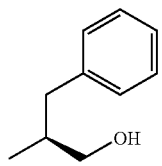 | 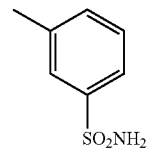 | 3-(3-{(R)-1-[9-[(1R,2S,3R,4S)-2,3-Dihydroxy-4-(5-hydroxymethyl-tetrazol-2-yl)-cyclopentyl]-6-((S)-1-hydroxymethyl-2-phenyl-ethylamino)-9H-purin-2-yl]-pyrrolidin-3-yl}-ureido)-benzenesulfonamide |
| C81 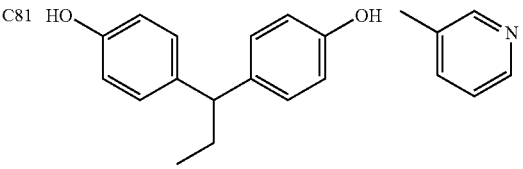 | | 1-((R)-1-{6-[2,2-Bis-(4-hydroxy-phenyl)-ethylamino]-9-[(1R,2S,3R,4S)-2,3-dihydroxy-4-(5-hydroxymethyl-tetrazol-2-yl)-cyclopentyl]-9H-purin-2-yl}-pyrrolidin-3-yl)-3-pyridin-3-yl-urea |
| C82 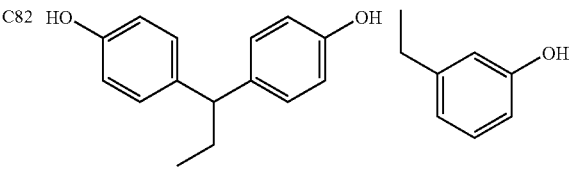 | | 1-((R)-1-{6-[2,2-Bis-(4-hydroxy-phenyl)-ethylamino]-9-[(1R,2S,3R,4S)-2,3-dihydroxy-4-(5-hydroxymethyl-tetrazol-2-yl)-cyclopentyl]-9H-purin-2-yl}-pyrrolidin-3-yl)-3-(3-hydroxy-benzyl)-urea |
| C83 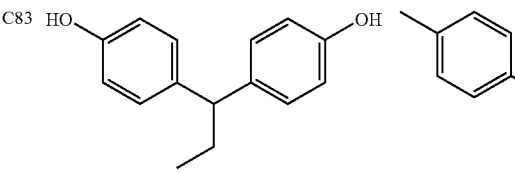 | | 4-[3-((R)-1-{6-[2,2-Bis-(4-hydroxy-phenyl)-ethylamino]-9-[(1R,2S,3R,4S)-2,3-dihydroxy-4-(5-hydroxymethyl-tetrazol-2-yl)-cyclopentyl]-9H-purin-2-yl}-pyrrolidin-3-yl)-ureido]-benzenesulfonamide |

-continued

| | | |
|---|---|---|
| C84 | 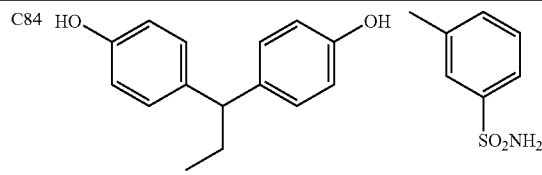 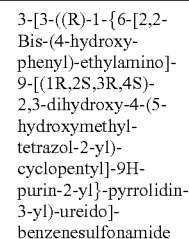 | 3-[3-((R)-1-{6-[2,2-Bis-(4-hydroxy-phenyl)-ethylamino]-9-[(1R,2S,3R,4S)-2,3-dihydroxy-4-(5-hydroxymethyl-tetrazol-2-yl)-cyclopentyl]-9H-purin-2-yl}-pyrrolidin-3-yl)-ureido]-benzenesulfonamide |
| C85 | 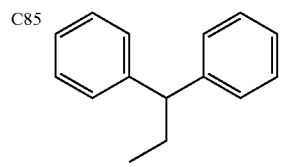 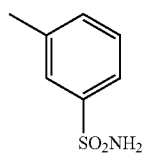 | 3-[3-((R)-1-{6-[2,2-Bis-phenyl-ethylamino]-9-[(1R,2S,3R,4S)-2,3-dihydroxy-4-(5-ethyl-tetrazol-2-yl)-cyclopentyl]-9H-purin-2-yl}-pyrrolidin-3-yl)-ureido]-benzenesulfonamide |

Preparation of Intermediate Compounds

Intermediate 1 Carbonic acid (1S,4R)-4-(2,6-dichloro-purin-9-yl)-cyclopent-2 enyl ester ethyl ester Step a: (1S,4R)-4-(2,6-Dichloro-purin-9-yl)-cyclopent-2 enol 2,6-Dichloropurine (10 g, 52.90 mmol), (1S,4R)-cis-4-acetoxy-2-cyclopenten-1-ol (10 g, 70.40 mmol), tris(dibenzylideneacetone)dipalladium(0) (3.20 g, 3.50 mmol) and polymer supported triphenylphosphine (3 mmol/g, 11.60 g, 35.00 mmol) are placed in an oven-dried flask under an atmosphere of argon. Dry deoxygenated THF (80 mL) is added and the reaction mixture is stirred gently for 5 minutes. Triethylamine (20 mL) is added and the reaction mixture is stirred at 50° C. The reaction is shown to be complete by LCMS after 1 hour. The reaction mixture is allowed to cool, filtered and the solvent is removed in vacuo. The title compound is obtained after purification by flash column chromatography (silica, dichloromethane/methanol 25:1).

$^1$H NMR (CDCl$_3$, 400 MHz); 8.30 (s, 1H), 6.40 (m, 1H), 5.90 (m, 1H), 5.50 (m, 1H), 4.95 (m, 1H), 3.05 (m, 1H), 2.10 (m, 1H). (MH$^+$) [MH+271]

Step b: Carbonic acid (1S,4R)-4-(2,6-dichloro-purin-9-yl)-cyclopent-2-enyl ester ethyl ester (1S,4R)-4-(2,6-Dichloro-purin-9-yl)-cyclopent-2-enol [step 1](9.5 g, 35.05 mmol) is placed in an oven-dried flask under an atmosphere of argon. Dry THF (200 mL) is added followed by dry pyridine (5.54 g, 70.1 mmol). Ethyl chloroformate (15.21 g, 140.2 mmol) is added slowly so that the temperature does not rise above 40° C. and the reaction mixture is stirred at RT. The reaction is shown to be complete by LCMS after 2 hours. The solvent is removed in vacuo and the residue is partitioned between dichloromethane (200 mL) and water (200 mL). The organic layer is washed with water (150 mL) and brine (150 mL), dried over MgSO$_4$, filtered and the solvent is removed in vacuo. The title compound is obtained after crystallization from methanol.

$^1$H NMR (CDCl$_3$, 400 MHz); 8.20 (s, 1H), 6.45 (m, 1H), 6.25 (m, 1H), 5.75 (m, 1H), 5.70 (m, 1H), 4.25 (q, 2H), 3.20 (m, 1H), 2.05 (m, 1H), 1.35 (t, 3H). [MH+343]

Intermediate 2 {(1S,2R,3S,4R)-4-[2-((R)-3-Amino-pyrrolidin-1-yl)-6-(2,2-diphenyl-ethylamino)-purin-9-yl]-2,3-dihydroxy-cyclopentyl}-carbamic acid benzyl ester Step a: Preparation of Intermediate 2a
Imidodicarbonic acid, bis(phenylmethyl)ester
(Chemical Abstracts Nomenclature)

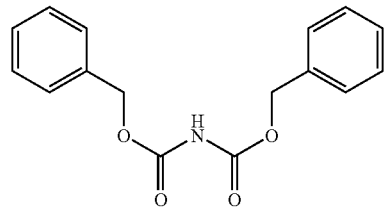

A cooled (0° C.) solution of benzyl carbamate (4.0 g, 27 mmol) in THF (100 mL) under an inert atmosphere of argon is treated with potassium iodide (3.2 g of a 35% w/w dispersion in oil, 28 mmol) portionwise over 10 minutes. The reaction mixture is allowed to warm to RT over 30 minutes after which time benzyl chloroformate (5.0 g, 29 mmol) is added. After stirring at RT for 2 hours, the reaction is quenched with water (20 mL). The THF is removed in vacuo and the resulting mixture is partitioned between EtOAc and 2 M HCl. The organic portion is separated and washed with brine, dried (MgSO$_4$) and concentrated in vacuo. The resulting oil is purified by chromatography on silica eluting with 1:3 EtOAc/ iso-hexane to yield a product which is recrystallized from DCM/iso-hexane to afford the title product.

Step b: Preparation of Intermediate 2b

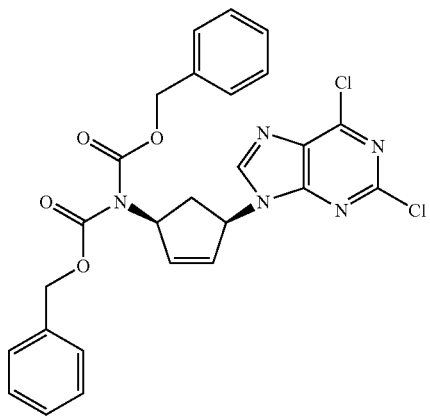

A solution comprising carbonic acid (1S,4R)-4-(2,6-dichloro-purin-9-yl)-cyclopent-2-enyl ester ethyl ester (Intermediate 1) (2.0 g, 5.83 mmol), Intermediate 2a (2.2 g, 7.58 mmol) and triphenyl phosphine (229 mg, 0.9 mmol) in THF (20 mL) is stirred at RT for 30 minutes. Tris(dibenzylideneacetone)dipalladium (0) (238 mg, 0.3 mmol) is added and the resulting mixture is stirred at RT for 1.5 hours. The solvent is removed in vacuo and the crude product is purified by chromatography on silica eluting with MeOH/DCM (gradient of 0-1% MeOH) to yield the title compound.

Step c: Preparation of Intermediate 2c

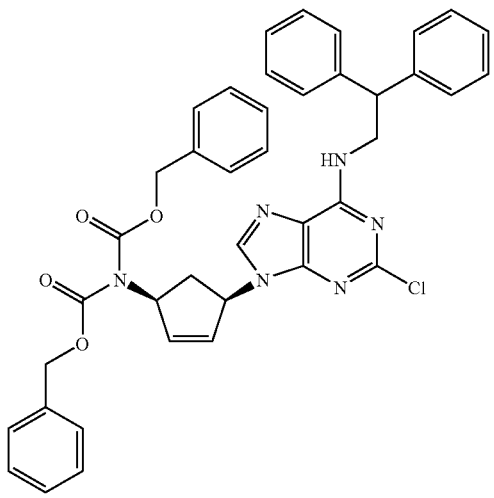

A solution comprising Intermediate 2b (0.68 g, 1.26 mmol), 1-amino-2,2-diphenylethane (0.37 g, 1.90 mmol) and TEA (190 mg, 1.90 mmol) in THF (10 mL) is stirred at 50° C. for 2 hours. The solvent is removed in vacuo the resulting oil/solid is partitioned between EtOAc and 0.2 M HCl. The organic portion is separated and washed with saturated sodium bicarbonate solution, water, brine, dried (MgSO$_4$) and concentrated in vacuo to afford the title compound. [MH+ 699.37]

Step d: Preparation of Intermediate 2d

A solution comprising Intermediate 2c (2.0 g, 2.86 mmol) and NMO (0.67 g, 5.7 mmol) in THF (20 mL) is treated with osmium tetroxide (2 mL of a 4% solution in water) and stirred at RT overnight. The solvent is removed in vacuo and the crude residue is partitioned between DCM and water. The organic portion is separated, washed with water, brine, dried (MgSO$_4$) and concentrated in vacuo. The resulting solid is titurated with MeCN to afford the title product [MH+733.40]

Step e: {(R)-1-[9-((1R,2S,3R,4S)-4-Benzyloxycarbonylamino-2,3-dihydroxy-cyclopentyl)-6-(2,2-diphenyl-ethylamino)-9H-purin-2-yl]-pyrrolidin-3-yl}carbamic acid tert-butyl ester A suspension of Intermediate 2d (1.03 g, 1.4 mmol) and (3R)-(+)-3-(Boc-amino)pyrrolidine (1.03 g, 5.5 mmol) in acetonitrile (2 mL) is treated with sodium iodide (ca. 2 mg) and then heated using microwave radiation at 160° C. After 1 hour, the solvent is removed in vacuo and the crude residue is partitioned between DCM and 0.2 M HCl. The organic layer is separated and the aqueous portion is extracted with DCM. The combined organic extracts are washed with saturated sodium bicarbonate solution, water, brine, dried (MgSO$_4$) and concentrated in vacuo to afford the title compound as a brown oil. [MH+745]

Step f: {(1S,2R,3S,4R)-4-[2-((R)-3 amino-pyrrolidin-1-yl)-6-(2,2-diphenyl-ethylamino)-purin-9-yl]-2,3-dihydroxy-cyclopentyl}-carbamic acid benzyl ester A solution of {(R)-1-[9-((1R,2S,3R,4S)-4-benzyloxycarbonylamino-2,3-dihydroxy-cyclopentyl-6-(2,2-diphenyl-ethylamino)-9H-purin-2-yl]-pyrrolidin-3-yl}-carbamic acid tert-butyl ester (1.24 g, 1.7 mmol) in MeOH (3 mL) is treated with 4 M HCl in dioxane (5 mL) and stirred at RT for 2 hours. The solvent is removed in vacuo and purification is carried out by reverse phase column chromatography (Isolute™ C18, 0-100% acetonitrile in water-0.1% HCl). The fractions are collected and the MeCN is removed in vacuo. The remaining aqueous portion is basified with saturated sodium bicarbonate solution and extracted with DCM. The combined organic extracted are dried (MgSO$_4$) and concentrated in vacuo to afford the title product. [MH+=649]

Intermediate 3 (1R,2S,3R,5S)-3-[2-Chloro-6-(2,2-diphenyl-ethylamino)-purin-9-yl]-5-(4-hydroxymethyl-pyrazol-1-yl)-cyclopentane-1,2-diol Step a: {1-[(1S,4R)-4-(2,6-Dichloro-purin-9-yl)-cyclopent-2-enyl]-1H-pyrazol-4-yl}-methanol A mixture comprising carbonic acid (1S,4R)-4-(2,6-dichloro-purin-9-yl)-cyclopent-2-enyl ester ethyl ester (Intermediate 1) (1.00 g, 2.92 mmol), (1H-pyrazol-4-yl)-methanol (preparation shown below) (0.34 g, 3.50 mmol) and triphenyl phosphine (0.115 g, 0.44 mmol) in deoxygenated THF (10 mL) under an inert atmosphere of argon is treated with tris(dibenzylideneacetone)dipalladium (0) (0.13 g, 0.15 mmol) and stirred at 50° C. for 1 hour. The solvent is removed in vacuo and the crude product is purified by chromatography on silica eluting with MeOH/DCM (1:25) to yield the title compound.

Preparation of (1H-pyrazol-4-yl)-methanol

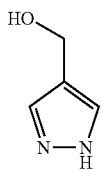

4-Ethylpyrazole carboxylate (10 g, 71.40 mmol) is placed in an oven-dried flask under an atmosphere of argon. Dry THF (100 mL) is added followed by the dropwise addition of lithium aluminium hydride (1 M in THF, 100 mL, 100 mmol). Once the addition is complete the reaction mixture is stirred at 50° C. The reaction is shown to be complete by NMR after 4 hours. The reaction mixture is cooled on an ice-bath and the reaction mixture is quenched with water (3.8 mL) then 15% sodium hydroxide (3.8 mL) and finally water again (11.4 mL). The solvent is removed in vacuo and the solid is placed in a Soxhlet apparatus. THF is refluxed through the system for 24 hours. The solvent is removed in vacuo to give the title compound.

$^1$H NMR (MeOD, 400 MHz); 7.60 (s, 2H), 4.55 (s, 2H).

Step b: (1-{(1S,4R)-4-[2-Chloro-6-(2,2-diphenyl-ethylamino)-purin-9-yl]-cyclopent-2-enyl}-1H-pyrazol-4-yl)-methanol A mixture comprising {1-[(1S,4R)-4-(2,6-dichloro purin-9-yl)-cyclopent-2-enyl]-1H-pyrazol-4-yl}-methanol (0.675 g, 1.92 mmol), diphenylethylamine (0.398 g, 2.02 mmol) and DIPEA (0.298 g, 2.31 mmol) in dry THF (20 mL) is stirred at 35 C for 3 days. The solvent is removed in vacuo and the resulting crude residue is partitioned between DCM and 0.1 M HCl. The organic portion is separated, washed with water, brine, dried (MgSO$_4$) and concentrated in vacuo to afford the title product.

Step d: (1R,2S,3R,5S)-3-[2-Chloro-6-(2,2-diphenyl-ethylamino)-purin-9-yl]-5-(4-hydroxymethyl-pyrazol-1-yl)-cyclopentane-1,2-diol (1-{(1S,4R)-4-[2-Chloro-6-(2,2-diphenyl-ethylamino)-purin-9-yl]cyclopent-2-enyl}-1H-pyrazol-4-yl)-methanol (0.84 g, 1.64 mmol) and NMO (0.39 g, 3.28 mmol) in THF (20 mL) is treated with osmium tetroxide (2 mL of a 4% solution in water) and stirred at RT overnight. The solvent is removed in vacuo and the resulting crude residue is partitioned between DCM and 0.1 M HCl (a small amount of MeOH added to improve solubility). The organic portion is dried (MgSO$_4$) and concentrated in vacuo. The crude product is dissolved in hot DCM to form the title product as a precipitate on cooling.

Intermediates 4a-4h

TABLE 1

| Intermediate | Structure | Name |
|---|---|---|
| 4a | 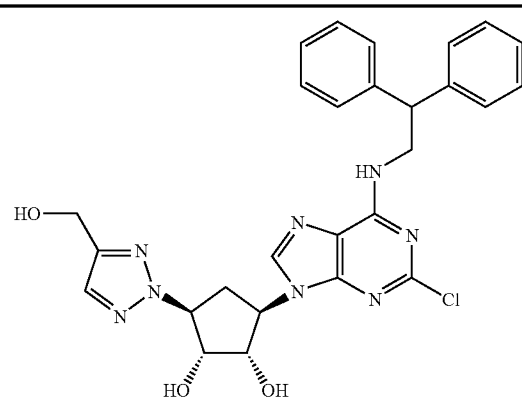 | (1R,2S,3R,5S)-3-[2-Chloro-6-(2,2-diphenyl-ethylamino)-purin-9-yl]-5-(4-hydroxymethyl-[1,2,3]triazol-2-yl)-cyclopentane-1,2-diol |
| 4b | 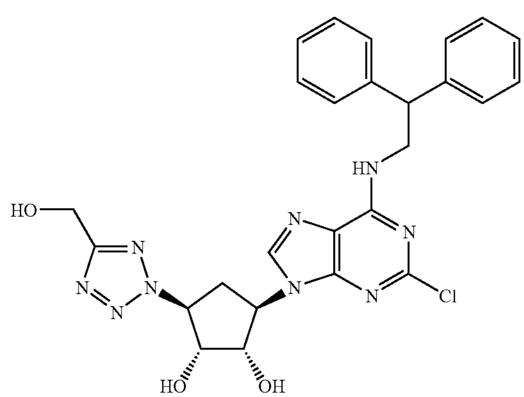 | (1R,2S,3R,5S)-3-[2-Chloro-6-(2,2-diphenyl-ethylamino)-purin-9-yl]-5-(5-hydroxymethyl-tetrazol-2-yl)-cyclopentane-1,2-diol |

TABLE 1-continued

| Intermediate | Structure | Name |
|---|---|---|
| 4c | 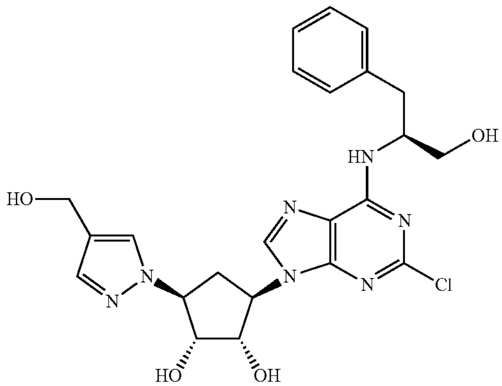 | (1R,2S,3R,5S)-3-[2-Chloro-6-((S)-1-hydroxymethyl-2-phenyl-ethylamino)-purin-9-yl]-5-(4-hydroxymethyl-pyrazol-1-yl)-cyclopentane-1,2-diol |
| 4d | 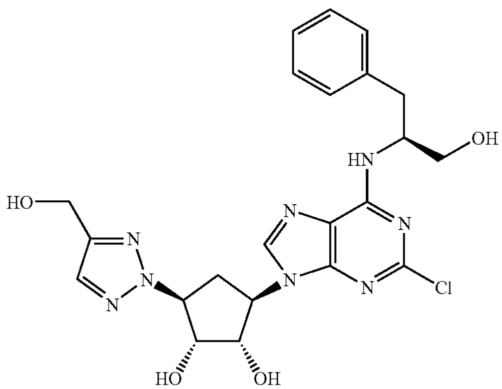 | (1R,2S,3R,5S)-3-[2-Chloro-6-((S)-1-hydroxymethyl-2-phenyl-ethylamino)-purin-9-yl]-5-(4-hydroxymethyl-[1,2,3]triazol-2-yl)-cyclopentane-1,2-diol |
| 4e | 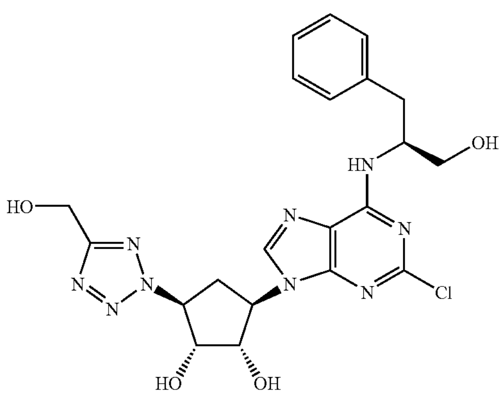 | (1R,2S,3R,5S)-3-[2-Chloro-6-((S)-1-hydroxymethyl-2-phenyl-ethylamino)-purin-9-yl]-5-(5-hydroxymethyl-tetrazol-2-yl)-cyclopentane-1,2-diol |
| 4f | 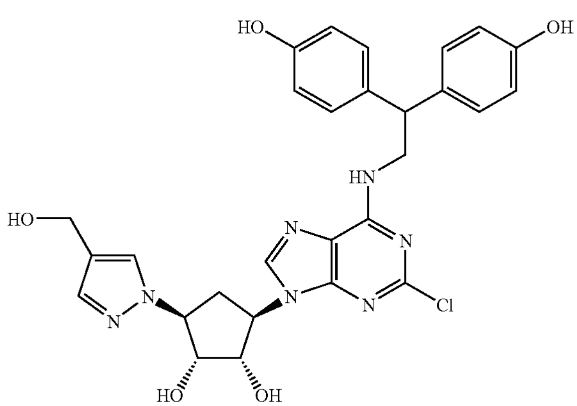 | (1R,2S,3R,5S)-3-{6-[2,2-Bis-(4-hydroxy-phenyl)ethylamino]-2-chloro-purin-9-yl}-5-(4-hydroxy methyl-pyrazol-1-yl)-cyclopentane-1,2-diol |

TABLE 1-continued

| Intermediate | Structure | Name |
|---|---|---|
| 4g | 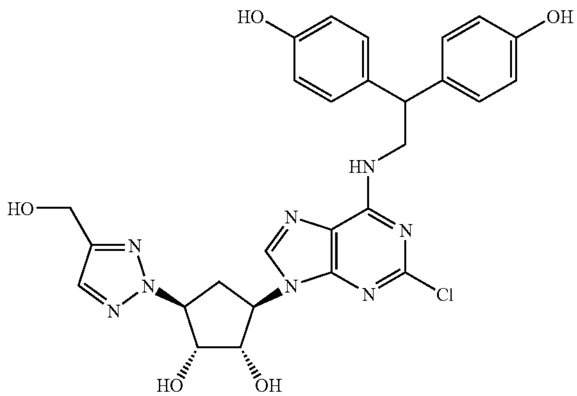 | (1R,2S,3R,5S)-3-{6-[2,2-Bis-(4-hydroxy-phenyl)-ethylamino]-2-chloro-purin-9-yl}-5-(4-hydroxymethyl-[1,2,3]triazol-2-yl)-cyclopentane-1,2-diol |
| 4h | 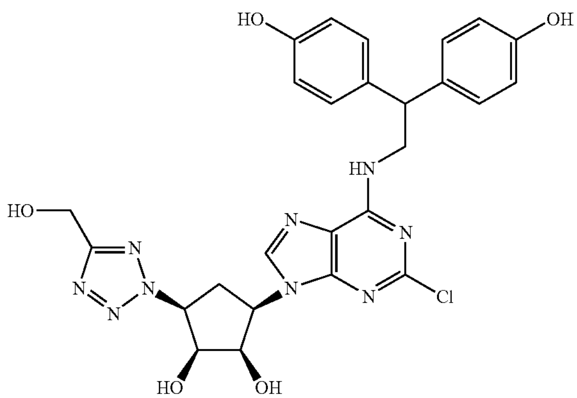 | (1R,2S,3R,5S)-3-{6-[2,2-Bis-(4-hydroxy-phenyl)-ethylamino]-2-chloro-purin-9-yl}-5-(5-hydroxy methyl-tetrazol-2-yl)-cyclopentane-1,2-diol |

The intermediates shown in the Table 1 are prepared analogously to Intermediate 3 by using the appropriate 5-membered heterocylic alcohol in Step 3a and by using the appropriate amine in Step 3c.

Intermediate 5 3-Isocyanato-benzenesulfonamide

To a vigorously stirred solution of 3-aminobenzenesulphonamide (1 g, 5.8 mmol) in dry 1,4-dioxane (25 mL) is added trichloromethyl chloroformate (1.72 g, 8.7 mmol) and the reaction mixture is heated to reflux for 3 hours. The solvent is removed in vacuo to yield the title compound which is used without further purification.

Intermediate 6 4-Isocyanato-benzenesulfonamide

This compound is prepared from 4-aminobenzenesulphonamide using a procedure analogous to that of 3-isocyanato-benzenesulfonamide (Intermediate 5) by replacing 3-aminobenzenesulphonamide with 4-aminobenzenesulphonamide.

Intermediates 7 and 8

These compounds namely,
((1S,2R,3S,4R)-4-{2-((R)-3-Amino-pyrrolidin-1-yl)-6-[2,2-bis-(4-hydroxy-phenyl)-ethylamino]-purin-9-yl}-2,3-dihydroxy-cyclopentyl)-carbamic acid benzyl ester (Intermediate 7); and {(1S,2R,3S,4R)-4-[2-((R)-3-Amino-pyrrolidin-1-yl)-6-((S)-1-hydroxymethyl-2-phenyl-ethylamino)-purin-9-yl]-2,3-dihydroxy-cyclopentyl}-carbamic acid benzyl ester (Intermediate 8), are prepared analogously to Intermediate 2 by replacing 1 amino-2,2-diphenylethane (Step 2c) with the appropriate amine.

Preparation of Examples

Example C1

1-{(R)-1-[9-[(1R,2S,3R,4S)-4-(2,5-Dioxo-imidazolidin-1-yl)-2,3-dihydroxy-cyclopentyl]-6-(2,2-diphenyl-ethylamino)-9H-purin-2-yl]-pyrrolidin-3-yl}-3-pyridin-3-yl-urea Step 1: ((1S,2R,3S,4R)-4-{6-(2,2-Diphenyl-ethylamino)-2-[(R)-3-(3-pyridin-3-yl-ureido)-pyrrolidin-1-yl]-purin-9-yl-}-2,3-dihydroxy-cyclopentyl)-carbamic acid benzyl ester trifluoroacetate A solution comprising {(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-carbamic acid benzyl ester (Intermediate 2) (0.1 g, 0.15 mmol), pyridine-3-isocyanate (0.02 g, 0.17 mmol) and TEA (0.017 g, 0.17 mmol) in THF (2 mL) is stirred at RT overnight. The solvent is removed in vacuo and purification is carried out by reverse phase column chromatography (Isolute™ C18, 0-100% acetonitrile in water-0.1% TFA). The fractions are collected and the MeCN is removed in vacuo. The remaining aqueous portion is basified with saturated sodium bicarbonate solution and extracted with DCM. The combined organic extracted are dried (MgSO$_4$) and concentrated in vacuo to afford the title product. [MH+769]

Step 2: 1-{(R)-1-[9-((1R,2S,3R,4S)-4-Amino-2,3-dihydroxy-cyclopentyl)-6-(2,2-diphenyl-ethylamino)-9H-purin-2-yl]-pyrrolidin-3-yl}-3-pyridin-3-yl-urea To a solution of ((1S,2R,3S,4R)-4-{6-(2,2-diphenyl-ethylamino)-2-[(R)-3-(3-pyridin-3-yl-ureido}pyrrolidin-1-yl]-purin-9-yl-2,3-dihydroxy-cyclopentyl)-carbamic acid benzyl ester trifluoroacetate (35 mg, 46 μmol) in ethanol (1 mL) under an inert atmosphere of argon is added 10% palladium on carbon (10 mg). The reaction mixture is purged with argon and placed under a positive atmosphere of hydrogen overnight after which time, the mixture is filtered through celite and the catalyst washed with ethanol. The organic portions are combined and concentrated in vacuo to yield the title compound. [MH+635]

Step 3: 1-{(R)-1-[9-[(1R,2S,3R,4S)-4-(2,5-Dioxo-imidazolidin-1-yl}-2,3-dihydroxy-cyclopentyl]-6-(2,2-diphenyl-ethylamino)-9H-purin-2-yl]-pyrrolidin-3-yl-3 pyridin 3-yl-urea hydrochloride To a solution of 1-{(R)-1-[9-((1R,2S,3R,4S)-4-amino-2,3-dihydroxy-cyclopentyl)-6-(2,2-diphenyl-ethylamino)-9H-purin-2-yl]-pyrrolidin-3-yl}-3-pyridin-3-yl-urea (17 mg, 26 μmol) in THF (1 mL) is added Z-L-alanine hydroxysuccinimidyl ester (9 mg, 29 μmol) and the reaction mixture is stirred at RT overnight. The solvent is removed in vacuo and the crude residue is dissolved in EtOH (1 mL) and purged with argon. Palladium on carbon (approximately 5 mg) is added and the reaction mixture is placed under a constant pressure of hydrogen (0.35 bar) and stirred at room temperature overnight. The resulting mixture is filtered through celite and concentrated in vacuo. Purification of the crude residue by reverse phase column chromatography (Isolute™ C18, 0-100% acetonitrile in water-0.1% HCl) affords the title compound. [MH+732.72].

Example C2

1-{(R)-1-[9-[(1R,2S,3R,4S)-4-(2,5-Dioxo-imidazolidin-1-yl}-2,3-dihydroxy-cyclopentyl]-6-(2,2-diphenyl-ethylamino)-9H-purin-2-yl]-pyrrolidin-3-yl}-3-pyridin-3-yl-urea trifluoroacetate This compound is prepared analogously to Example 1 by replacing Z-L-alanine hydroxysuccinimidyl ester (Step 3) with Z-glycine-N-succinimidyl ester. Purification is carried out by reverse phase column chromatography (Isolute™ C18, 0-100% acetonitrile in water-0.1% TFA). [MH+718.68].

Examples C3-C48

These examples can be prepared analogously to Example 1 by using the appropriate starting compound (either Intermediate 2, 7 or 8) and isocyanate in Step 1 and by using the appropriate succinimidyl ester in Step 3.

Those examples containing 3-hydroxybenzyl groups are prepared as follows: (3-hydroxy-benzyl)-carbamic acid phenyl ester (Intermediate BA) and (Intermediate 2, 7 or 8) are dissolved in MeOH and TEA. The reaction mixture is heated using microwave radiation at 100° C. for 30 minutes and then the solvent is removed in vacuo. Purification of the crude product by reverse phase column chromatography (Isolute™ C18, 0-100% acetonitrile in water-0.1% TFA) affords the product which is taken through Steps 2 and 3 (using the appropriate succinimidyl ester) to afford the final compound.

Examples C49-C84

These compounds are prepared analogously to Example 1 by combining the appropriate starting compound (Intermediates 3 or 4a-4-h) with the appropriate phenyl esters (Intermediates BA-BD).

Example C85

Step 1: {(R)-1-[6-(2,2-Diphenylethylamino-9H-purin-2-yl]-pyrrolidin-3-yl}-carbamic acid tert-butyl ester

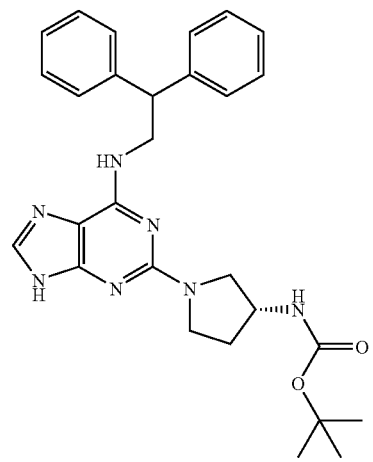

(2-Chloro-9H-purin-6-yl)-(2,2-diphenyl-ethyl)-amine (2.5 g) is added to Boc(R)-3-aminopyrrolidine (2.677 g). This is suspended in acetonitrile (10 mL) and put to microwave at 160° C. Analysis by LCMS shows reaction to be complete after 30 minutes. The reaction mixture is then suspended in acetonitrile and filtered. The resulting precipitate is then dried to give the title compound. MS (ES+) m/e 498 (MH+)

Step 2: {(R)-1-[6-(2,2-Diphenyl-ethylamino)-9-((1R,4S)-4-hydroxy-cyclopent-2-enyl)-9H-purin-2-yl]-pyrrolidin-3-yl}-carbamic acid tert-butyl ester

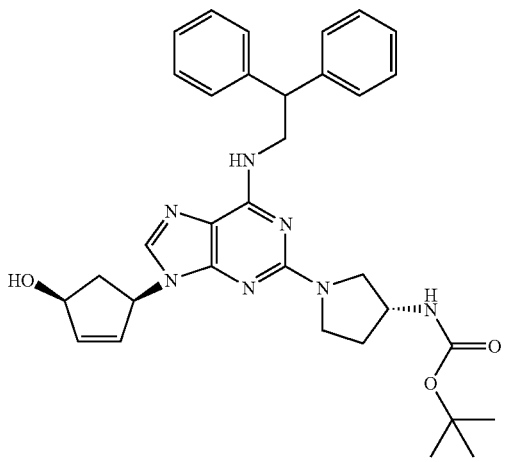

{(R)-1-[6-(2,2-Diphenyl-ethylamino)-9H-purin-2-yl]-pyrrolidin-3-yl}-carbamic acid tert-butyl ester (2.5 g) is suspended in THF (15 mL) under an inert atmosphere and oven dried glassware. Sodium hydride (130 mg) is added to the stirring suspension. This is stirred until dissolution has occurred. (1S,4R)-cis-4-Acetoxy-2-cyclopentan-1-ol (865 mg) and triphenylphosphine (236 mg) are placed in an oven-dried flask under an inert atmosphere, this is dissolved in THF (15 mL). This solution is added to the solution of {(R)-1-[6-(2,2-diphenyl-ethylamino)-9H-purin-2-yl]-pyrrolidin-3-yl}-carbamic acid tert-butyl ester and sodium hydride via syringe, tris-Dibenzylideneacetone)dipalladium (275 mg) is then added and the reaction is stirred at 50° C. The reaction is shown to be complete after 1 hour by LCMS. The reaction is allowed to cool and the solvent is removed in vacuo. The residue is purified by flash column chromatography (silica, dichloromethane/methanol 25:1), giving the title compound. MS (ES+) m/e 582.62 (MH+)

Step 3: Carbonic acid (1S,4R)-4-[2-((R)-3-tert-butoxycarbonylamino-pyrrolidin-1-yl)-6-(2,2-diphenyl-ethylamino)-purin-9-yl]-cyclopent-2-enyl ester ethyl ester

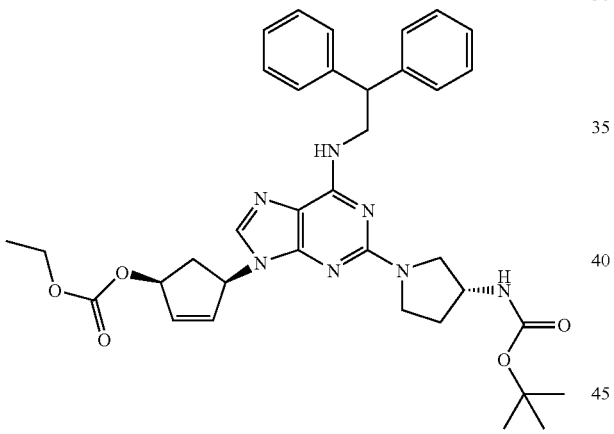

{(R)-1-[6-(2,2-Diphenyl-ethylamino)-9-((1R,4S)-4-hydroxy-cyclopent-2-enyl)-9H-purin-2-yl]-pyrrolidin-3-yl}carbamic acid tert-butyl ester (500 mg) is dissolved in dry deoxygenated THF (10 mL). Pyridine (416 µL) is added to the solution. Ethyl chloroformate (492 µL) is pre-dissolved in THF (2.5 mL) and added dropwise to the solution at 0° C. The reaction is stirred at RT. Analysis by LCMS shows reaction completion after 2 hours. The solvent is removed in vacuo. The residue is dissolved in dichloromethane (10 mL) and portioned against 0.1 M HCl (10 mL). The organic layer is then washed with water (20 mL) and brine (10 mL), dried over MgSO₄, filtered and the solvent removed in vacuo. The title compound is obtained after purification by flash column chromatography (silica, dichloromethane/methanol 40:1).

MS (ES+) m/e 655.46 (MH+).

Step 4: ((R)-1-{6-(2,2-Diphenyl-ethylamino-9-[(1R,4S)-4-(5-ethyl-tetrazol-2-yl)-cyclopent-2-enyl]-9H-purin-2-yl}-pyrrolidin-3-yl)-carbamic acid tert-butyl ester

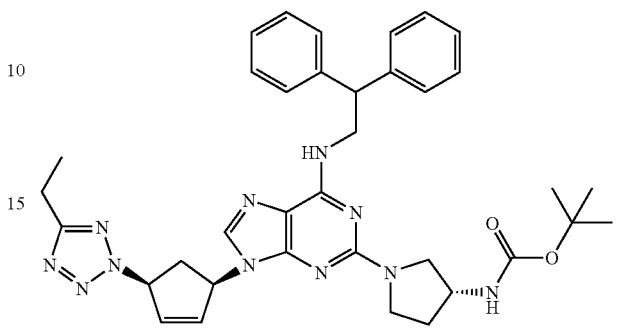

Carbonic acid (1S,4R)-4-[2-((R)-3-tert-butoxycarbonylamino-pyrrolidin-1-yl)-6-(2,2-diphenyl-ethylamino)-purin-9-yl]-cyclopent-2-enyl ester ethyl ester (760 mg) is added to ethyl tetrazole (125 mg) and triphenylphosphine (46 mg) in an oven-dried flask under argon. This is dissolved in anhydrous THF (10 mL). tris-(Dibenzylideneacetone)-dipalladium (53 mg) is added to the stirring solution. The reaction is stirred at 50° C. Analysis by LCMS shows reaction completion after 1 hour. The solvent is removed in vacuo. The title compound is obtained by flash column chromatography (silica, dichloromethane/methanol 50:1). MS (ES+) m/e 662.4 (MH+).

Step 5: ((R)-1-{6-(2,2-Diphenyl-ethylamino)-9-[(1R,4S)-4-(5-ethyl-tetrazol-2-yl)-2,3-dihydroxy-cyclopentyl]-9H-purin-2-yl}-pyrrolidin-3-yl)-carbamic acid tert-butyl ester

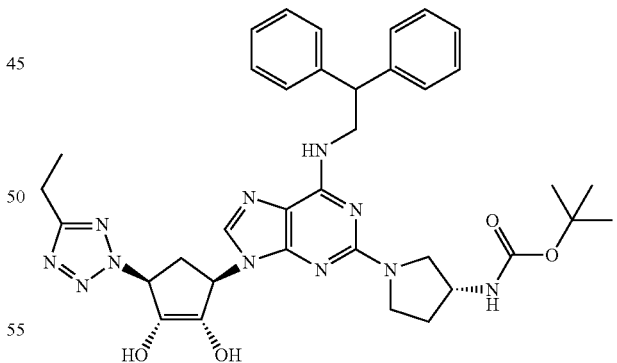

((R)-1-{6-(2,2-Diphenyl-ethylamino)-9-[(1R,4S)-4-(5-ethyl-tetrazol-2-yl)-cyclopent-2-enyl]-9H-purin-2-yl}-pyrrolidin-3-yl)-carbamic acid tert-butyl ester (500 mg) along with N-methylmorpholine-N-oxide (178 mg) is dissolved in THF (5 mL). Osmium tetroxide 4% in water (500 µL) is added to the stirring solution. The reaction is stirred at RT. Analysis by LCMS showed reaction completion after 72 hours. The solvent is removed in vacuo and the residue is portioned between dichloromethane and 0.1 M HCl. The organic layer is washed with water and brine, dried over MgSO₄, filtered and the solvent is removed in vacuo. The title compound is obtained by Flash column chromatography (silica, dichloromethane/methanol 100:1-50:1-25:1). MS (ES+) m/e 696.43 (MH+)

Step 6: 3-[3-((R)-1-{6-[bisphenyl-ethylamino]-9-((1R,2S,3R,4S)-2,3-dihydroxy-4-(5 ethyl-tetrazol-2-yl)-cyclopentyl]9H-purin-2-yl}-[yrrolidin-3-yl)-ureido]-benzenesulphonamide ((R)-1-{6-(2,2-Diphenylethylamino)-9-[(1R,4S)-4-(5-ethyl-tetrazol-2-yl)-2,3-dihydroxy-cyclopentyl]-9H-purin-2-yl}-pyrrolidin-3-yl)-carbamic acid tert-butyl ester is deprotected in methanolic HCl to give the corresponding amine hydrochloride salt. The free amine is obtained by neutralization with aqueous sodium hydrogencarbonate followed by elution from a C18 column with water/methanol gradient. The title compound is then prepared in an analogous manner to Example C1, Step 1 by replacing {(1S,2R,3S,4R)-4-[2-((R)-3-amino-pyrrolidin-1-yl)-6-(2,2-diphenyl-ethylamino)-purin-9-yl]-2,3-dihydroxy-cyclopentyl}-carbamic acid benzyl ester with the above free amine and replacing pyridine-3-isocyanate with Intermediate 5.

Examples XYZ

Examples of the structure XYZ are prepared in a multiparallel sequence of reactions as described below.

Examples XYZ

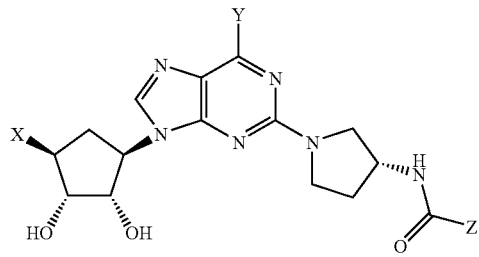

Overall Scheme:

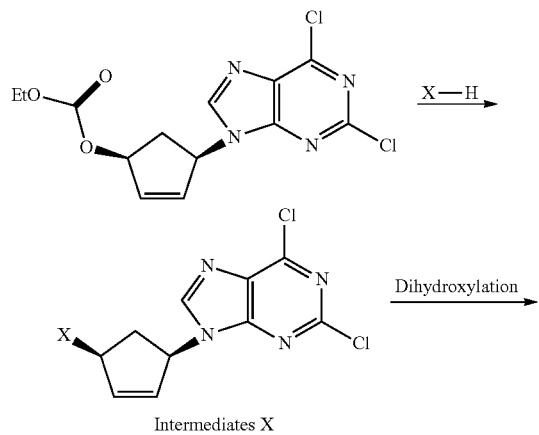

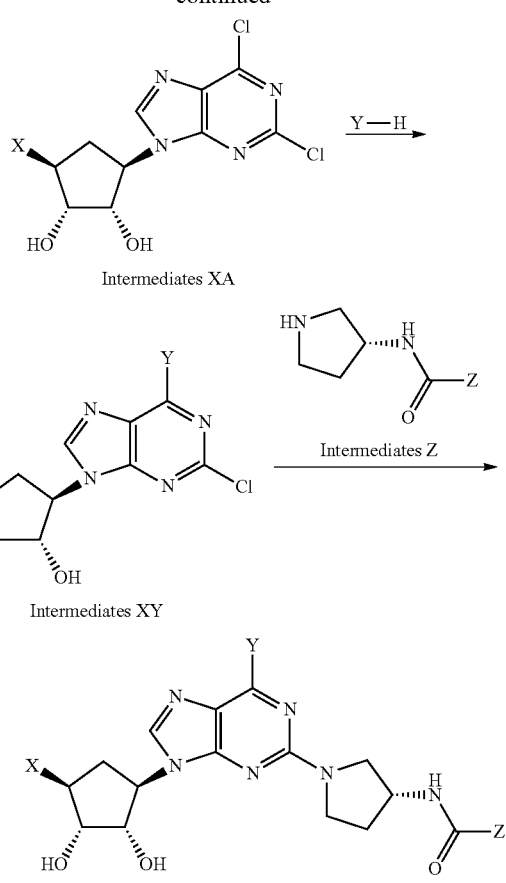

Parallel Step 1

Reaction of Intermediate 1, in an analogous manner to that used in the preparation of Intermediate 3, Step a by replacing 4-hydroxymethylpyrazole with the appropriate heterocycle, individually, with the heterocycles X—H gives the Intermediates X.

Heterocycles X—H

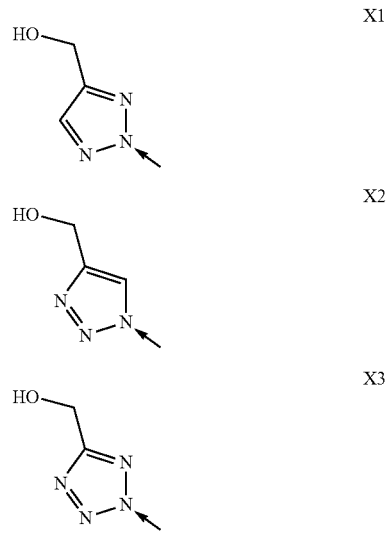

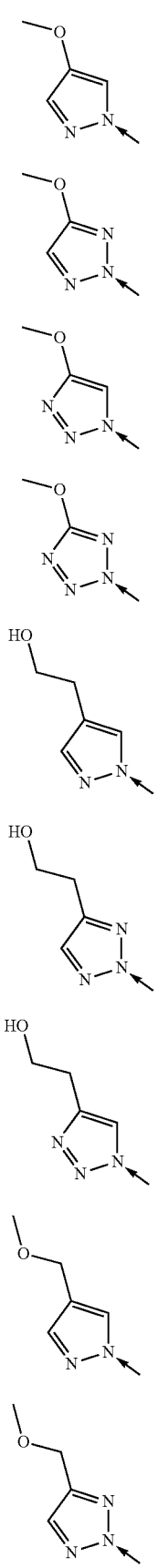

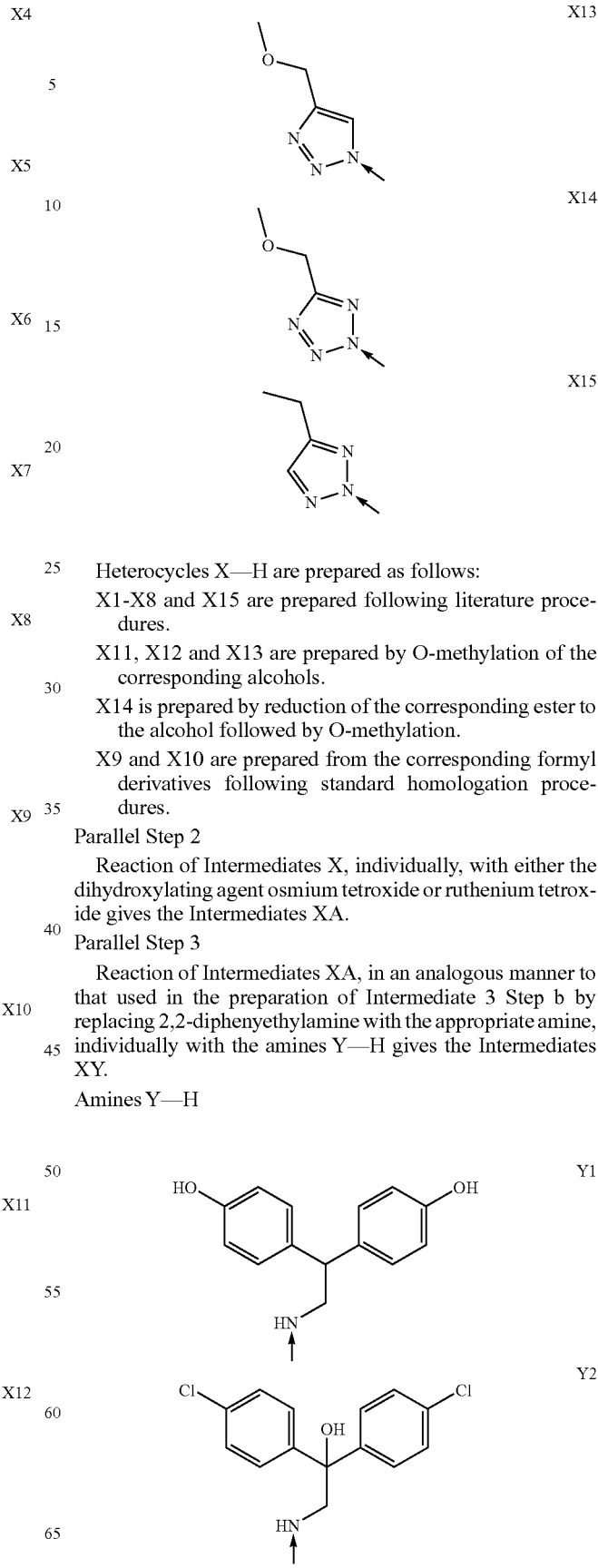

Heterocycles X—H are prepared as follows:

X1-X8 and X15 are prepared following literature procedures.

X11, X12 and X13 are prepared by O-methylation of the corresponding alcohols.

X14 is prepared by reduction of the corresponding ester to the alcohol followed by O-methylation.

X9 and X10 are prepared from the corresponding formyl derivatives following standard homologation procedures.

Parallel Step 2

Reaction of Intermediates X, individually, with either the dihydroxylating agent osmium tetroxide or ruthenium tetroxide gives the Intermediates XA.

Parallel Step 3

Reaction of Intermediates XA, in an analogous manner to that used in the preparation of Intermediate 3 Step b by replacing 2,2-diphenyethylamine with the appropriate amine, individually with the amines Y—H gives the Intermediates XY.

Amines Y—H

-continued
| | |
|---|---|
| 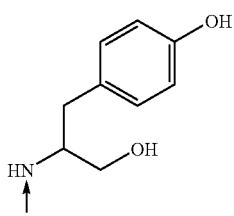 | Y3 |
| 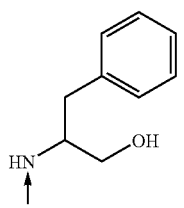 | Y4 |
| 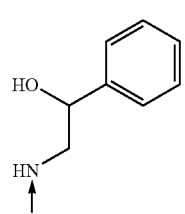 | Y5 |
| 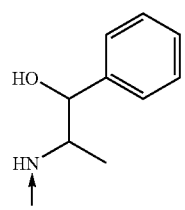 | Y6 |
Parallel Step 4
Intermediates XY are reacted in ethanol at reflux, or in DMSO at 90-110° C., for 18-24 hours, individually, with a 3-fold excess of the appropriate Intermediate Z. The Examples XYZ are isolated following purification by mass directed reversed phase chromatography.
Intermediates Z
Where Z=
| | |
|---|---|
| 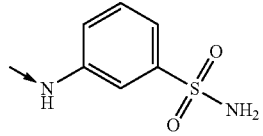 | Z1 |
| 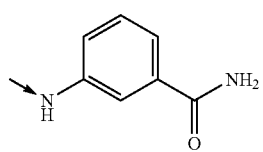 | Z2 |
-continued
| | |
|---|---|
| 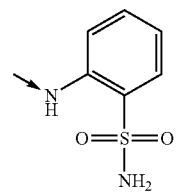 | Z3 |
| 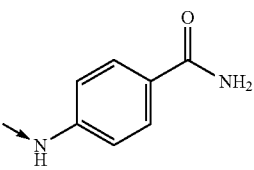 | Z4 |
| 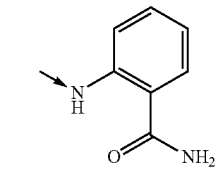 | Z5 |
| 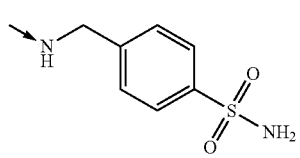 | Z6 |
| 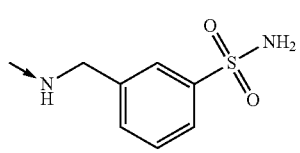 | Z7 |
| 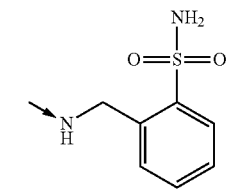 | Z8 |
| 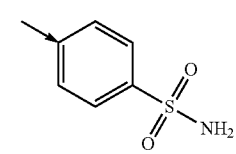 | Z9 |
| 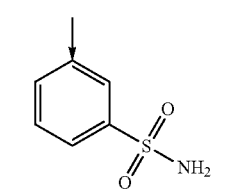 | Z10 |
| 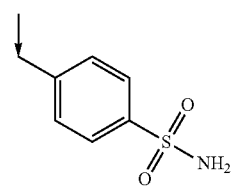 | Z11 |

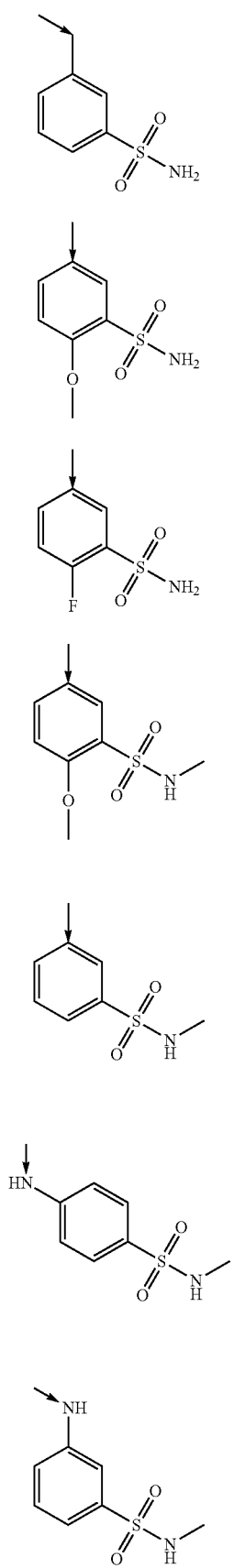
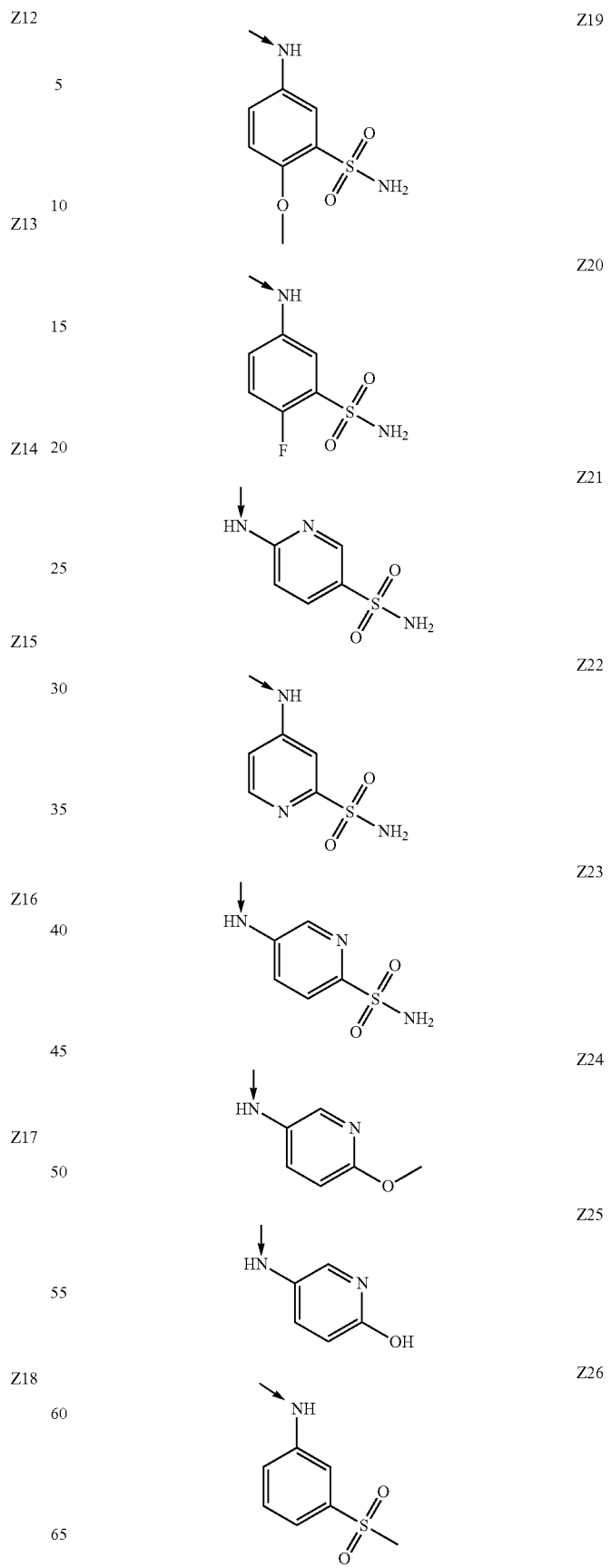

-continued

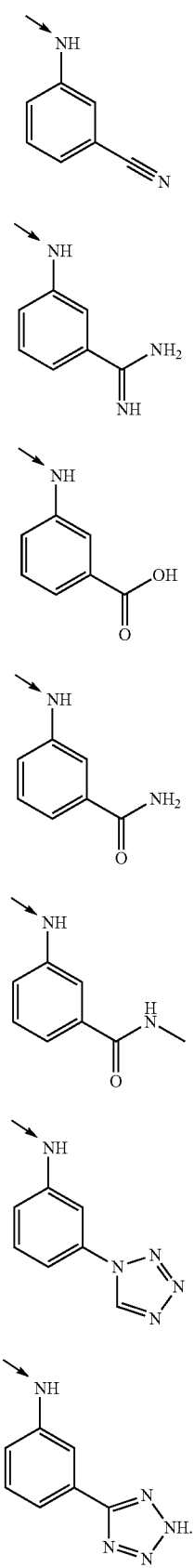

Examples W

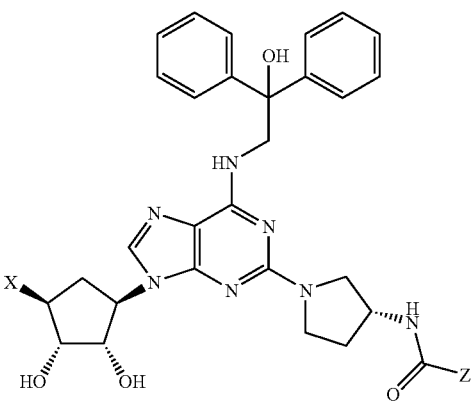

Examples W

For the Examples XYZ, where X=X2 a further hydrogenolysis of the aryl chlorides, individually, by transfer hydrogenation using ammonium formate with a palladium on carbon catalyst in ethanol gives a further series of Examples W.

The invention claimed is:
1. A compound selected from the group consisting of
1-((R)-1-{6-(2,2-Diphenyl-ethylamino)-9-[(2R,3R,4S,5R)-5-(2-ethyl-2H-tetrazol-5-yl)-3,4-dihydroxy-tetrahydro-furan-2-yl]-9H-purin-2-yl}-pyrrolidin-3-yl)-3-(3-hydroxy-benzyl)-urea;
1-((R)-1-{6-(2,2-Diphenyl-ethylamino)-9-[(2R,3R,4S,5R)-5-(2-ethyl-2H-tetrazol-5-yl)-3,4-dihydroxy-tetrahydro-furan-2-yl]-9H-purin-2-yl}-pyrrolidin-3-yl)-3-pyridin-3-yl-urea;
4-[3-((R)-1-{6-(2,2-Diphenyl-ethylamino)-9-[(2R,3R,4S,5R)-5-(2-ethyl-2H-tetrazol-5-yl)-3,4-dihydroxy-tetrahydro-furan-2-yl]-9H-purin-2-yl}-pyrrolidin-3-yl)-ureido]-benzenesulfonamide;
3-[3-((R)-1-{6-(2,2-Diphenyl-ethylamino)-9-[(2R,3R,4S,5R)-5-(2-ethyl-2H-tetrazol-5-yl)-3,4-dihydroxy-tetrahydro-furan-2-yl]-9H-purin-2-yl}-pyrrolidin-3-yl)-ureido]-benzenesulfonamide;
1-{(R)-1-[9-[(2R,3R,4S,5R)-5-(2-Ethyl-2H-tetrazol-5-yl)-3,4-dihydroxy-tetrahydro-furan-2-yl]-6-((S)-1-hydroxymethyl-2-phenyl-ethylamino)-9H-purin-2-yl]-pyrrolidin-3-yl}-3-(3-hydroxy-benzyl)-urea;
1-{(R)-1-[9-[(2R,3R,4S,5R)-5-(2-Ethyl-2H-tetrazol-5-yl)-3,4-dihydroxy-tetrahydro-furan-2-yl]-6-((S)-1-hydroxymethyl-2-phenyl-ethylamino)-9H-purin-2-yl]-pyrrolidin-3-yl}-3-pyridin-3-yl-urea;
4-(3-{(R)-1-[9-[(2R,3R,4S,5R)-5-(2-Ethyl-2H-tetrazol-5-yl)-3,4-dihydroxy-tetrahydro-furan-2-yl]-6-((S)-1-hydroxymethyl-2-phenyl-ethylamino)-9H-purin-2-yl]-pyrrolidin-3-yl}-ureido)-benzenesulfonamide;
3-(3-{(R)-1-[9-[(2R,3R,4S,5R)-5-(2-Ethyl-2H-tetrazol-5-yl)-3,4-dihydroxy-tetrahydro-furan-2-yl]-6-((S)-1-hydroxymethyl-2-phenyl-ethylamino)-9H-purin-2-yl]-pyrrolidin-3-yl}-ureido)-benzenesulfonamide;
1-((R)-1-{6-[2,2-Bis-(4-hydroxy-phenyl)-ethylamino]-9-[(2R,3R,4S,5R)-5-(2-ethyl-2H-tetrazol-5-yl)-3,4-dihydroxy-tetrahydro-furan-2-yl]-9H-purin-2-yl}-pyrrolidin-3-yl)-3-(3-hydroxy-benzyl)-urea;

1-((R)-1-{6-[2,2-Bis-(4-hydroxy-phenyl)-ethylamino]-9-[(2R,3R,4S,5R)-5-(2-ethyl-2H-tetrazol-5-yl)-3,4-dihydroxy-tetrahydro-furan-2-yl]-9H-purin-2-yl}-pyrrolidin-3-yl)-3-pyridin-3-yl-urea;

4-[3-((R)-1-{6-[2,2-Bis-(4-hydroxy-phenyl)-ethylamino]-9-[(2R,3R,4S,5R)-5-(2-ethyl-2H-tetrazol-5-yl)-3,4-dihydroxy-tetrahydro-furan-2-yl]-9H-purin-2-yl}-pyrrolidin-3-yl)-ureido]-benzenesulfonamide;

3-[3-((R)-1-{6-[2,2-Bis-(4-hydroxy-phenyl)-ethylamino]-9-[(2R,3R,4S,5R)-5-(2-ethyl-2H-tetrazol-5-yl)-3,4-dihydroxy-tetrahydro-furan-2-yl]-9H-purin-2-yl}-pyrrolidin-3-yl)-ureido]-benzenesulfonamide;

1-((R)-1-{6-(2,2-Diphenyl-ethylamino)-9-[(2R,3R,4S,5S)-5-(3-ethyl-isoxazol-5-yl)-3,4-dihydroxy-tetrahydro-furan-2-yl]-9H-purin-2-yl}-pyrrolidin-3-yl)-3-(3-hydroxy-benzyl)-urea;

1-((R)-1-{6-(2,2-Diphenyl-ethylamino)-9-[(2R,3R,4S,5S)-5-(3-ethyl-isoxazol-5-yl)-3,4-dihydroxy-tetrahydro-furan-2-yl]-9H-purin-2-yl}-pyrrolidin-3-yl)-3-pyridin-3-yl-urea;

4-[3-((R)-1-{6-(2,2-Diphenyl-ethylamino)-9-[(2R,3R,4S,5S)-5-(3-ethyl-isoxazol-5-yl)-3,4-dihydroxy-tetrahydro-furan-2-yl]-9H-purin-2-yl}-pyrrolidin-3-yl)-ureido]-benzenesulfonamide;

3-[3-((R)-1-{6-(2,2-Diphenyl-ethylamino)-9-[(2R,3R,4S,5S)-5-(3-ethyl-isoxazol-5-yl)-3,4-dihydroxy-tetrahydro-furan-2-yl]-9H-purin-2-yl}-pyrrolidin-3-yl)-ureido]-benzenesulfonamide;

1-{(R)-1-[9-[(2R,3R,4S,5S)-5-(3-Ethyl-isoxazol-5-yl)-3,4-dihydroxy-tetrahydro-furan-2-yl]-6-((S)-1-hydroxymethyl-2-phenyl-ethylamino)-9H-purin-2-yl]-pyrrolidin-3-yl}-3-(3-hydroxy-benzyl)-urea;

1-{(R)-1-[9-[(2R,3R,4S,5S)-5-(3-Ethyl-isoxazol-5-yl)-3,4-dihydroxy-tetrahydro-furan-2-yl]-6-((S)-1-hydroxymethyl-2-phenyl-ethylamino)-9H-purin-2-yl]-pyrrolidin-3-yl}-3-pyridin-3-yl-urea;

4-(3-{(R)-1-[9-[(2R,3R,4S,5S)-5-(3-Ethyl-isoxazol-5-yl)-3,4-dihydroxy-tetrahydro-furan-2-yl]-6-((S)-1-hydroxymethyl-2-phenyl-ethylamino)-9H-purin-2-yl]-pyrrolidin-3-yl}-ureido)-benzenesulfonamide;

3-(3-{(R)-1-[9-[(2R,3R,4S,5S)-5-(3-Ethyl-isoxazol-5-yl)-3,4-dihydroxy-tetrahydro-furan-2-yl]-6-((S)-1-hydroxymethyl-2-phenyl-ethylamino)-9H-purin-2-yl]-pyrrolidin-3-yl}-ureido)-benzenesulfonamide;

1-((R)-1-{6-[2,2-Bis-(4-hydroxy-phenyl)-ethylamino]-9-[(2R,3R,4S,5S)-5-(3-ethyl-isoxazol-5-yl)-3,4-dihydroxy-tetrahydro-furan-2-yl]-9H-purin-2-yl}-pyrrolidin-3-yl)-3-(3-hydroxy-benzyl)-urea;

1-((R)-1-{6-[2,2-Bis-(4-hydroxy-phenyl)-ethylamino]-9-[(2R,3R,4S,5S)-5-(3-ethyl-isoxazol-5-yl)-3,4-dihydroxy-tetrahydro-furan-2-yl]-9H-purin-2-yl}-pyrrolidin-3-yl)-3-pyridin-3-yl-urea;

4-[3-((R)-1-{6-[2,2-Bis-(4-hydroxy-phenyl)-ethylamino]-9-[(2R,3R,4S,5S)-5-(3-ethyl-isoxazol-5-yl)-3,4-dihydroxy-tetrahydro-furan-2-yl]-9H-purin-2-yl}-pyrrolidin-3-yl)-ureido]-benzenesulfonamide;

3-[3-((R)-1-{6-[2,2-Bis-(4-hydroxy-phenyl)-ethylamino]-9-[(2R,3R,4S,5S)-5-(3-ethyl-isoxazol-5-yl)-3,4-dihydroxy-tetrahydro-furan-2-yl]-9H-purin-2-yl}-pyrrolidin-3-yl)-ureido]-benzenesulfonamide;

1-{(R)-1-[9-[(2R,3R,4S,5S)-3,4-Dihydroxy-5-(3-hydroxymethyl-isoxazol-5-yl)-tetrahydro-furan-2-yl]-6-(2,2-diphenyl-ethylamino)-9H-purin-2-yl]-pyrrolidin-3-yl}-3-(3-hydroxy-benzyl)-urea;

1-{(R)-1-[9-[(2R,3R,4S,5S)-3,4-Dihydroxy-5-(3-hydroxymethyl-isoxazol-5-yl)-tetrahydro-furan-2-yl]-6-(2,2-diphenyl-ethylamino)-9H-purin-2-yl]-pyrrolidin-3-yl}-3-pyridin-3-yl-urea;

4-(3-{(R)-1-[9-[(2R,3R,4S,5S)-3,4-Dihydroxy-5-(3-hydroxymethyl-isoxazol-5-yl)-tetrahydro-furan-2-yl]-6-(2,2-diphenyl-ethylamino)-9H-purin-2-yl]-pyrrolidin-3-yl}-ureido)-benzenesulfonamide;

3-(3-{(R)-1-[9-[(2R,3R,4S,5S)-3,4-Dihydroxy-5-(3-hydroxymethyl-isoxazol-5-yl)-tetrahydro-furan-2-yl]-6-(2,2-diphenyl-ethylamino)-9H-purin-2-yl]-pyrrolidin-3-yl}-ureido)-benzenesulfonamide;

1-{(R)-1-[9-[(2R,3R,4S,5S)-3,4-Dihydroxy-5-(3-hydroxymethyl-isoxazol-5-yl)-tetrahydro-furan-2-yl]-6-((S)-1-hydroxymethyl-2-phenyl-ethylamino)-9H-purin-2-yl]-pyrrolidin-3-yl}-3-(3-hydroxy-benzyl)-urea;

1-{(R)-1-[9-[(2R,3R,4S,5S)-3,4-Dihydroxy-5-(3-hydroxymethyl-isoxazol-5-yl)-tetrahydro-furan-2-yl]-6-((S)-1-hydroxymethyl-2-phenyl-ethylamino)-9H-purin-2-yl]-pyrrolidin-3-yl}-3-pyridin-3-yl-urea;

4-(3-{(R)-1-[9-[(2R,3R,4S,5S)-3,4-Dihydroxy-5-(3-hydroxymethyl-isoxazol-5-yl)-tetrahydro-furan-2-yl]-6-((S)-1-hydroxymethyl-2-phenyl-ethylamino)-9H-purin-2-yl]-pyrrolidin-3-yl}-ureido)-benzenesulfonamide;

3-(3-{(R)-1-[9-[(2R,3R,4S,5S)-3,4-Dihydroxy-5-(3-hydroxymethyl-isoxazol-5-yl)-tetrahydro-furan-2-yl]-6-((S)-1-hydroxymethyl-2-phenyl-ethylamino)-9H-purin-2-yl]-pyrrolidin-3-yl}-ureido)-benzenesulfonamide;

1-((R)-1-{6-[2,2-Bis-(4-hydroxy-phenyl)-ethylamino]-9-[(2R,3R,4S,5S)-3,4-dihydroxy-5-(3-hydroxymethyl-isoxazol-5-yl)-tetrahydro-furan-2-yl]-9H-purin-2-yl}-pyrrolidin-3-yl)-3-(3-hydroxy-benzyl)-urea;

1-((R)-1-{6-[2,2-Bis-(4-hydroxy-phenyl)-ethylamino]-9-[(2R,3R,4S,5S)-3,4-dihydroxy-5-(3-hydroxymethyl-isoxazol-5-yl)-tetrahydro-furan-2-yl]-9H-purin-2-yl}-pyrrolidin-3-yl)-3-pyridin-3-yl-urea;

4-[3-((R)-1-{6-[2,2-Bis-(4-hydroxy-phenyl)-ethylamino]-9-[(2R,3R,4S,5S)-3,4-dihydroxy-5-(3-hydroxymethyl-isoxazol-5-yl)-tetrahydro-furan-2-yl]-9H-purin-2-yl}-pyrrolidin-3-yl)-ureido]-benzenesulfonamide;

3-[3-((R)-1-{6-[2,2-Bis-(4-hydroxy-phenyl)-ethylamino]-9-[(2R,3R,4S,5S)-3,4-dihydroxy-5-(3-hydroxymethyl-isoxazol-5-yl)-tetrahydro-furan-2-yl]-9H-purin-2-yl}-pyrrolidin-3-yl)-ureido]-benzenesulfonamide;

1-{(R)-1-[9-{(2R,3R,4S,5R)-3,4-Dihydroxy-5-[2-(2-hydroxy-ethyl)-2H-tetrazol-5-yl]-tetrahydro-furan-2-yl}-6-(2,2-diphenyl-ethylamino)-9H-purin-2-yl]-pyrrolidin-3-yl}-3-(3-hydroxy-benzyl)-urea;

1-{(R)-1-[9-{(2R,3R,4S,5R)-3,4-Dihydroxy-5-[2-(2-hydroxy-ethyl)-2H-tetrazol-5-yl]-tetrahydro-furan-2-yl}-6-(2,2-diphenyl-ethylamino)-9H-purin-2-yl]-pyrrolidin-3-yl}-3-pyridin-3-yl-urea;

4-(3-{(R)-1-[9-{(2R,3R,4S,5R)-3,4-Dihydroxy-5-[2-(2-hydroxy-ethyl)-2H-tetrazol-5-yl]-tetrahydro-furan-2-yl}-6-(2,2-diphenyl-ethylamino)-9H-purin-2-yl]-pyrrolidin-3-yl}-ureido)-benzenesulfonamide;

3-(3-{(R)-1-[9-{(2R,3R,4S,5R)-3,4-Dihydroxy-5-[2-(2-hydroxy-ethyl)-2H-tetrazol-5-yl]-tetrahydro-furan-2-yl}-6-(2,2-diphenyl-ethylamino)-9H-purin-2-yl]-pyrrolidin-3-yl}-ureido)-benzenesulfonamide;

1-{(R)-1-[9-{(2R,3R,4S,5R)-3,4-Dihydroxy-5-[2-(2-hydroxy-ethyl)-2H-tetrazol-5-yl]-tetrahydro-furan-2-yl}-6-((S)-1-hydroxymethyl-2-phenyl-ethylamino)-9H-purin-2-yl]-pyrrolidin-3-yl}-3-(3-hydroxy-benzyl)-urea;

1-{(R)-1-[9-{(2R,3R,4S,5R)-3,4-Dihydroxy-5-[2-(2-hydroxy-ethyl)-2H-tetrazol-5-yl]-tetrahydro-furan-2-yl}-6-((S)-1-hydroxymethyl-2-phenyl-ethylamino)-9H-purin-2-yl]-pyrrolidin-3-yl}-3-pyridin-3-yl-urea;

4-(3-{(R)-1-[9-{(2R,3R,4S,5R)-3,4-Dihydroxy-5-[2-(2-hydroxy-ethyl)-2H-tetrazol-5-yl]-tetrahydro-furan-2-yl}-6-((S)-1-hydroxymethyl-2-phenyl-ethylamino)-9H-purin-2-yl]-pyrrolidin-3-yl}-ureido)-benzenesulfonamide;

3-(3-{(R)-1-[9-{(2R,3R,4S,5R)-3,4-Dihydroxy-5-[2-(2-hydroxy-ethyl)-2H-tetrazol-5-yl]-tetrahydro-furan-2-yl}-6-((S)-1-hydroxymethyl-2-phenyl-ethylamino)-9H-purin-2-yl]-pyrrolidin-3-yl}-ureido)-benzenesulfonamide;

1-[(R)-1-(6-[2,2-Bis-(4-hydroxy-phenyl)-ethylamino]-9-{(2R,3R,4S,5R)-3,4-dihydroxy-5-[2-(2-hydroxy-ethyl)-2H-tetrazol-5-yl]-tetrahydro-furan-2-yl}-9H-purin-2-yl)-pyrrolidin-3-yl]-3-(3-hydroxy-benzyl)-urea;

1-[(R)-1-(6-[2,2-Bis-(4-hydroxy-phenyl)-ethylamino]-9-{(2R,3R,4S,5R)-3,4-dihydroxy-5-[2-(2-hydroxy-ethyl)-2H-tetrazol-5-yl]-tetrahydro-furan-2-yl}-9H-purin-2-yl)-pyrrolidin-3-yl]-3-pyridin-3-yl-urea;

4-{3-[(R)-1-(6-[2,2-Bis-(4-hydroxy-phenyl)-ethylamino]-9-{(2R,3R,4S,5R)-3,4-dihydroxy-5-[2-(2-hydroxy-ethyl)-2H-tetrazol-5-yl]-tetrahydro-furan-2-yl-]-9H-purin-2-yl)-pyrrolidin-3-yl]-ureido}-benzenesulfonamide;

3-{3-[(R)-1-(6-[2,2-Bis-(4-hydroxy-phenyl)-ethylamino]-9-{(2R,3R,4S,5R)-3,4-dihydroxy-5-[2-(2-hydroxy-ethyl)-2H-tetrazol-5-yl]-tetrahydro-furan-2-yl]-9H-purin-2-yl)-pyrrolidin-3-yl]-ureido}-benzenesulfonamide;

1-{(R)-1-[9-[(1R,2S,3R,4S)-2,3-Dihydroxy-4-((S)-4-methyl-2,5-dioxo-imidazolidin-1-yl)-cyclopentyl]-6-(2,2-diphenyl-ethylamino)-9H-purin-2-yl]-pyrrolidin-3-yl}-3-pyridin-3-yl-urea;

1-{(R)-1-[9-[(1R,2S,3R,4S)-4-(2,5-Dioxo-imidazolidin-1-yl)-2,3-dihydroxy-cyclopentyl]-6-(2,2-diphenyl-ethylamino)-9H-purin-2-yl]-pyrrolidin-3-yl}-3-pyridin-3-yl-urea;

1-{(R)-1-[9-[(1R,2S,3R,4S)-2,3-Dihydroxy-4-((S)-4-methyl-2,5-dioxo-imidazolidin-1-yl)-cyclopentyl]-6-(2,2-diphenyl-ethylamino)-9H-purin-2-yl]-pyrrolidin-3-yl}-3-(3-hydroxy-benzyl)-urea;

4-(3-{(R)-1-[9-[(1R,2S,3R,4S)-2,3-Dihydroxy-4-((S)-4-methyl-2,5-dioxo-imidazolidin-1-yl)-cyclopentyl]-6-(2,2-diphenyl-ethylamino)-9H-purin-2-yl]-pyrrolidin-3-yl}-ureido)-benzenesulfonamide;

3-(3-{(R)-1-[9-[(1R,2S,3R,4S)-2,3-Dihydroxy-4-((S)-4-methyl-2,5-dioxo-imidazolidin-1-yl)-cyclopentyl]-6-(2,2-diphenyl-ethylamino)-9H-purin-2-yl]-pyrrolidin-3-yl}-ureido)-benzenesulfonamide;

1-{(R)-1-[9-[(1R,2S,3R,4S)-2,3-Dihydroxy-4-((S)-4-methyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-3-pyridin-3-yl-urea;

1-{(R)-1-[9-[(1R,2S,3R,4S)-2,3-Dihydroxy-4-((S)-4-methyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-3-(3-hydroxy-benzyl)-urea;

4-(3-{(R)-1-[9-[(1R,2S,3R,4S)-2,3-Dihydroxy-4-((S)-4-methyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-ureido)-benzenesulfonamide;

3-(3-{(R)-1-[9-[(1R,2S,3R,4S)-2,3-Dihydroxy-4-((S)-4-methyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-ureido)-benzenesulfonamide;

1-((R)-1-{6-[2,2-Bis-(4-hydroxy-phenyl)-ethylamino]-9-[(1R,2S,3R,4S)-2,3-dihydroxy-4-((S)-4-methyl-2,5-dioxo-imidazolidin-1-yl)-cyclopentyl]-9H-purin-2-yl}-pyrrolidin-3-yl)-3-pyridin-3-yl-urea;

1-((R)-1-{6-[2,2-Bis-(4-hydroxy-phenyl)-ethylamino]-9-[(1R,2S,3R,4S)-2,3-dihydroxy-4-((S)-4-methyl-2,5-dioxo-imidazolidin-1-yl)-cyclopentyl]-9H-purin-2-yl}-pyrrolidin-3-yl)-3-(3-hydroxy-benzyl)-urea;

4-[3-((R)-1-{6-[2,2-Bis-(4-hydroxy-phenyl)-ethylamino]-9-[(1R,2S,3R,4S)-2,3-dihydroxy-4-((S)-4-methyl-2,5-dioxo-imidazolidin-1-yl)-cyclopentyl]-9H-purin-2-yl}-pyrrolidin-3-yl)-ureido]-benzenesulfonamide;

3-[3-((R)-1-{6-[2,2-Bis-(4-hydroxy-phenyl)-ethylamino]-9-[(1R,2S,3R,4S)-2,3-dihydroxy-4-((S)-4-methyl-2,5-dioxo-imidazolidin-1-yl)-cyclopentyl]-9H-purin-2-yl}-pyrrolidin-3-yl)-ureido]-benzenesulfonamide;

1-{(R)-1-[9-[(1R,2S,3R,4S)-4-(2,5-Dioxo-imidazolidin-1-yl)-2,3-dihydroxy-cyclopentyl]-6-(2,2-diphenyl-ethylamino)-9H-purin-2-yl]-pyrrolidin-3-yl}-3-(3-hydroxy-benzyl)-urea;

4-(3-{(R)-1-[9-[(1R,2S,3R,4S)-4-(2,5-Dioxo-imidazolidin-1-yl)-2,3-dihydroxy-cyclopentyl]-6-(2,2-diphenyl-ethylamino)-9H-purin-2-yl]-pyrrolidin-3-yl}-ureido)-benzenesulfonamide;

3-(3-{(R)-1-[9-[(1R,2S,3R,4S)-4-(2,5-Dioxo-imidazolidin-1-yl)-2,3-dihydroxy-cyclopentyl]-6-(2,2-diphenyl-ethylamino)-9H-purin-2-yl]-pyrrolidin-3-yl}-ureido)-benzenesulfonamide;

1-{(R)-1-[9-[(1R,2S,3R,4S)-4-(2,5-Dioxo-imidazolidin-1-yl)-2,3-dihydroxy-cyclopentyl]-6-((S)-1-hydroxymethyl-2-phenyl-ethylamino)-9H-purin-2-yl]-pyrrolidin-3-yl}-3-pyridin-3-yl-urea;

1-{(R)-1-[9-[(1R,2S,3R,4S)-4-(2,5-Dioxo-imidazolidin-1-yl)-2,3-dihydroxy-cyclopentyl]-6-((S)-1-hydroxymethyl-2-phenyl-ethylamino)-9H-purin-2-yl]-pyrrolidin-3-yl}-3-(3-hydroxy-benzyl)-urea;

4-(3-{(R)-1-[9-[(1R,2S,3R,4S)-4-(2,5-Dioxo-imidazolidin-1-yl)-2,3-dihydroxy-cyclopentyl]-6-((S)-1-hydroxymethyl-2-phenyl-ethylamino)-9H-purin-2-yl]-pyrrolidin-3-yl}-ureido)-benzenesulfonamide;

3-(3-{(R)-1-[9-[(1R,2S,3R,4S)-4-(2,5-Dioxo-imidazolidin-1-yl)-2,3-dihydroxy-cyclopentyl]-6-((S)-1-hydroxymethyl-2-phenyl-ethylamino)-9H-purin-2-yl]-pyrrolidin-3-yl}-ureido)-benzenesulfonamide;

1-((R)-1-{6-[2,2-Bis-(4-hydroxy-phenyl)-ethylamino]-9-[(1R,2S,3R,4S)-4-(2,5-dioxo-imidazolidin-1-yl)-2,3-dihydroxy-cyclopentyl]-9H-purin-2-yl}-pyrrolidin-3-yl)-3-pyridin-3-yl-urea;

1-((R)-1-{6-[2,2-Bis-(4-hydroxy-phenyl)-ethylamino]-9-[(1R,2S,3R,4S)-4-(2,5-dioxo-imidazolidin-1-yl)-2,3-dihydroxy-cyclopentyl]-9H-purin-2-yl}-pyrrolidin-3-yl)-3-(3-hydroxy-benzyl)-urea;

4-[3-((R)-1-{6-[2,2-Bis-(4-hydroxy-phenyl)-ethylamino]-9-[(1R,2S,3R,4S)-4-(2,5-dioxo-imidazolidin-1-yl)-2,3-dihydroxy-cyclopentyl]-9H-purin-2-yl}-pyrrolidin-3-yl)-ureido]-benzenesulfonamide;

3-[3-((R)-1-{6-[2,2-Bis-(4-hydroxy-phenyl)-ethylamino]-9-[(1R,2S,3R,4S)-4-(2,5-dioxo-imidazolidin-1-yl)-2,3-dihydroxy-cyclopentyl]-9H-purin-2-yl}-pyrrolidin-3-yl)-ureido]-benzenesulfonamide;

1-{(R)-1-[9-[(1R,2S,3R,4S)-2,3-Dihydroxy-4-(3-methyl-2,5-dioxo-imidazolidin-1-yl)-cyclopentyl]-6-(2,2-diphenyl-ethylamino)-9H-purin-2-yl]-pyrrolidin-3-yl}-3-pyridin-3-yl-urea;

1-{(R)-1-[9-[(1R,2S,3R,4S)-2,3-Dihydroxy-4-(3-methyl-2,5-dioxo-imidazolidin-1-yl)-cyclopentyl]-6-(2,2-diphenyl-ethylamino)-9H-purin-2-yl]-pyrrolidin-3-yl}-3-(3-hydroxy-benzyl)-urea;

4-(3-{(R)-1-[9-[(1R,2S,3R,4S)-2,3-Dihydroxy-4-(3-methyl-2,5-dioxo-imidazolidin-1-yl)-cyclopentyl]-6-(2,2-diphenyl-ethylamino)-9H-purin-2-yl]-pyrrolidin-3-yl}-ureido)-benzenesulfonamide;

3-(3-{(R)-1-[9-[(1R,2S,3R,4S)-2,3-Dihydroxy-4-(3-methyl-2,5-dioxo-imidazolidin-1-yl)-cyclopentyl]-6-(2,2-diphenyl-ethylamino)-9H-purin-2-yl]-pyrrolidin-3-yl}-ureido)-benzenesulfonamide;

1-{(R)-1-[9-[(1R,2S,3R,4S)-2,3-Dihydroxy-4-(3-methyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-3-pyridin-3-yl-urea;

1-{(R)-1-[9-[(1R,2S,3R,4S)-2,3-Dihydroxy-4-(3-methyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-3-(3-hydroxy-benzyl)-urea;

4-(3-{(R)-1-[9-[(1R,2S,3R,4S)-2,3-Dihydroxy-4-(3-methyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-ureido)-benzenesulfonamide;

3-(3-{(R)-1-[9-[(1R,2S,3R,4S)-2,3-Dihydroxy-4-(3-methyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-ureido)-benzenesulfonamide;

1-((R)-1-{6-[2,2-Bis-(4-hydroxy-phenyl)-ethylamino]-9-[(1R,2S,3R,4S)-2,3-dihydroxy-4-(3-methyl-2,5-dioxo-imidazolidin-1-yl)-cyclopentyl]-9H-purin-2-yl}-pyrrolidin-3-yl)-3-pyridin-3-yl-urea;

1-((R)-1-{6-[2,2-Bis-(4-hydroxy-phenyl)-ethylamino]-9-[(1R,2S,3R,4S)-2,3-dihydroxy-4-(3-methyl-2,5-dioxo-imidazolidin-1-yl)-cyclopentyl]-9H-purin-2-yl}-pyrrolidin-3-yl)-3-(3-hydroxy-benzyl)-urea;

4-[3-((R)-1-{6-[2,2-Bis-(4-hydroxy-phenyl)-ethylamino]-9-[(1R,2S,3R,4S)-2,3-dihydroxy-4-(3-methyl-2,5-dioxo-imidazolidin-1-yl)-cyclopentyl]-9H-purin-2-yl}-pyrrolidin-3-yl)-ureido]-benzenesulfonamide;

3-[3-((R)-1-{6-[2,2-Bis-(4-hydroxy-phenyl)-ethylamino]-9-[(1R,2S,3R,4S)-2,3-dihydroxy-4-(3-methyl-2,5-dioxo-imidazolidin-1-yl)-cyclopentyl]-9H-purin-2-yl}-pyrrolidin-3-yl)-ureido]-benzenesulfonamide;

1-{(R)-1-[9-[(1R,2S,3R,4S)-2,3-Dihydroxy-4-(4-hydroxymethyl-2,5-dioxo-imidazolidin-1-yl)-cyclopentyl]-6-(2,2-diphenyl-ethylamino)-9H-purin-2-yl]-pyrrolidin-3-yl}-3-pyridin-3-yl-urea;

1-{(R)-1-[9-[(1R,2S,3R,4S)-2,3-Dihydroxy-4-(4-hydroxymethyl-2,5-dioxo-imidazolidin-1-yl)-cyclopentyl]-6-(2,2-diphenyl-ethylamino)-9H-purin-2-yl]-pyrrolidin-3-yl}-3-(3-hydroxy-benzyl)-urea;

4-(3-{(R)-1-[9-[(1R,2S,3R,4S)-2,3-Dihydroxy-4-(4-hydroxymethyl-2,5-dioxo-imidazolidin-1-yl)-cyclopentyl]-6-(2,2-diphenyl-ethylamino)-9H-purin-2-yl]-pyrrolidin-3-yl}-ureido)-benzenesulfonamide;

3-(3-{(R)-1-[9-[(1R,2S,3R,4S)-2,3-Dihydroxy-4-(4-hydroxymethyl-2,5-dioxo-imidazolidin-1-yl)-cyclopentyl]-6-(2,2-diphenyl-ethylamino)-9H-purin-2-yl]-pyrrolidin-3-yl}-ureido)-benzenesulfonamide;

1-{(R)-1-[9-[(1R,2S,3R,4S)-2,3-Dihydroxy-4-(4-hydroxymethyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-3-pyridin-3-yl-urea;

1-{(R)-1-[9-[(1R,2S,3R,4S)-2,3-Dihydroxy-4-(4-hydroxymethyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-3-(3-hydroxy-benzyl)-urea;

4-(3-{(R)-1-[9-[(1R,2S,3R,4S)-2,3-Dihydroxy-4-(4-hydroxymethyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-ureido)-benzenesulfonamide;

3-(3-{(R)-1-[9-[(1R,2S,3R,4S)-2,3-Dihydroxy-4-(4-hydroxymethyl-2,5-dioxo-imidazolidin-1-yl)-cyclopentyl]-6-((S)-1-hydroxymethyl-2-phenyl-ethylamino)-9H-purin-2-yl]-pyrrolidin-3-yl}-ureido)-benzenesulfonamide;

1-((R)-1-{6-[2,2-Bis-(4-hydroxy-phenyl)-ethylamino]-9-[(1R,2S,3R,4S)-2,3-dihydroxy-4-(4-hydroxymethyl-2,5-dioxo-imidazolidin-1-yl)-cyclopentyl]-9H-purin-2-yl}-pyrrolidin-3-yl)-3-pyridin-3-yl-urea;

1-((R)-1-{6-[2,2-Bis-(4-hydroxy-phenyl)-ethylamino]-9-[(1R,2S,3R,4S)-2,3-dihydroxy-4-(4-hydroxymethyl-2,5-dioxo-imidazolidin-1-yl)-cyclopentyl]-9H-purin-2-yl}-pyrrolidin-3-yl)-3-(3-hydroxy-benzyl)-urea;

4-[3-((R)-1-{6-[2,2-Bis-(4-hydroxy-phenyl)-ethylamino]-9-[(1R,2S,3R,4S)-2,3-dihydroxy-4-(4-hydroxymethyl-2,5-dioxo-imidazolidin-1-yl)-cyclopentyl]-9H-purin-2-yl}-pyrrolidin-3-yl)-ureido]-benzenesulfonamide;

3-[3-((R)-1-{6-[2,2-Bis-(4-hydroxy-phenyl)-ethylamino]-9-[(1R,2S,3R,4S)-2,3-dihydroxy-4-(4-hydroxymethyl-2,5-dioxo-imidazolidin-1-yl)-cyclopentyl]-9H-purin-2-yl}-pyrrolidin-3-yl)-ureido]-benzenesulfonamide;

1-{(R)-1-[9-[(1R,2S,3R,4S)-2,3-Dihydroxy-4-(4-hydroxymethyl-pyrazol-1-yl)-cyclopentyl]-6-(2,2-diphenyl-ethylamino)-9H-purin-2-yl]-pyrrolidin-3-yl}-3-pyridin-3-yl-urea;

1-{(R)-1-[9-[(1R,2S,3R,4S)-2,3-Dihydroxy-4-(4-hydroxymethyl-pyrazol-1-yl)-cyclopentyl]-6-(2,2-diphenyl-ethylamino)-9H-purin-2-yl]-pyrrolidin-3-yl}-3-(3-hydroxy-benzyl)-urea;

4-(3-{(R)-1-[9-[(1R,2S,3R,4S)-2,3-Dihydroxy-4-(4-hydroxymethyl-pyrazol-1-yl)-cyclopentyl]-6-(2,2-diphenyl-ethylamino)-9H-purin-2-yl]-pyrrolidin-3-yl}-ureido)-benzenesulfonamide;

3-(3-{(R)-1-[9-[(1R,2S,3R,4S)-2,3-Dihydroxy-4-(4-hydroxymethyl-pyrazol-1-yl)-cyclopentyl]-6-(2,2-diphenyl-ethylamino)-9H-purin-2-yl]-pyrrolidin-3-yl}-ureido)-benzenesulfonamide;

1-{(R)-1-[9-[(1R,2S,3R,4S)-2,3-Dihydroxy-4-(4-hydroxymethyl-pyrazol-1-yl)-cyclopentyl]-6-((S)-1-hydroxymethyl-2-phenyl-ethylamino)-9H-purin-2-yl]-pyrrolidin-3-yl}-3-pyridin-3-yl-urea;

1-{(R)-1-[9-[(1R,2S,3R,4S)-2,3-Dihydroxy-4-(4-hydroxymethyl-pyrazol-1-yl)-cyclopentyl]-6-((S)-1-hydroxymethyl-2-phenyl-ethylamino)-9H-purin-2-yl]-pyrrolidin-3-yl}-3-(3-hydroxy-benzyl)-urea;

4-(3-{(R)-1-[9-[(1R,2S,3R,4S)-2,3-Dihydroxy-4-(4-hydroxymethyl-pyrazol-1-yl)-cyclopentyl]-6-((S)-1-hydroxymethyl-2-phenyl-ethylamino)-9H-purin-2-yl]-pyrrolidin-3-yl}-ureido)-benzenesulfonamide;

3-(3-{(R)-1-[9-[(1R,2S,3R,4S)-2,3-Dihydroxy-4-(4-hydroxymethyl-pyrazol-1-yl)-cyclopentyl]-6-((S)-1-hydroxymethyl-2-phenyl-ethylamino)-9H-purin-2-yl]-pyrrolidin-3-yl}-ureido)-benzenesulfonamide;

1-((R)-1-{6-[2,2-Bis-(4-hydroxy-phenyl)-ethylamino]-9-[(1R,2S,3R,4S)-2,3-dihydroxy-4-(4-hydroxymethyl-pyrazol-1-yl)-cyclopentyl]-9H-purin-2-yl}-pyrrolidin-3-yl)-3-pyridin-3-yl-urea;

1-((R)-1-{6-[2,2-Bis-(4-hydroxy-phenyl)-ethylamino]-9-[(1R,2S,3R,4S)-2,3-dihydroxy-4-(4-hydroxymethyl-pyrazol-1-yl)-cyclopentyl]-9H-purin-2-yl}-pyrrolidin-3-yl)-3-(3-hydroxy-benzyl)-urea;

4-[3-((R)-1-{6-[2,2-Bis-(4-hydroxy-phenyl)-ethylamino]-9-[(1R,2S,3R,4S)-2,3-dihydroxy-4-(4-hydroxymethyl-pyrazol-1-yl)-cyclopentyl]-9H-purin-2-yl}-pyrrolidin-3-yl)-ureido]-benzenesulfonamide;

3-[3-((R)-1-{6-[2,2-Bis-(4-hydroxy-phenyl)-ethylamino]-9-[(1R,2S,3R,4S)-2,3-dihydroxy-4-(4-hydroxymethyl-pyrazol-1-yl)-cyclopentyl]-9H-purin-2-yl}-pyrrolidin-3-yl)-ureido]-benzenesulfonamide;

1-{(R)-1-[9-[(1R,2S,3R,4S)-2,3-Dihydroxy-4-(4-hydroxymethyl-[1,2,3]triazol-2-yl)-cyclopentyl]-6-(2,2-diphenyl-ethylamino)-9H-purin-2-yl]-pyrrolidin-3-yl}-3-pyridin-3-yl-urea;

1-{(R)-1-[9-[(1R,2S,3R,4S)-2,3-Dihydroxy-4-(4-hydroxymethyl-[1,2,3]triazol-2-yl)-cyclopentyl]-6-(2,2-diphenyl-ethylamino)-9H-purin-2-yl]-pyrrolidin-3-yl}-3-(3-hydroxy-benzyl)-urea;

4-(3-{(R)-1-[9-[(1R,2S,3R,4S)-2,3-Dihydroxy-4-(4-hydroxymethyl-[1,2,3]triazol-2-yl)-cyclopentyl]-6-(2,2-diphenyl-ethylamino)-9H-purin-2-yl]-pyrrolidin-3-yl}-ureido)-benzenesulfonamide;

3-(3-{(R)-1-[9-[(1R,2S,3R,4S)-2,3-Dihydroxy-4-(4-hydroxymethyl-[1,2,3]triazol-2-yl)-cyclopentyl]-6-(2,2-diphenyl-ethylamino)-9H-purin-2-yl]-pyrrolidin-3-yl}-ureido)-benzenesulfonamide;

1-{(R)-1-[9-[(1R,2S,3R,4S)-2,3-Dihydroxy-4-(4-hydroxymethyl-[1,2,3]triazol-2-yl)-cyclopentyl]-6-((S)-1-hydroxymethyl-2-phenyl-ethylamino)-9H-purin-2-yl]-pyrrolidin-3-yl}-3-pyridin-3-yl-urea;

1-{(R)-1-[9-[(1R,2S,3R,4S)-2,3-Dihydroxy-4-(4-hydroxymethyl-[1,2,3]triazol-2-yl)-cyclopentyl]-6-((S)-1-hydroxymethyl-2-phenyl-ethylamino)-9H-purin-2-yl]-pyrrolidin-3-yl}-3-(3-hydroxy-benzyl)-urea;

4-(3-{(R)-1-[9-[(1R,2S,3R,4S)-2,3-Dihydroxy-4-(4-hydroxymethyl-[1,2,3]triazol-2-yl)-cyclopentyl]-6-((S)-1-hydroxymethyl-2-phenyl-ethylamino)-9H-purin-2-yl]-pyrrolidin-3-yl}-ureido)-benzenesulfonamide;

3-(3-{(R)-1-[9-[(1R,2S,3R,4S)-2,3-Dihydroxy-4-(4-hydroxymethyl-[1,2,3]triazol-2-yl)-cyclopentyl]-6-((S)-1-hydroxymethyl-2-phenyl-ethylamino)-9H-purin-2-yl]-pyrrolidin-3-yl}-ureido)-benzenesulfonamide;

1-((R)-1-{6-[2,2-Bis-(4-hydroxy-phenyl)-ethylamino]-9-[(1R,2S,3R,4S)-2,3-dihydroxy-4-(4-hydroxymethyl-[1,2,3]triazol-2-yl)-cyclopentyl]-9H-purin-2-yl}-pyrrolidin-3-yl)-3-pyridin-3-yl-urea;

1-((R)-1-{6-[2,2-Bis-(4-hydroxy-phenyl)-ethylamino]-9-[(1R,2S,3R,4S)-2,3-dihydroxy-4-(4-hydroxymethyl-[1,2,3]triazol-2-yl)-cyclopentyl]-9H-purin-2-yl}-pyrrolidin-3-yl)-3-(3-hydroxy-benzyl)-urea;

4-[3-((R)-1-{6-[2,2-Bis-(4-hydroxy-phenyl)-ethylamino]-9-[(1R,2S,3R,4S)-2,3-dihydroxy-4-(4-hydroxymethyl-[1,2,3]triazol-2-yl)-cyclopentyl]-9H-purin-2-yl}-pyrrolidin-3-yl)-ureido]-benzenesulfonamide;

3-[3-((R)-1-{6-[2,2-Bis-(4-hydroxy-phenyl)-ethylamino]-9-[(1R,2S,3R,4S)-2,3-dihydroxy-4-(4-hydroxymethyl-[1,2,3]triazol-2-yl)-cyclopentyl]-9H-purin-2-yl}-pyrrolidin-3-yl)-ureido]-benzenesulfonamide;

1-{(R)-1-[9-[(1R,2S,3R,4S)-2,3-Dihydroxy-4-(5-hydroxymethyl-tetrazol-2-yl)-cyclopentyl]-6-(2,2-diphenyl-ethylamino)-9H-purin-2-yl]-pyrrolidin-3-yl}-3-pyridin-3-yl-urea;

1-{(R)-1-[9-[(1R,2S,3R,4S)-2,3-Dihydroxy-4-(5-hydroxymethyl-tetrazol-2-yl)-cyclopentyl]-6-(2,2-diphenyl-ethylamino)-9H-purin-2-yl]-pyrrolidin-3-yl}-3-(3-hydroxy-benzyl)-urea;

4-(3-{(R)-1-[9-[(1R,2S,3R,4S)-2,3-Dihydroxy-4-(5-hydroxymethyl-tetrazol-2-yl)-cyclopentyl]-6-(2,2-diphenyl-ethylamino)-9H-purin-2-yl]-pyrrolidin-3-yl}-ureido)-benzenesulfonamide;

3-(3-{(R)-1-[9-[(1R,2S,3R,4S)-2,3-Dihydroxy-4-(5-hydroxymethyl-tetrazol-2-yl)-cyclopentyl]-6-(2,2-diphenyl-ethylamino)-9H-purin-2-yl]-pyrrolidin-3-yl}-ureido)-benzenesulfonamide;

1-{(R)-1-[9-[(1R,2S,3R,4S)-2,3-Dihydroxy-4-(5-hydroxymethyl-tetrazol-2-yl)-cyclopentyl]-6-((S)-1-hydroxymethyl-2-phenyl-ethylamino)-9H-purin-2-yl]-pyrrolidin-3-yl}-3-pyridin-3-yl-urea;

1-{(R)-1-[9-[(1R,2S,3R,4S)-2,3-Dihydroxy-4-(5-hydroxymethyl-tetrazol-2-yl)-cyclopentyl]-6-((S)-1-hydroxymethyl-2-phenyl-ethylamino)-9H-purin-2-yl]-pyrrolidin-3-yl}-3-(3-hydroxy-benzyl)-urea;

4-(3-{(R)-1-[9-[(1R,2S,3R,4S)-2,3-Dihydroxy-4-(5-hydroxymethyl-tetrazol-2-yl)-cyclopentyl]-6-((S)-1-hydroxymethyl-2-phenyl-ethylamino)-9H-purin-2-yl]-pyrrolidin-3-yl}-ureido)-benzenesulfonamide;

3-(3-{(R)-1-[9-[(1R,2S,3R,4S)-2,3-Dihydroxy-4-(5-hydroxymethyl-tetrazol-2-yl)-cyclopentyl]-6-((S)-1-hydroxymethyl-2-phenyl-ethylamino)-9H-purin-2-yl]-pyrrolidin-3-yl}-ureido)-benzenesulfonamide;

1-((R)-1-{6-[2,2-Bis-(4-hydroxy-phenyl)-ethylamino]-9-[(1R,2S,3R,4S)-2,3-dihydroxy-4-(5-hydroxymethyl-tetrazol-2-yl)-cyclopentyl]-9H-purin-2-yl}-pyrrolidin-3-yl)-3-pyridin-3-yl-urea;

1-((R)-1-{6-[2,2-Bis-(4-hydroxy-phenyl)-ethylamino]-9-[(1R,2S,3R,4S)-2,3-dihydroxy-4-(5-hydroxymethyl-tetrazol-2-yl)-cyclopentyl]-9H-purin-2-yl}-pyrrolidin-3-yl)-3-(3-hydroxy-benzyl)-urea;

4-[3-((R)-1-{6-[2,2-Bis-(4-hydroxy-phenyl)-ethylamino]-9-[(1R,2S,3R,4S)-2,3-dihydroxy-4-(5-hydroxymethyl-tetrazol-2-yl)-cyclopentyl]-9H-purin-2-yl}-pyrrolidin-3-yl)-ureido]-benzenesulfonamide;

3-[3-((R)-1-{6-[2,2-Bis-(4-hydroxy-phenyl)-ethylamino]-9-[(1R,2S,3R,4S)-2,3-dihydroxy-4-(5-hydroxymethyl-tetrazol-2-yl)-cyclopentyl]-9H-purin-2-yl}-pyrrolidin-3-yl)-ureido]-benzenesulfonamide; and 3-[3-((R)-1-{6-[2,2-Bis-phenyl-ethylamino]-9-[(1R,2S,3R,4S)-2,3-dihydroxy-4-(5-ethyl-tetrazol-2-yl)-cyclopentyl]-9H-purin-2-yl}-pyrrolidin-3-yl)-ureido]-benzenesulfonamide;

or stereoisomers or pharmaceutically acceptable salts thereof.

2. The compound according to claim 1, in combination with an anti-inflammatory, bronchodilatory, anti-histamine or anti-tussive drug substance, said compound and said drug substance being in the same or different pharmaceutical composition.

3. A pharmaceutical composition comprising as active ingredient a compound according to claim 1, optionally together with a pharmaceutically acceptable diluent or carrier.

* * * * *